United States Patent
Kobozev et al.

(10) Patent No.: US 10,795,927 B2
(45) Date of Patent: Oct. 6, 2020

(54) ON-DEMAND METADATA EXTRACTION OF CLINICAL IMAGE DATA

(71) Applicant: Commvault Systems, Inc., Tinton Falls, NJ (US)

(72) Inventors: Oleg Kobozev, Jamison, PA (US); Lei Wang, Manalapan, NJ (US); Jun H. Ahn, Manalapan, NJ (US); Vishal Prakashchand Khule, Bangalore (IN)

(73) Assignee: Commvault Systems, Inc., Tinton Falls, NJ (US)

( * ) Notice: Subject to any disclaimer, the term of this patent is extended or adjusted under 35 U.S.C. 154(b) by 350 days.

(21) Appl. No.: 15/889,026

(22) Filed: Feb. 5, 2018

(65) Prior Publication Data
US 2019/0243911 A1    Aug. 8, 2019

(51) Int. Cl.
| G06F 16/00 | (2019.01) |
| G06F 16/58 | (2019.01) |
| G16H 30/40 | (2018.01) |
| G16H 30/20 | (2018.01) |
| G06F 16/51 | (2019.01) |

(52) U.S. Cl.
CPC .............. *G06F 16/58* (2019.01); *G06F 16/51* (2019.01); *G16H 30/20* (2018.01); *G16H 30/40* (2018.01)

(58) Field of Classification Search
CPC .................................. G06F 16/51; G06F 16/58
See application file for complete search history.

(56) References Cited

U.S. PATENT DOCUMENTS

| 4,394,732 | A | 7/1983 | Swenson |
| 4,686,620 | A | 8/1987 | Ng |
| 4,995,035 | A | 2/1991 | Cole et al. |
| 5,005,122 | A | 4/1991 | Griffin et al. |
| 5,093,912 | A | 3/1992 | Dong et al. |
| 5,133,065 | A | 7/1992 | Cheffetz et al. |

(Continued)

FOREIGN PATENT DOCUMENTS

| EP | 0259912 A1 | 3/1988 |
| EP | 0405926 A2 | 1/1991 |

(Continued)

OTHER PUBLICATIONS

"Multi Instancing," retrieved from http://documentation.commvault.com/hds/release_8_0_0/books_online_1/english_us/deployment/install/misc/multi_instancing.htm[Feb. 18, 2014 11:57:19 AM] on Feb. 18, 2014, 3 pages.

(Continued)

*Primary Examiner* — Jean M Corrielus
(74) *Attorney, Agent, or Firm* — Perkins Coie LLP

(57) ABSTRACT

A method and system for providing on-demand updating of metadata information associated with clinical image data files is disclosed. The system allows for extracting, on the fly, additional metadata fields from clinical image data files and re-indexing the metadata to include the additional fields so that an end-user can perform operations (e.g., searching, browsing, etc.) based on the newly indexed fields. The metadata fields may be defined in a configurable schema file (e.g., XML, YML, etc.). The system can gain efficiencies by, for example, reading only a subset of the DICOM file (e.g., reading only the first few kilobytes that contain the header), scanning only a subset of source data folders, etc.

19 Claims, 20 Drawing Sheets

(56) References Cited

U.S. PATENT DOCUMENTS

| | | |
|---|---|---|
| 5,193,154 A | 3/1993 | Kitajima et al. |
| 5,212,772 A | 5/1993 | Masters |
| 5,212,784 A | 5/1993 | Sparks |
| 5,226,157 A | 7/1993 | Nakano et al. |
| 5,239,647 A | 8/1993 | Anglin et al. |
| 5,241,668 A | 8/1993 | Eastridge et al. |
| 5,241,670 A | 8/1993 | Eastridge et al. |
| 5,276,860 A | 1/1994 | Fortier et al. |
| 5,276,867 A | 1/1994 | Kenley et al. |
| 5,287,500 A | 2/1994 | Stoppani, Jr. |
| 5,321,816 A | 6/1994 | Rogan et al. |
| 5,333,315 A | 7/1994 | Saether et al. |
| 5,347,653 A | 9/1994 | Flynn et al. |
| 5,386,545 A | 1/1995 | Gombos, Jr. et al. |
| 5,410,700 A | 4/1995 | Fecteau et al. |
| 5,448,718 A | 9/1995 | Cohn et al. |
| 5,448,724 A | 9/1995 | Hayashi |
| 5,450,592 A | 9/1995 | McLeod |
| 5,485,606 A | 1/1996 | Midgdey et al. |
| 5,491,810 A | 2/1996 | Allen |
| 5,495,607 A | 2/1996 | Pisello et al. |
| 5,504,873 A | 4/1996 | Martin et al. |
| 5,537,568 A | 7/1996 | Yanai et al. |
| 5,544,345 A | 8/1996 | Carpenter et al. |
| 5,544,347 A | 8/1996 | Yanai et al. |
| 5,559,957 A | 9/1996 | Duyanovich et al. |
| 5,564,037 A | 10/1996 | Lam |
| 5,608,865 A | 3/1997 | Midgely et al. |
| 5,613,134 A | 3/1997 | Lucus et al. |
| 5,619,644 A | 4/1997 | Crockett et al. |
| 5,634,052 A | 5/1997 | Morris |
| 5,638,509 A | 6/1997 | Dunphy et al. |
| 5,659,614 A | 8/1997 | Bailey, III |
| 5,666,501 A | 9/1997 | Jones et al. |
| 5,673,381 A | 9/1997 | Huai et al. |
| 5,673,382 A | 9/1997 | Cannon et al. |
| 5,699,361 A | 12/1997 | Ding et al. |
| 5,711,010 A | 1/1998 | Naddell et al. |
| 5,729,743 A | 3/1998 | Squibb |
| 5,740,405 A | 4/1998 | DeGraaf |
| 5,751,997 A | 5/1998 | Kullick et al. |
| 5,758,359 A | 5/1998 | Saxon |
| 5,758,649 A | 6/1998 | Iwashita et al. |
| 5,761,677 A | 6/1998 | Senator et al. |
| 5,764,972 A | 6/1998 | Crouse et al. |
| 5,778,165 A | 7/1998 | Saxon |
| 5,778,395 A | 7/1998 | Whiting et al. |
| 5,812,398 A | 9/1998 | Nielsen |
| 5,813,009 A | 9/1998 | Johnson et al. |
| 5,813,017 A | 9/1998 | Morris |
| 5,864,846 A | 1/1999 | Voorhees et al. |
| 5,872,905 A | 2/1999 | Ono et al. |
| 5,875,478 A | 2/1999 | Blumenau |
| 5,887,134 A | 3/1999 | Ebrahim |
| 5,894,585 A | 4/1999 | Inoue et al. |
| 5,896,531 A | 4/1999 | Curtis et al. |
| 5,901,327 A | 5/1999 | Ofek |
| 5,924,102 A | 7/1999 | Perks |
| 5,950,205 A | 9/1999 | Aviani, Jr. |
| 5,983,239 A | 10/1999 | Beeler, Jr. |
| 5,991,753 A | 11/1999 | Wilde |
| 6,009,275 A | 12/1999 | DeKoning et al. |
| 6,012,053 A | 1/2000 | Pant et al. |
| 6,021,415 A | 2/2000 | Cannon et al. |
| 6,026,414 A | 2/2000 | Anglin |
| 6,052,735 A | 4/2000 | Ulrich et al. |
| 6,064,821 A | 5/2000 | Shough et al. |
| 6,073,128 A | 6/2000 | Pongracz et al. |
| 6,076,148 A | 6/2000 | Kedem |
| 6,091,518 A | 7/2000 | Anabuki et al. |
| 6,094,416 A | 7/2000 | Ying |
| 6,112,304 A | 8/2000 | Clawson |
| 6,131,095 A | 10/2000 | Low et al. |
| 6,131,190 A | 10/2000 | Sidwell |
| 6,148,412 A | 11/2000 | Cannon et al. |
| 6,154,787 A | 11/2000 | Urevig et al. |
| 6,161,111 A | 12/2000 | Mutalik et al. |
| 6,167,402 A | 12/2000 | Yeager |
| 6,182,198 B1 | 1/2001 | Hubis et al. |
| 6,212,512 B1 | 4/2001 | Barney et al. |
| 6,239,800 B1 | 5/2001 | Miller et al. |
| 6,253,217 B1 | 6/2001 | Dourish et al. |
| 6,260,069 B1 | 7/2001 | Anglin |
| 6,266,679 B1 | 7/2001 | Szalwinski et al. |
| 6,266,784 B1 | 7/2001 | Hsiao et al. |
| 6,269,431 B1 | 7/2001 | Dunham |
| 6,275,953 B1 | 8/2001 | Vahalia et al. |
| 6,298,439 B1 | 10/2001 | Beglin |
| 6,301,592 B1 | 10/2001 | Aoyama et al. |
| 6,308,175 B1 | 10/2001 | Lang et al. |
| 6,324,581 B1 | 11/2001 | Xu et al. |
| 6,327,590 B1 | 12/2001 | Chidlovskii et al. |
| 6,327,612 B1 | 12/2001 | Watanabe et al. |
| 6,328,766 B1 | 12/2001 | Long |
| 6,330,570 B1 | 12/2001 | Crighton |
| 6,330,642 B1 | 12/2001 | Carteau |
| 6,341,287 B1 | 1/2002 | Sziklai et al. |
| 6,343,287 B1 | 1/2002 | Kumar et al. |
| 6,343,324 B1 | 1/2002 | Hubis et al. |
| 6,345,288 B1 | 2/2002 | Reed et al. |
| RE37,601 E | 3/2002 | Eastridge et al. |
| 6,356,801 B1 | 3/2002 | Goodman et al. |
| 6,363,462 B1 | 3/2002 | Bergsten |
| 6,367,073 B2 | 4/2002 | Elledge |
| 6,374,363 B1 | 4/2002 | Wu et al. |
| 6,389,432 B1 | 5/2002 | Pothapragada et al. |
| 6,418,478 B1 | 7/2002 | Ignatius et al. |
| 6,421,678 B2 | 7/2002 | Smiga et al. |
| 6,421,711 B1 | 7/2002 | Blumenau et al. |
| 6,442,706 B1 | 8/2002 | Wahl et al. |
| 6,470,332 B1 | 10/2002 | Weschler |
| 6,484,162 B1 | 11/2002 | Edlund et al. |
| 6,487,561 B1 | 11/2002 | Ofek et al. |
| 6,487,644 B1 | 11/2002 | Huebsch et al. |
| 6,502,205 B1 | 12/2002 | Yanai et al. |
| 6,538,669 B1 | 2/2003 | Devireddy et al. |
| 6,539,388 B1 | 3/2003 | Hattori et al. |
| 6,549,918 B1 | 4/2003 | Probert, Jr. et al. |
| 6,557,039 B1 | 4/2003 | Leong et al. |
| 6,564,228 B1 | 5/2003 | O'Connor |
| 6,618,771 B1 | 9/2003 | Leja et al. |
| 6,629,110 B2 | 9/2003 | Cane et al. |
| 6,647,399 B2 | 11/2003 | Zaremba |
| 6,658,526 B2 | 12/2003 | Nguyen et al. |
| 6,662,218 B2 | 12/2003 | Mighdoll et al. |
| 6,675,177 B1 | 1/2004 | Webb |
| 6,675,299 B2 | 1/2004 | Porter et al. |
| 6,691,232 B1 | 2/2004 | Wood et al. |
| 6,721,767 B2 | 4/2004 | De Meno et al. |
| 6,732,088 B1 | 5/2004 | Glance |
| 6,732,231 B1 | 5/2004 | Don et al. |
| 6,732,244 B2 | 5/2004 | Ashton et al. |
| 6,745,178 B1 | 6/2004 | Goldring |
| 6,816,941 B1 | 9/2004 | Ricketts |
| 6,820,070 B2 | 11/2004 | Goldman et al. |
| 6,839,803 B1 | 1/2005 | Tsai |
| 6,850,994 B2 | 2/2005 | Gabryjelski |
| 6,860,422 B2 | 3/2005 | Hull et al. |
| 6,865,568 B2 | 3/2005 | Chau |
| 6,871,182 B1 | 3/2005 | Winnard et al. |
| 6,892,221 B2 | 5/2005 | Ricart et al. |
| 6,898,650 B1 | 5/2005 | Gao et al. |
| 6,948,038 B2 | 9/2005 | Berkowitz et al. |
| 6,948,039 B2 | 9/2005 | Biessener et al. |
| 6,957,186 B1 | 10/2005 | Guheen et al. |
| 6,970,997 B2 | 11/2005 | Shibayama et al. |
| 6,976,039 B2 | 12/2005 | Chefalas et al. |
| 6,995,675 B2 | 2/2006 | Curkendall et al. |
| 6,996,616 B1 | 2/2006 | Leighton et al. |
| 7,003,641 B2 | 2/2006 | Prahlad et al. |
| 7,028,079 B2 | 4/2006 | Mastrianni et al. |
| 7,035,880 B1 | 4/2006 | Crescenti et al. |
| 7,039,860 B1 | 5/2006 | Gautestad et al. |
| 7,054,960 B1 | 5/2006 | Bezbaruah et al. |

(56) References Cited

U.S. PATENT DOCUMENTS

| | | |
|---|---|---|
| 7,058,661 B2 | 6/2006 | Ciaramitaro et al. |
| 7,099,901 B2 | 8/2006 | Sutoh et al. |
| 7,107,298 B2 | 9/2006 | Prahlad et al. |
| 7,107,416 B2 | 9/2006 | Stuart et al. |
| 7,133,870 B1 | 11/2006 | Tripp et al. |
| 7,139,826 B2 | 11/2006 | Watanabe et al. |
| 7,139,846 B1 | 11/2006 | Rossi |
| 7,146,387 B1 | 12/2006 | Russo et al. |
| 7,155,421 B1 | 12/2006 | Haldar |
| 7,155,481 B2 | 12/2006 | Prahlad et al. |
| 7,159,081 B2 | 1/2007 | Suzuki |
| 7,171,468 B2 | 1/2007 | Yeung et al. |
| 7,171,585 B2 | 1/2007 | Gail et al. |
| 7,185,152 B2 | 2/2007 | Takahashi et al. |
| 7,188,141 B2 | 3/2007 | Novaes |
| 7,240,100 B1 | 7/2007 | Wein et al. |
| 7,246,207 B2 | 7/2007 | Kottomtharayil et al. |
| 7,269,664 B2 | 9/2007 | Hutsch et al. |
| 7,284,033 B2 | 10/2007 | Jhanji |
| 7,287,047 B2 | 10/2007 | Kavuri |
| 7,290,017 B1 | 10/2007 | Wang et al. |
| 7,313,659 B2 | 12/2007 | Suzuki |
| 7,315,923 B2 | 1/2008 | Retnamma et al. |
| 7,328,325 B1 | 2/2008 | Solis et al. |
| 7,340,640 B1 | 3/2008 | Karr |
| 7,343,453 B2 | 3/2008 | Prahlad et al. |
| 7,346,623 B2 | 3/2008 | Prahlad et al. |
| 7,346,676 B1 | 3/2008 | Swildens et al. |
| 7,346,751 B2 | 3/2008 | Prahlad et al. |
| 7,376,947 B2 | 5/2008 | Evers |
| 7,379,978 B2 | 5/2008 | Anderson et al. |
| 7,383,379 B2 | 6/2008 | Patterson et al. |
| 7,386,535 B1 | 6/2008 | Kalucha et al. |
| 7,395,282 B1 | 7/2008 | Crescenti et al. |
| 7,421,460 B2 | 9/2008 | Chigusa et al. |
| 7,424,543 B2 | 9/2008 | Rice, III |
| 7,434,219 B2 | 10/2008 | De Meno et al. |
| 7,457,790 B2 | 11/2008 | Kochunni et al. |
| 7,472,142 B2 | 12/2008 | Prahlad et al. |
| 7,496,841 B2 | 2/2009 | Hadfield et al. |
| 7,529,782 B2 | 5/2009 | Prahlad et al. |
| 7,536,291 B1 | 5/2009 | Vijayan Retnamma et al. |
| 7,543,125 B2 | 6/2009 | Gokhale |
| 7,565,484 B2 | 7/2009 | Ghosal et al. |
| 7,577,689 B1 | 8/2009 | Masinter et al. |
| 7,577,694 B2 | 8/2009 | Nakano et al. |
| 7,581,077 B2 | 8/2009 | Ignatius et al. |
| 7,584,469 B2 | 9/2009 | Mitekura et al. |
| 7,587,715 B1 | 9/2009 | Barrett et al. |
| 7,593,935 B2 | 9/2009 | Sullivan |
| 7,596,713 B2 | 9/2009 | Mani-Meitav et al. |
| 7,603,626 B2 | 10/2009 | Williams et al. |
| 7,606,844 B2 | 10/2009 | Kottomtharayil |
| 7,610,285 B1 | 10/2009 | Zoellner et al. |
| 7,617,262 B2 | 11/2009 | Prahlad et al. |
| 7,656,849 B1 | 2/2010 | Evans |
| 7,668,884 B2 | 2/2010 | Prahlad et al. |
| 7,673,175 B2 | 3/2010 | Mora et al. |
| 7,676,542 B2 | 3/2010 | Moser et al. |
| 7,689,899 B2 | 3/2010 | Leymaster et al. |
| 7,698,520 B2 | 4/2010 | Minami et al. |
| 7,730,031 B2 | 6/2010 | Forster |
| 7,734,593 B2 | 6/2010 | Prahlad et al. |
| 7,734,669 B2 | 6/2010 | Kottomtharayil et al. |
| 7,747,579 B2 | 6/2010 | Prahlad et al. |
| 7,751,628 B1 | 7/2010 | Reisman |
| 7,761,409 B2 | 7/2010 | Stefik et al. |
| 7,792,789 B2 | 9/2010 | Prahlad et al. |
| 7,801,871 B2 | 9/2010 | Gosnell |
| 7,814,118 B2 | 10/2010 | Kottomtharayil et al. |
| 7,827,266 B2 | 11/2010 | Gupta |
| 7,831,445 B2 * | 11/2010 | Reiner .................. G06F 19/321 705/2 |
| 7,831,793 B2 | 11/2010 | Chakravarty et al. |
| 7,840,537 B2 | 11/2010 | Gokhale et al. |
| 7,844,676 B2 | 11/2010 | Prahlad et al. |
| 7,865,517 B2 | 1/2011 | Prahlad et al. |
| 7,882,077 B2 | 2/2011 | Gokhale et al. |
| 7,882,093 B2 | 2/2011 | Kottomtharayil et al. |
| 7,882,097 B1 | 2/2011 | Ogilvie |
| 7,937,393 B2 | 5/2011 | Prahlad et al. |
| 7,937,420 B2 | 5/2011 | Tabellion et al. |
| 7,937,702 B2 | 5/2011 | De Meno et al. |
| 7,984,063 B2 | 7/2011 | Kottomtharayil et al. |
| 7,984,435 B2 | 7/2011 | Kokkinen |
| 8,037,028 B2 | 10/2011 | Prahlad et al. |
| 8,055,627 B2 | 11/2011 | Prahlad et al. |
| 8,060,514 B2 | 11/2011 | Arrouye et al. |
| 8,069,218 B1 | 11/2011 | Tormasov |
| 8,078,607 B2 | 12/2011 | Oztekin et al. |
| 8,099,428 B2 | 1/2012 | Kottomtharayil et al. |
| 8,108,427 B2 | 1/2012 | Prahlad et al. |
| 8,117,173 B2 | 2/2012 | Gurevich et al. |
| 8,117,549 B2 * | 2/2012 | Reiner .................. G16H 30/20 715/751 |
| 8,126,854 B1 | 2/2012 | Sreedharan |
| 8,131,784 B1 | 3/2012 | Zhuge et al. |
| 8,145,742 B1 | 3/2012 | Bunte et al. |
| 8,156,086 B2 | 4/2012 | Lu et al. |
| 8,170,995 B2 | 4/2012 | Kavuri |
| 8,200,638 B1 | 6/2012 | Zheng et al. |
| 8,219,524 B2 | 7/2012 | Gokhale |
| 8,229,954 B2 | 7/2012 | Kottomtharayil et al. |
| 8,230,054 B2 | 7/2012 | Mutnuru et al. |
| 8,230,195 B2 | 7/2012 | Amarendran et al. |
| RE43,678 E | 9/2012 | Major et al. |
| 8,285,681 B2 | 10/2012 | Prahlad et al. |
| 8,307,177 B2 | 11/2012 | Prahlad et al. |
| 8,347,088 B2 | 1/2013 | Moore et al. |
| 8,352,954 B2 | 1/2013 | Gokhale et al. |
| 8,356,209 B2 | 1/2013 | Gunabalasubramaniam et al. |
| 8,364,652 B2 | 1/2013 | Vijayan et al. |
| 8,370,166 B2 | 2/2013 | Ronnewinkel |
| 8,396,804 B1 * | 3/2013 | Dala .................. G06F 19/3418 705/52 |
| 8,396,838 B2 | 3/2013 | Brockway et al. |
| 8,468,538 B2 | 6/2013 | Attarde et al. |
| 8,473,585 B1 | 6/2013 | Smith et al. |
| 8,477,618 B2 | 7/2013 | Martin |
| 8,495,331 B2 | 7/2013 | Matsumoto et al. |
| 8,510,573 B2 | 8/2013 | De Meno et al. |
| 8,578,120 B2 | 11/2013 | Attarde et al. |
| 8,612,394 B2 | 12/2013 | Prahlad et al. |
| 8,655,850 B2 | 2/2014 | Ngo et al. |
| 8,706,867 B2 | 4/2014 | Vijayan |
| 8,707,070 B2 | 4/2014 | Muller |
| 8,719,809 B2 | 5/2014 | Gokhale |
| 8,725,688 B2 | 5/2014 | Lad |
| 8,769,048 B2 | 7/2014 | Kottomtharayil |
| 8,775,823 B2 | 7/2014 | Gokhale et al. |
| 8,782,064 B2 | 7/2014 | Kottomtharayil et al. |
| 8,826,284 B1 | 9/2014 | Fuller |
| 8,832,706 B2 | 9/2014 | Gokhale et al. |
| 8,849,762 B2 | 9/2014 | Kumarasamy et al. |
| 8,959,299 B2 | 2/2015 | Ngo et al. |
| 8,966,288 B2 | 2/2015 | Ignatius et al. |
| 9,092,378 B2 | 7/2015 | Kumarasamy et al. |
| 9,122,692 B2 | 9/2015 | Dalal et al. |
| 9,128,883 B2 | 9/2015 | Gokhale et al. |
| 9,262,226 B2 | 2/2016 | Gokhale et al. |
| 9,274,803 B2 | 3/2016 | De Meno et al. |
| 9,348,827 B1 | 5/2016 | Patwardhan et al. |
| 9,411,821 B1 | 8/2016 | Patwardhan |
| 9,444,811 B2 | 9/2016 | Nara et al. |
| 9,459,968 B2 | 10/2016 | Vijayan |
| 9,633,216 B2 | 4/2017 | Gokhale et al. |
| 9,639,400 B2 | 5/2017 | Gokhale et al. |
| 9,645,762 B2 | 5/2017 | Nara et al. |
| 9,648,100 B2 | 5/2017 | Klose et al. |
| 9,740,574 B2 | 8/2017 | Kochunni et al. |
| 2001/0012986 A1 | 8/2001 | Conan et al. |
| 2001/0028363 A1 | 10/2001 | Nomoto et al. |
| 2002/0032878 A1 | 3/2002 | Karpf |
| 2002/0049883 A1 | 4/2002 | Schneider et al. |

(56) References Cited

U.S. PATENT DOCUMENTS

| | | |
|---|---|---|
| 2003/0028592 A1 | 2/2003 | Ooho et al. |
| 2003/0046313 A1 | 3/2003 | Leung et al. |
| 2003/0046396 A1 | 3/2003 | Richter et al. |
| 2003/0050979 A1 | 3/2003 | Takahashi |
| 2003/0065897 A1 | 4/2003 | Sadowsky et al. |
| 2003/0101086 A1 | 5/2003 | San Miguel |
| 2004/0039689 A1 | 2/2004 | Penney et al. |
| 2004/0068713 A1 | 4/2004 | Yannakoyorgos et al. |
| 2004/0098383 A1 | 5/2004 | Tabellion et al. |
| 2004/0220980 A1 | 11/2004 | Forster |
| 2004/0267815 A1 | 12/2004 | De Mes |
| 2005/0039069 A1 | 2/2005 | Prahlad et al. |
| 2005/0076087 A1 | 4/2005 | Budd et al. |
| 2005/0097070 A1 | 5/2005 | Enis et al. |
| 2005/0216788 A1 | 9/2005 | Mani-Meitav et al. |
| 2005/0246510 A1 | 11/2005 | Retnamma et al. |
| 2005/0251786 A1 | 11/2005 | Citron et al. |
| 2006/0036619 A1 | 2/2006 | Fuerst et al. |
| 2006/0070061 A1 | 3/2006 | Cox et al. |
| 2006/0080370 A1 | 4/2006 | Torii et al. |
| 2006/0110286 A1 | 5/2006 | Boukas |
| 2006/0115802 A1 | 6/2006 | Reynolds |
| 2006/0116999 A1 | 6/2006 | Dettinger et al. |
| 2006/0149604 A1 | 7/2006 | Miller |
| 2006/0149724 A1 | 7/2006 | Ritter et al. |
| 2006/0177114 A1 | 8/2006 | Tongdee et al. |
| 2006/0195678 A1 | 8/2006 | Jalobeanu |
| 2006/0195838 A1 | 8/2006 | Epstein |
| 2006/0224846 A1 | 10/2006 | Amarendran et al. |
| 2006/0224852 A1 | 10/2006 | Kottomtharayil et al. |
| 2006/0265396 A1 | 11/2006 | Raman et al. |
| 2006/0271935 A1 | 11/2006 | Cox et al. |
| 2006/0282900 A1 | 12/2006 | Johnson et al. |
| 2007/0014347 A1 | 1/2007 | Prechtl et al. |
| 2007/0022122 A1 | 1/2007 | Bahar et al. |
| 2007/0022145 A1 | 1/2007 | Kavuri |
| 2007/0028229 A1 | 2/2007 | Knatcher |
| 2007/0043715 A1 | 2/2007 | Kaushik et al. |
| 2007/0061298 A1 | 3/2007 | Wilson et al. |
| 2007/0067595 A1 | 3/2007 | Ghose |
| 2007/0128899 A1 | 6/2007 | Mayer |
| 2007/0136541 A1 | 6/2007 | Herz et al. |
| 2007/0143497 A1 | 6/2007 | Kottomtharayil et al. |
| 2007/0156783 A1 | 7/2007 | Zbogar-Smith et al. |
| 2007/0166674 A1 | 7/2007 | Kochunni et al. |
| 2007/0174246 A1 | 7/2007 | Sigurdsson et al. |
| 2007/0208788 A1 | 9/2007 | Chakravarty et al. |
| 2007/0220308 A1 | 9/2007 | Yeung et al. |
| 2007/0226320 A1 | 9/2007 | Hager et al. |
| 2007/0226535 A1 | 9/2007 | Gokhale |
| 2007/0250810 A1 | 10/2007 | Tittizer et al. |
| 2008/0022003 A1 | 1/2008 | Alve |
| 2008/0033903 A1 | 2/2008 | Carol et al. |
| 2008/0155205 A1 | 6/2008 | Gokhale et al. |
| 2008/0177994 A1 | 7/2008 | Mayer |
| 2008/0263565 A1 | 10/2008 | Luther et al. |
| 2008/0282048 A1 | 11/2008 | Miura |
| 2009/0119322 A1 | 5/2009 | Mills et al. |
| 2009/0150168 A1 | 6/2009 | Schmidt |
| 2009/0171883 A1 | 7/2009 | Kochunni et al. |
| 2009/0187908 A1 | 7/2009 | He et al. |
| 2009/0228531 A1 | 9/2009 | Baumann et al. |
| 2009/0307448 A1 | 12/2009 | Gokhale et al. |
| 2009/0319534 A1 | 12/2009 | Gokhale |
| 2010/0005259 A1 | 1/2010 | Prahlad et al. |
| 2010/0036772 A1 | 2/2010 | Arceneaux |
| 2010/0070466 A1 | 3/2010 | Prahlad et al. |
| 2010/0070474 A1 | 3/2010 | Lad |
| 2010/0114837 A1 | 5/2010 | Prahlad et al. |
| 2010/0125477 A1 | 5/2010 | Mousseau et al. |
| 2010/0161773 A1 | 6/2010 | Prahlad et al. |
| 2010/0172301 A1 | 7/2010 | Watfa et al. |
| 2010/0180332 A1 | 7/2010 | Ben-Yochanan et al. |
| 2010/0205582 A1 | 8/2010 | Liu |
| 2010/0250549 A1 | 9/2010 | Muller et al. |
| 2010/0262911 A1 | 10/2010 | Kaplan et al. |
| 2010/0299490 A1 | 11/2010 | Attarde et al. |
| 2010/0306283 A1 | 12/2010 | Johnson et al. |
| 2010/0306643 A1 | 12/2010 | Chabot et al. |
| 2010/0332401 A1 | 12/2010 | Prahlad et al. |
| 2010/0332454 A1 | 12/2010 | Prahlad et al. |
| 2010/0332479 A1 | 12/2010 | Prahlad et al. |
| 2011/0016091 A1 | 1/2011 | Prahlad et al. |
| 2011/0069179 A1 | 3/2011 | Bathiche et al. |
| 2011/0087664 A1* | 4/2011 | Westin ............... G16H 30/40 707/736 |
| 2011/0161299 A1 | 6/2011 | Prahlad et al. |
| 2011/0231362 A1 | 9/2011 | Attarde et al. |
| 2011/0302141 A1 | 12/2011 | Nadathur et al. |
| 2012/0011515 A1 | 1/2012 | Jolfaei et al. |
| 2012/0066633 A1 | 3/2012 | Saito et al. |
| 2012/0084524 A1 | 4/2012 | Gokhale et al. |
| 2012/0084782 A1 | 4/2012 | Chou et al. |
| 2012/0094674 A1 | 4/2012 | Wu |
| 2012/0150818 A1 | 6/2012 | Vijayan Retnamma et al. |
| 2012/0150826 A1 | 6/2012 | Vijayan Retnamma et al. |
| 2012/0203742 A1 | 8/2012 | Goodman et al. |
| 2012/0254116 A1 | 10/2012 | Thereska et al. |
| 2012/0254824 A1 | 10/2012 | Bansod |
| 2012/0263191 A1 | 10/2012 | Baron |
| 2012/0272205 A1 | 10/2012 | Fox et al. |
| 2012/0275598 A1 | 11/2012 | Vimpari et al. |
| 2012/0317085 A1 | 12/2012 | Green et al. |
| 2013/0006625 A1 | 1/2013 | Gunatilake et al. |
| 2013/0007710 A1 | 1/2013 | Vedula et al. |
| 2013/0024429 A1 | 1/2013 | Raas |
| 2013/0024568 A1 | 1/2013 | Popczynski et al. |
| 2013/0046817 A1 | 2/2013 | Isbister |
| 2013/0066784 A1* | 3/2013 | Dala ................. G06F 21/602 705/51 |
| 2013/0104027 A1 | 4/2013 | Bennett et al. |
| 2013/0110854 A1 | 5/2013 | Lockhart et al. |
| 2013/0111326 A1 | 5/2013 | Lockhart et al. |
| 2013/0136253 A1 | 5/2013 | Liberman Ben-Ami et al. |
| 2013/0179405 A1 | 7/2013 | Bunte et al. |
| 2013/0219458 A1 | 8/2013 | Ramanathan |
| 2013/0232184 A1 | 9/2013 | Grube et al. |
| 2013/0238562 A1 | 9/2013 | Kumarasamy et al. |
| 2013/0238969 A1 | 9/2013 | Smith et al. |
| 2013/0262387 A1 | 10/2013 | Varadharajan et al. |
| 2013/0262396 A1 | 10/2013 | Kripalani et al. |
| 2013/0262410 A1 | 10/2013 | Liu et al. |
| 2013/0262615 A1 | 10/2013 | Ankireddypalle et al. |
| 2013/0262706 A1 | 10/2013 | Stahlberg et al. |
| 2013/0326159 A1 | 12/2013 | Vijayan et al. |
| 2013/0332412 A1 | 12/2013 | Amarendran |
| 2014/0025641 A1 | 1/2014 | Kumarasamy et al. |
| 2014/0026000 A1 | 1/2014 | Ma et al. |
| 2014/0040210 A1 | 2/2014 | Avery et al. |
| 2014/0040580 A1 | 2/2014 | Kripalani |
| 2014/0046900 A1 | 2/2014 | Kumarasamy et al. |
| 2014/0046904 A1 | 2/2014 | Kumarasamy |
| 2014/0086127 A1 | 3/2014 | Kim et al. |
| 2014/0108351 A1 | 4/2014 | Nallathambi et al. |
| 2014/0108355 A1 | 4/2014 | Prahlad et al. |
| 2014/0108470 A1 | 4/2014 | Lad |
| 2014/0150023 A1 | 5/2014 | Gudorf et al. |
| 2014/0180664 A1 | 6/2014 | Kochunni et al. |
| 2014/0181032 A1 | 6/2014 | Kumarasamy et al. |
| 2014/0181037 A1 | 6/2014 | Pawar et al. |
| 2014/0181045 A1 | 6/2014 | Pawar et al. |
| 2014/0181085 A1 | 6/2014 | Gokhale et al. |
| 2014/0181443 A1 | 6/2014 | Kottomtharayil et al. |
| 2014/0188805 A1 | 7/2014 | Vijayan |
| 2014/0188812 A1 | 7/2014 | Vijayan |
| 2014/0189432 A1 | 7/2014 | Gokhale et al. |
| 2014/0201140 A1 | 7/2014 | Vibhor |
| 2014/0201142 A1 | 7/2014 | Varadharajan et al. |
| 2014/0201150 A1 | 7/2014 | Kumarasamy et al. |
| 2014/0201154 A1 | 7/2014 | Varadharajan et al. |
| 2014/0201155 A1 | 7/2014 | Vijayan et al. |
| 2014/0201161 A1 | 7/2014 | Kumarasamy et al. |
| 2014/0201162 A1 | 7/2014 | Kumarasamy et al. |
| 2014/0201171 A1 | 7/2014 | Vijayan et al. |

(56) References Cited

U.S. PATENT DOCUMENTS

| | | | |
|---|---|---|---|
| 2014/0250076 A1 | 9/2014 | Lad | |
| 2014/0279922 A1 | 9/2014 | Kottomtharayil | |
| 2014/0281214 A1 | 9/2014 | Rehm et al. | |
| 2014/0289189 A1 | 9/2014 | Chan | |
| 2014/0289196 A1 | 9/2014 | Chan | |
| 2014/0365443 A1 | 12/2014 | Goel et al. | |
| 2015/0081948 A1 | 3/2015 | Thereska et al. | |
| 2015/0193229 A1 | 7/2015 | Bansod | |
| 2015/0227355 A1 | 8/2015 | Tripoli et al. | |
| 2015/0234879 A1 | 8/2015 | Baldwin et al. | |
| 2015/0244775 A1 | 8/2015 | Vibhor et al. | |
| 2015/0278024 A1 | 10/2015 | Barman et al. | |
| 2015/0301903 A1 | 10/2015 | Mutha et al. | |
| 2015/0324226 A1 | 11/2015 | Gokhale et al. | |
| 2015/0324233 A1 | 11/2015 | Gokhale et al. | |
| 2015/0331872 A1* | 11/2015 | Westin | G16H 40/67 707/756 |
| 2015/0331899 A1 | 11/2015 | Gokhale et al. | |
| 2015/0347238 A1 | 12/2015 | Kumarasamy et al. | |
| 2016/0037057 A1* | 2/2016 | Westin | H04N 5/91 348/207.1 |
| 2016/0110266 A1 | 4/2016 | Nara et al. | |
| 2017/0024152 A1 | 1/2017 | Bhagi et al. | |
| 2017/0024286 A1 | 1/2017 | Vijayan | |
| 2017/0083517 A1* | 3/2017 | Mitkar | G06F 16/51 |
| 2017/0134492 A1 | 5/2017 | Klose et al. | |
| 2017/0160970 A1 | 6/2017 | Gokhale et al. | |
| 2017/0160971 A1 | 6/2017 | Gokhale et al. | |
| 2017/0199924 A1 | 7/2017 | Gokhale et al. | |
| 2017/0206018 A1 | 7/2017 | Nara et al. | |
| 2017/0206112 A1 | 7/2017 | Gokhale et al. | |
| 2018/0247707 A1* | 8/2018 | Westin | G06Q 50/22 |

FOREIGN PATENT DOCUMENTS

| | | |
|---|---|---|
| EP | 0467546 A2 | 1/1992 |
| EP | 0774715 A1 | 5/1997 |
| EP | 0809184 A1 | 11/1997 |
| EP | 0899662 A1 | 3/1999 |
| EP | 0910019 A2 | 4/1999 |
| EP | 0981090 A1 | 2/2000 |
| EP | 0986011 | 3/2000 |
| EP | 1035690 | 9/2000 |
| GB | 2216368 A | 10/1989 |
| JP | 07-046271 A | 2/1995 |
| JP | 7073080 A | 3/1995 |
| JP | 8044598 A | 2/1996 |
| JP | 2000035969 | 2/2000 |
| JP | 2003531435 | 10/2003 |
| WO | WO-9513580 A1 | 5/1995 |
| WO | WO-9912098 A1 | 3/1999 |
| WO | WO-00/58865 | 10/2000 |
| WO | WO-0106368 A1 | 1/2001 |
| WO | WO-01/16693 | 3/2001 |
| WO | WO-0180005 | 10/2001 |
| WO | WO-2010057199 | 5/2010 |

OTHER PUBLICATIONS

U.S. Appl. No. 15/680,031 of Klose et al., filed Aug. 17, 2017.
U.S. Appl. No. 15/682,085 of Kochunni et al., filed Aug. 21, 2017.
Abbot, K., et al., "Administration and Autonomy in a Republican-Transparent Distributed DBMS." VLDB. 1988.
Armstead et al., "Implementation of a Campwide Distributed Mass Storage Service: The Dream vs. Reality," IEEE, Sep. 11-14, 1995, pp. 190-199.
Arneson, "Mass Storage Archiving in Network Environments," Digest of Papers, Ninth IEEE Symposium on Mass Storage Systems, Oct. 31, 1988-Nov. 3, 1988, pp. 45-50, Monterey, CA.
Cabrera et al., "ADSM: A Multi-Platform, Scalable, Backup and Archive Mass Storage System," Digest of Papers, Compcon '95, Proceedings of the 40th IEEE Computer Society International Conference, Mar. 5, 1995-Mar. 9, 1995, pp. 420-427, San Francisco, CA.
Eitel, "Backup and Storage Management in Distributed Heterogeneous Environments," IEEE, Jun. 12-16, 1994, pp. 124-126.
Extended European Search Report for Application No. EP 09767119, dated Feb. 11, 2013, 12 pages.
Gait, J., "The Optical File Cabinet: A Random-Access File System for Write-Once Optical Disks," IEEE Computer, vol. 21, No. 6, pp. 11-22 (Jun. 1988).
Hennessy et al., "Computer Architecture—A Quantitative Approach", 2nd Edition, 1996, pp. 246-250.
Hsiao, David K., "Federated databases and systems: part i—a tutorial on tehri data sharing." The VLDB Journal 1.1 (1992): 127-179.
Hutchinson, Norman C., et al. "Logical vs. physical file system backup." OSDI. vol. 99. 1999, 12 pages.
International Search Report and Written Opinion for International Application No. PCT/US09/32325, dated Mar. 17, 2009, 11 pages.
Jander, M., "Launching Storage-Area Net," Data Communications, US, McGraw Hill, NY, vol. 27, No. 4 (Mar. 21, 1998), pp. 64-72.
Matthews, Jeanna, et al. "Data protection and rapid recovery from attack with a virtual private file server and virtual machine appliances," Proceedings of the IASTED International Conference on Communication, Network and Information Security (CNIS 2005). 2005, 14 pages.
Microsoft Press Computer Dictionary Third Edition, "Data Compression," Microsoft Press, 1997, p. 130.
Pitoura et al., "Locating Objects in Mobile Computing", IEEE Transactions on Knowledge and Data Engineering, vol. 13, No. 4, Jul./Aug. 2001, pp. 571-592.
Pollack, et al., "Quota enforcement for high-performance distributed storage systems," 24th IEEE Conference on Mass Storage Systems and Technologies (MSST 2007), Sep. 24-27, 2007, pp. 72-86.
Prigge, "Review: ExaGrid aces disk-to-disk backup," Jan. 3, 2013, InfoWorld, 12 pages.
Quinlan, Sean. "A cached worm file system." Software: Practice and Experience 21.12 (1991 ): 1289-1299.
Rosenblum et al., "The Design and Implementation of a Log-Structured File System," Operating Systems Review SIGOPS, vol. 25, No. 5, New York, US, pp. 1-15 (May 1991).
Rowe et al., "Indexes for User Access to Large Video Databases", Storage and Retrieval for Image and Video Databases II, IS,& T/SPIE Symp. on Elec. Imaging Sci. & Tech., Feb. 1994, pp. 1-12.
Veeravalli, B., "Network Caching Strategies for a Shared Data Distribution for a Predefined Service Demand Sequence," IEEE Transactions on Knowledge and Data Engineering, vol. 15, No. 6, Nov./Dec. 2003, pp. 1487-1497.
Wu, Chin-Hsien, Tei-Wei Kuo, and Li-Pin Chang. "Efficient initialization and crash recovery for log-based file systems over flash memory." Proceedings of the 2006 ACM symposium on Applied computing. ACM, 2006, 5 pages.
Examination Report in European Patent Application No. 09767119. 2, dated Feb. 1, 2018, 3 pages.
U.S. Appl. No. 15/705,629 of Bhagi et al., filed Sep. 15, 2017.
U.S. Appl. No. 15/920,375 of Mutha et al., filed Mar. 13, 2018.
U.S. Appl. No. 15/889,057 of Bhagi et al., filed Feb. 5, 2018.
U.S. Appl. No. 15/927,018 of Ashraf et al., filed Mar. 20, 2018.
U.S. Appl. No. 15/937,783 of Rao, filed Mar. 27, 2018.
U.S. Appl. No. 15/937,796 of Bangalore, filed Mar. 27, 2018.
U.S. Appl. No. 15/939,235 of Liu, filed Mar. 28, 2018.

\* cited by examiner

Clinical Image Data File Scan

Clinical Image Data File Scan

Choose Patient Folders

605 — Toggle All

*Checked patient folders over CV Healthcare Server will be re-indexed.

610

| Patient Folder |
|---|
| ☐ \\VNA\DICOM\STORAGE\104ED36F |
| ☐ \\VNA\DICOM\STORAGE\1CE7C8F0 |
| ☐ \\VNA\DICOM\STORAGE\5C571432 |
| ☐ \\VNA\DICOM\STORAGE\96D48E0E |
| ☐ \\VNA\DICOM\STORAGE\A36D838F |
| ☐ \\VNA\DICOM\STORAGE\848FD228 |
| ☐ \\VNA\DICOM\STORAGE\Pt15 |
| ☐ \\VNA\DICOM\STORAGE\Pt3 |
| ☐ \\VNA\DICOM\STORAGE\Pt4 |

Back    Start — 615

FIG. 6A

| Element | | VR | Length | Value |
|---|---|---|---|---|
| UL | (0002,0000) Group Length | UL | 4 | 198 |
| OB | (0002,0001) File Meta Information Version | OB | 2 | (binary data) |
| UI | (0002,0002) Media Storage SOP Class UID | UI | 28 | 1.2.840.10008.5.1.4.1.1.128 (Positron Emission Tomog |
| UI | (0002,0003) Media Storage SOP Instance UID | UI | 64 | 1.3.6.1.4.1.14519.5.2.1.5099.8010.325052274783161 |
| UI | (0002,0010) Transfer Syntax UID | UI | 20 | 1.2.840.10008.1.2.1 (Explicit VR Little Endian) |
| UI | (0002,0012) Implementation Class UID | UI | 18 | 1.2.40.0.13.1.1.1 |
| SH | (0002,0013) Implementation Version Name | SH | 14 | dcm4che-1.4.34 |
| CS | (0008,0008) Image Type | CS | 16 | ORIGINAL\PRIMARY |
| UI | (0008,0016) SOP Class UID | UI | 28 | 1.2.840.10008.5.1.4.1.1.128 (Positron Emission Tomog |
| UI | (0008,0018) SOP Instance UID | UI | 64 | 1.3.6.1.4.1.14519.5.2.1.5099.8010.325052274783161 |
| DA | (0008,0020) Study Date | DA | 8 | 20000517 |
| DA | (0008,0021) Series Date | DA | 8 | 20000517 |
| DA | (0008,0022) Acquisition Date | DA | 8 | 20000517 |
| DA | (0008,0023) Content Date | DA | 8 | 20000517 |
| TM | (0008,0030) Study Time | TM | 6 | 083539 |
| TM | (0008,0031) Series Time | TM | 6 | 083539 |
| TM | (0008,0032) Acquisition Time | TM | 6 | 083539 |
| TM | (0008,0033) Content Time | TM | 6 | 083539 |
| SH | (0008,0050) Accession Number | SH | 16 | 2819497684894126 |
| CS | (0008,0060) Modality | CS | 2 | PT |
| LO | (0008,0070) Manufacturer | LO | 24 | Philips Medical Systems |
| PN | (0008,0090) Referring Physician's Name | PN | 2 | |
| SH | (0008,1010) Station Name | SH | 10 | gx041-svr |
| LO | (0008,103E) Series Description | LO | 30 | pxxxxs1_JON_nac.img: 3D-RAMLA |
| LO | (0008,1090) Manufacturer's Model Name | LO | 16 | Guardian Body® |
| PN | (0010,0010) Patient's Name | PN | 10 | 0522c0027 |
| LO | (0010,0020) Patient ID | LO | 10 | 0522c0027 |
| DA | (0010,0030) Patient's Birth Date | DA | 0 | |
| CS | (0010,0040) Patient's Sex | CS | 2 | M |
| DS | (0010,1030) Patient's Weight | DS | 10 | 64.860000 |
| LO | (0012,0010) Clinical Trial Sponsor Name | LO | 46 | American_College_of_Radiology_Imaging_Network |
| LO | (0012,0020) Clinical Trial Protocol ID | LO | 4 | 4500 |
| LO | (0012,0021) Clinical Trial Protocol Name | LO | 22 | RTOG 0502 / ACRIN 4500 |
| LO | (0012,0042) Clinical Trial Subject Reading ID | LO | 2 | 12 |

FIG. 7

```
DicomAttributesCo...on_ReIndexTest.xml    📌    ✕ MetaInfoXMLC

<?xml version="1.0" encoding="utf-8"?>
<DicomAttributesConfiguration>
  <Level name="Patient">
    <Attribute> ... </Attribute>
    <Attribute>
      <Name>PatientID</Name>
      <Group>0010</Group>
      <Element>0020</Element>
    </Attribute>
    <Attribute> ... </Attribute>
    <Attribute>
      <Name>PatientName</Name>
      <Group>0010</Group>
      <Element>0010</Element>
    </Attribute>
  </Level>
  <Level name="Study">
    <Attribute> ... </Attribute>
    <Attribute> ... </Attribute>
    <Attribute> ... </Attribute>
    <Attribute> ... </Attribute>
    <Attribute> ... </Attribute>
    <Attribute>
      <Name>StudyDate</Name>
      <Group>0008</Group>
      <Element>0020</Element>
    </Attribute>
    <Attribute>
      <Name>StudyTime</Name>
      <Group>0008</Group>
      <Element>0030</Element>
    </Attribute>
    <Attribute>
      <Name>ReferringPhysicianName</Name>
      <Group>0008</Group>
      <Element>0090</Element>
    </Attribute>
    <Attribute> ... </Attribute>
```

FIG. 8

ON-DEMAND METADATA EXTRACTION OF CLINICAL IMAGE DATA

INCORPORATION BY REFERENCE TO ANY PRIORITY APPLICATIONS

Any and all applications, if any, for which a foreign or domestic priority claim is identified in the Application Data Sheet of the present application are hereby incorporated by reference in their entireties under 37 CFR 1.57.

COPYRIGHT NOTICE

A portion of the disclosure of this patent document contains material which is subject to copyright protection. The copyright owner has no objection to the facsimile reproduction by anyone of the patent document and/or the patent disclosure as it appears in the United States Patent and Trademark Office patent file and/or records, but otherwise reserves all copyrights whatsoever.

BACKGROUND

Businesses recognize the commercial value of their data and seek reliable, cost-effective ways to protect the information stored on their computer networks while minimizing impact on productivity. A company might back up critical computing systems such as databases, file servers, web servers, virtual machines, and so on as part of a daily, weekly, or monthly maintenance schedule. The company may similarly protect computing systems used by its employees, such as those used by an accounting department, marketing department, engineering department, and so forth. Given the rapidly expanding volume of data under management, companies also continue to seek innovative techniques for managing data growth, for example, by migrating data to lower-cost storage over time, reducing redundant data, pruning lower priority data, etc. Enterprises also increasingly view their stored data as a valuable asset and look for solutions that leverage their data. For instance, data analysis capabilities, information management, improved data presentation and access features, and the like, are in increasing demand.

BRIEF DESCRIPTION OF THE DRAWINGS

FIG. 53 depicts an illustrative graphical user interface for receiving upload or reindexing selection from a user.

FIG. 6A depicts an illustrative graphical user interface for receiving file/folder selection(s) from a user for clinical image data reindexing.

FIG. 7 depicts an example of a DICOM header file.

FIG. 8 depicts an example of a configurable schema file.

DETAILED DESCRIPTION

Figure 1A:
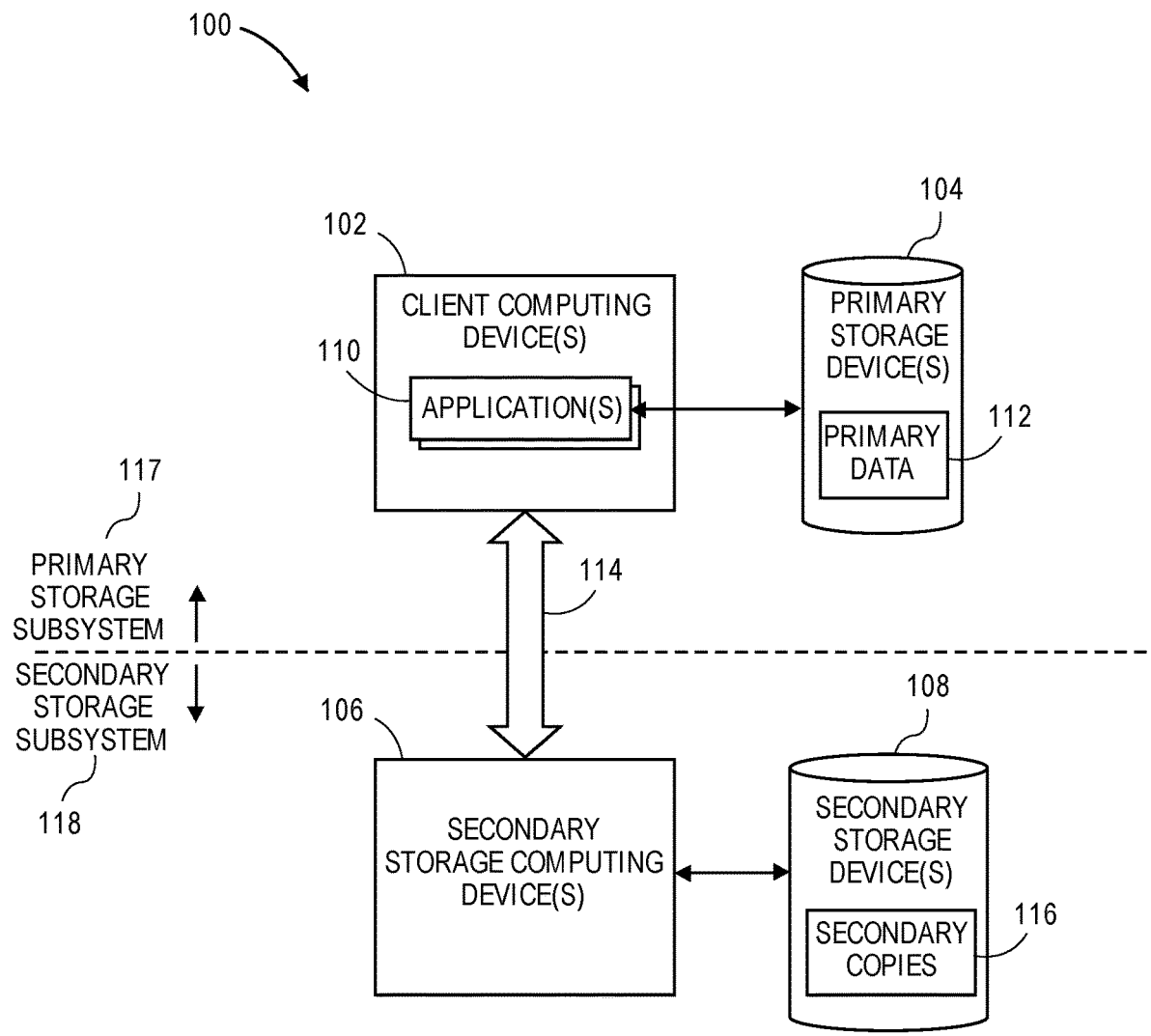
FIG. 1A is a block diagram illustrating an exemplary information management system.

Clinical Image Archiving tools allow a user to archive, search, and restore medical/clinical imaging data (e.g., Digital Imaging and Communications in Medicine (DICOM), Analyze, Neuroimaging Informatics Technology Initiative (WTI), or Mine files) generated using, from example, medical imaging software. All of the archived data can be centrally located and accessible from any medical imaging endpoint. Generally, clinical image data files are very large and can contain hundreds of metadata fields in a preamble. Given the storage and data transmission burden associated with these large files, typical Clinical Image Archiving tools currently store only a subset of the metadata fields for each clinical image data file.

A software, firmware, and/or hardware system that provides on-demand updating of metadata information associated with clinical image data files is disclosed. The system allows for extracting, on the fly, additional metadata fields from clinical image data files and re-indexing the metadata to include the additional fields so that an end-user can perform operations (e.g., searching, browsing, etc.) based on the newly indexed fields. The metadata fields may be defined in a configurable schema file (e.g., XML, YML, etc.). The system can gain efficiencies by, for example, reading only a subset of the DICOM file (e.g., reading only the first few kilobytes that contain the header), scanning only a subset of source data folders, etc.

Detailed descriptions and examples of systems and methods according to one or more illustrative embodiments of the present invention may be found in the section entitled On-Demand Metadata Extraction And Re-Indexing Of Clinical Image Data System, as well as in the section entitled Example Embodiments, and also in FIGS. 3-8 herein. Furthermore, components and functionality for systems and method for providing on-demand updating of metadata information associated with clinical image data files may be configured and/or incorporated into information management systems such as those described herein in FIGS. 1A-1H and 2A-2C.

Various embodiments described herein are intimately tied to, enabled by, and would not exist except for, computer technology. For example, systems and methods for on-demand metadata extraction and re-indexing of clinical image data described herein in reference to various embodiments cannot reasonably be performed by humans alone, without the computer technology upon which they are implemented.

Information Management System Overview

With the increasing importance of protecting and leveraging data, organizations simply cannot risk losing critical data. Moreover, runaway data growth and other modern realities make protecting and managing data increasingly difficult. There is therefore a need for efficient, powerful, and user-friendly solutions for protecting and managing data and for smart and efficient management of data storage. Depending on the size of the organization, there may be many data production sources which are under the purview of tens, hundreds, or even thousands of individuals. In the past, individuals were sometimes responsible for managing and protecting their own data, and a patchwork of hardware and software point solutions may have been used in any given organization. These solutions were often provided by different vendors and had limited or no interoperability. Certain embodiments described herein address these and other shortcomings of prior approaches by implementing scalable, unified, organization-wide information management, including data storage management.

FIG. 1A shows one such information management system 100 (or "system 100"), which generally includes combinations of hardware and software configured to protect and manage data and metadata that are generated and used by computing devices in system 100. System 100 may be referred to in some embodiments as a "storage management system" or a "data storage management system." System 100 performs information management operations, some of which may be referred to as "storage operations" or "data storage operations," to protect and manage the data residing in and/or managed by system 100. The organization that employs system 100 may be a corporation or other business entity, non-profit organization, educational institution, household, governmental agency, or the like.

Generally, the systems and associated components described herein may be compatible with and/or provide some or all of the functionality of the systems and corresponding components described in one or more of the following U.S. patents/publications and patent applications assigned to Commvault Systems, Inc., each of which is hereby incorporated by reference in its entirety herein:

U.S. Pat. No. 7,035,880, entitled "Modular Backup and Retrieval System Used in Conjunction With a Storage Area Network";

U.S. Pat. No. 7,107,298, entitled "System And Method For Archiving Objects In An Information Store";

U.S. Pat. No. 7,246,207, entitled "System and Method for Dynamically Performing Storage Operations in a Computer Network";

U.S. Pat. No. 7,315,923, entitled "System And Method For Combining Data Streams In Pipelined Storage Operations In A Storage Network";

U.S. Pat. No. 7,343,453, entitled "Hierarchical Systems and Methods for Providing a Unified View of Storage Information";

U.S. Pat. No. 7,395,282, entitled "Hierarchical Backup and Retrieval System";

U.S. Pat. No. 7,529,782, entitled "System and Methods for Performing a Snapshot and for Restoring Data";

U.S. Pat. No. 7,617,262, entitled "System and Methods for Monitoring Application Data in a Data Replication System";

U.S. Pat. No. 7,734,669, entitled "Managing Copies Of Data";

U.S. Pat. No. 7,747,579, entitled "Metabase for Facilitating Data Classification";

U.S. Pat. No. 8,156,086, entitled "Systems And Methods For Stored Data Verification";

U.S. Pat. No. 8,170,995, entitled "Method and System for Offline Indexing of Content and Classifying Stored Data";

U.S. Pat. No. 8,230,195, entitled "System And Method For Performing Auxiliary Storage Operations";

U.S. Pat. No. 8,285,681, entitled "Data Object Store and Server for a Cloud Storage Environment, Including Data Deduplication and Data Management Across Multiple Cloud Storage Sites";

U.S. Pat. No. 8,307,177, entitled "Systems And Methods For Management Of Virtualization Data";

U.S. Pat. No. 8,364,652, entitled "Content-Aligned, Block-Based Deduplication";

U.S. Pat. No. 8,578,120, entitled "Block-Level Single Instancing";

U.S. Pat. No. 8,954,446, entitled "Client-Side Repository in a Networked Deduplicated Storage System";

U.S. Pat. No. 9,020,900, entitled "Distributed Deduplicated Storage System";

U.S. Pat. No. 9,098,495, entitled "Application-Aware and Remote Single Instance Data Management";

U.S. Pat. No. 9,239,687, entitled "Systems and Methods for Retaining and Using Data Block Signatures in Data Protection Operations";

U.S. Pat. Pub. No. 2006/0224846, entitled "System and Method to Support Single Instance Storage Operations";

U.S. Pat. Pub. No. 2014/0201170, entitled "High Availability Distributed Deduplicated Storage System";

U.S. patent application Ser. No. 14/721,971, entitled "Replication Using Deduplicated Secondary Copy Data";

U.S. Patent Application No. 62/265,339 entitled "Live Synchronization and Management of Virtual Machines across Computing and Virtualization Platforms and Using Live Synchronization to Support Disaster Recovery";

U.S. Patent Application No. 62/273,286 entitled "Redundant and Robust Distributed Deduplication Data Storage System";

U.S. Patent Application No. 62/294,920, entitled "Data Protection Operations Based on Network Path Information";

U.S. Patent Application No. 62/297,057, entitled "Data Restoration Operations Based on Network Path Information"; and U.S. Patent Application No. 62/387,384, entitled "Application-Level Live Synchronization Across Computing Platforms Including Synchronizing Co-Resident Applications To Disparate Standby Destinations And Selectively Synchronizing Some Applications And Not Others".

System 100 includes computing devices and computing technologies. For instance, system 100 can include one or more client computing devices 102 and secondary storage computing devices 106, as well as storage manager 140 or a host computing device for it. Computing devices can include, without limitation, one or more: workstations, personal computers, desktop computers, or other types of generally fixed computing systems such as mainframe computers, servers, and minicomputers. Other computing devices can include mobile or portable computing devices, such as one or more laptops, tablet computers, personal data assistants, mobile phones (such as smartphones), and other mobile or portable computing devices such as embedded computers, set top boxes, vehicle-mounted devices, wearable computers, etc. Servers can include mail servers, file servers, database servers, virtual machine servers, and web servers. Any given computing device comprises one or more processors (e.g., CPU and/or single-core or multi-core processors), as well as corresponding non-transitory computer memory (e.g., random-access memory (RAM)) for storing computer programs which are to be executed by the one or more processors. Other computer memory for mass storage of data may be packaged/configured with the computing device (e.g., an internal hard disk) and/or may be external and accessible by the computing device (e.g., network-attached storage, a storage array, etc.). In some cases, a computing device includes cloud computing resources, which may be implemented as virtual machines. For instance, one or more virtual machines may be provided to the organization by a third-party cloud service vendor.

In some embodiments, computing devices can include one or more virtual machine(s) running on a physical host computing device (or "host machine") operated by the organization. As one example, the organization may use one virtual machine as a database server and another virtual machine as a mail server, both virtual machines operating on the same host machine. A Virtual machine ("VM") is a software implementation of a computer that does not physically exist and is instead instantiated in an operating system of a physical computer (or host machine) to enable applications to execute within the VM's environment, i.e., a VM emulates a physical computer. A VM includes an operating system and associated virtual resources, such as computer memory and processor(s). A hypervisor operates between the VM and the hardware of the physical host machine and is generally responsible for creating and running the VMs. Hypervisors are also known in the art as virtual machine monitors or virtual machine managers or "VMMs", and may be implemented in software, firmware, and/or specialized hardware installed on the host machine. Examples of hypervisors include ESX Server, by VMware, Inc. of Palo Alto, Calif.; Microsoft Virtual Server and Microsoft Windows Server Hyper-V, both by Microsoft Corporation of Redmond, Wash.; Sun xVM by Oracle America Inc, of Santa Clara, Calif.; and Xen by Citrix Systems, Santa Clara, Calif. The hypervisor provides resources to each virtual operating system such as a virtual processor, virtual memory, a virtual network device, and a virtual disk. Each virtual machine has one or more associated virtual disks. The hypervisor typically stores the data of virtual disks in files on the file system of the physical host machine, called virtual machine disk files ("VMDK" in VMware lingo) or virtual hard disk image files (in Microsoft lingo). For example, VMware's ESX Server provides the Virtual Machine File System (VMFS) for the storage of virtual machine disk files. A virtual machine reads data from and writes data to its virtual disk much the way that a physical machine reads data from and writes data to a physical disk. Examples of techniques for implementing information management in a cloud computing environment are described in U.S. Pat. No. 8,285,681. Examples of techniques for implementing information management in a virtualized computing environment are described in U.S. Pat. No. 8,307,177.

Information management system 100 can also include electronic data storage devices, generally used for mass storage of data, including, e.g., primary storage devices 104 and secondary storage devices 108. Storage devices can generally be of any suitable type including, without limitation, disk drives, storage arrays (e.g., storage-area network (SAN) and/or network-attached storage (NAS) technology), semiconductor memory (e.g., solid state storage devices), network attached storage (NAS) devices, tape libraries, or other magnetic, non-tape storage devices, optical media storage devices, DNA/RNA-based memory technology, combinations of the same, etc. In some embodiments, storage devices form part of a distributed file system. In some cases, storage devices are provided in a cloud storage environment (e.g., a private cloud or one operated by a third-party vendor), whether for primary data or secondary copies or both.

Figure 1B:
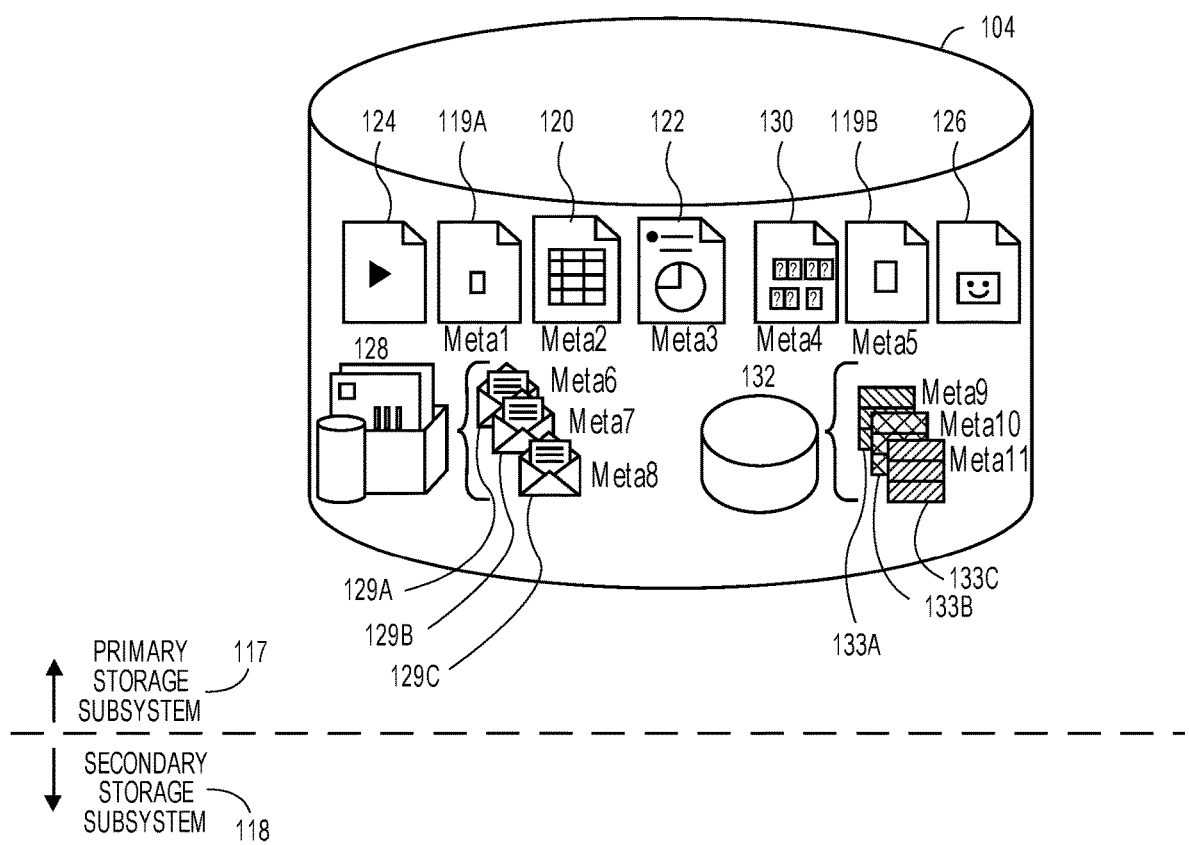
FIG. 1B is a detailed view of a primary storage device, a secondary storage device, and some examples of primary data and secondary copy data.
Figure 1B:
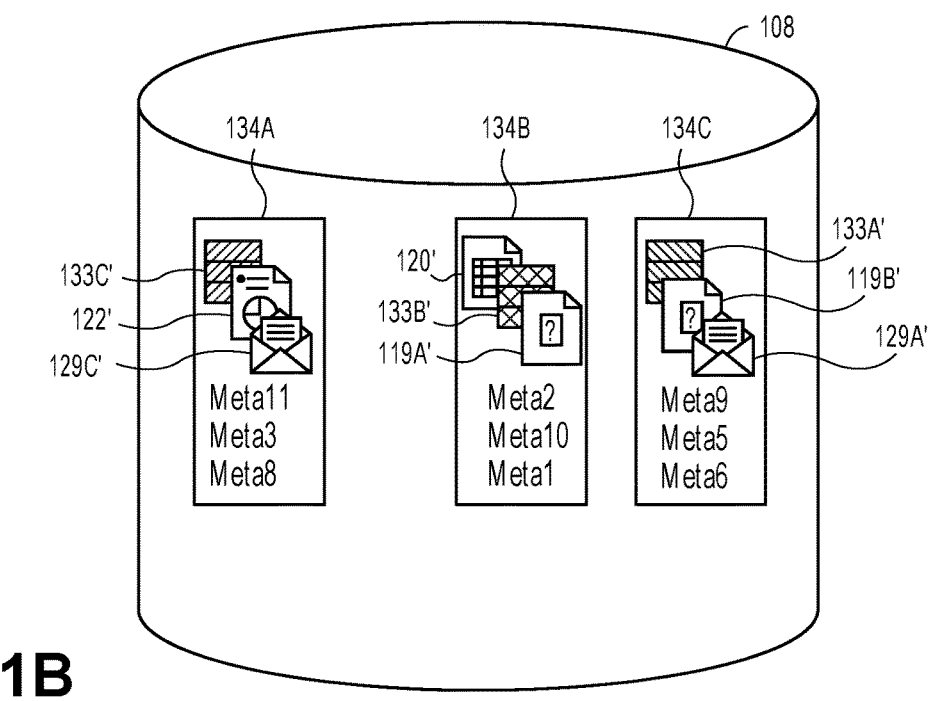
Figure 1C:
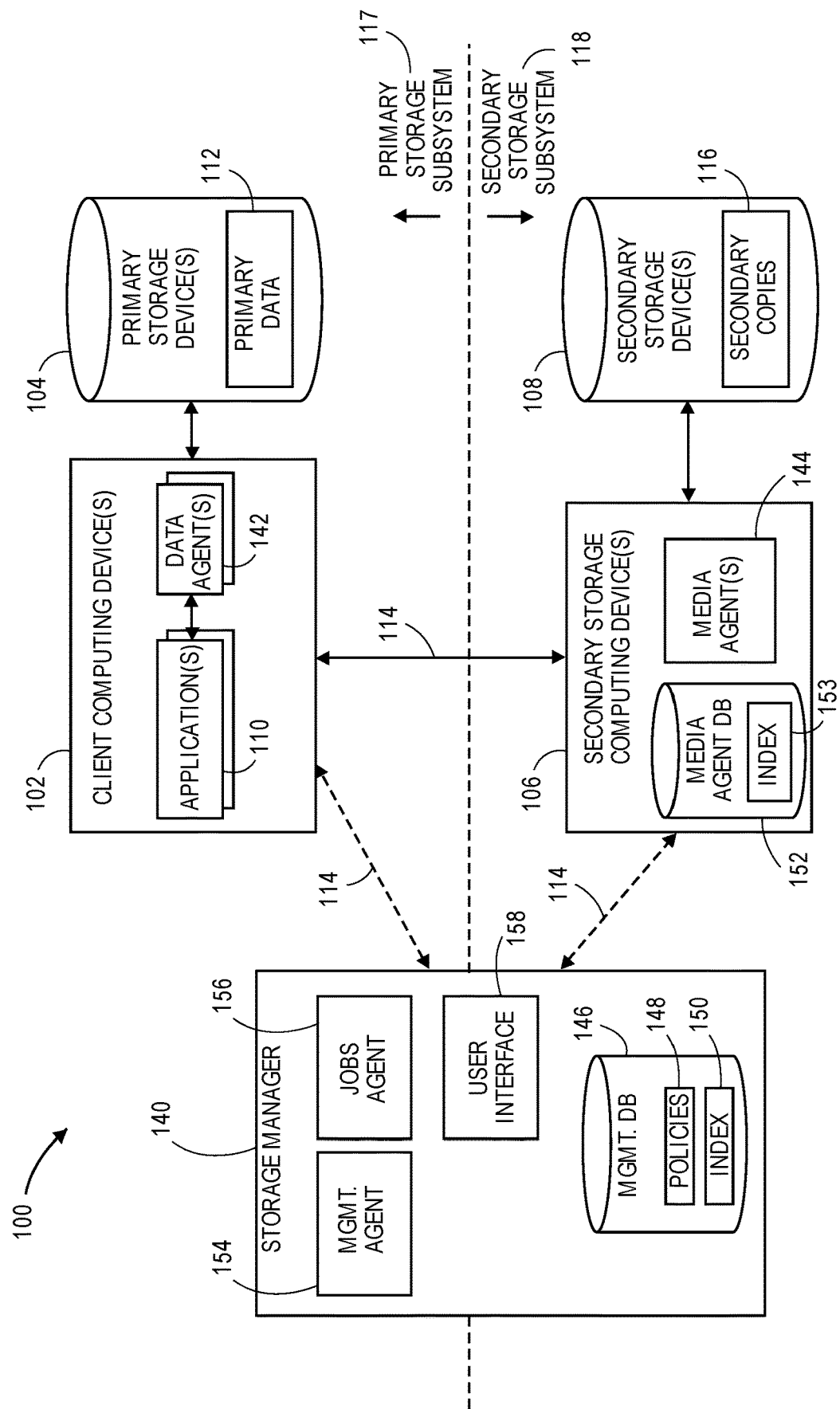
FIG. 1C is a block diagram of an exemplary information management system including a storage manager, one or more data agents, and one or more media agents.

Depending on context, the term "information management system" can refer to generally all of the illustrated hardware and software components in FIG. 1C, or the term may refer to only a subset of the illustrated components. For instance, in some cases, system 100 generally refers to a combination of specialized components used to protect, move, manage, manipulate, analyze, and/or process data and metadata generated by client computing devices 102. However, system 100 in some cases does not include the underlying components that generate and/or store primary data 112, such as the client computing devices 102 themselves, and the primary storage devices 104. Likewise secondary storage devices 108 (e.g., a third-party provided cloud storage environment) may not be part of system 100. As an example, "information management system" or "storage management system" may sometimes refer to one or more of the following components, which will be described in further detail below: storage manager, data agent, and media agent.

One or more client computing devices 102 may be part of system 100, each client computing device 102 having an operating system and at least one application 110 and one or more accompanying data agents executing thereon; and associated with one or more primary storage devices 104 storing primary data 112. Client computing device(s) 102 and primary storage devices 104 may generally be referred to in some cases as primary storage subsystem 117.

Client Computing Devices, Clients and Subclients

Typically, a variety of sources in an organization produce data to be protected and managed. As just one illustrative example, in a corporate environment such data sources can be employee workstations and company servers such as a mail server, a web server, a database server, a transaction server, or the like. In system 100, data generation sources include one or more client computing devices 102. A computing device that has a data agent 142 installed and operating on it is generally referred to as a "client computing device" 102, and may include any type of computing device, without limitation. A client computing device 102 may be associated with one or more users and/or user accounts.

A "client" is a logical component of information management system 100, which may represent a logical grouping of one or more data agents installed on a client computing device 102, Storage manager 140 recognizes a client as a component of system 100, and in some embodiments, may automatically create a client component the first time a data agent 142 is installed on a client computing device 102. Because data generated by executable component(s) 110 is tracked by the associated data agent 142 so that it may be properly protected in system 100, a client may be said to generate data and to store the generated data to primary storage, such as primary storage device 104. However, the terms "client" and "client computing device" as used herein do not imply that a client computing device 102 is necessarily configured in the client/server sense relative to another computing device such as a mail server, or that a client computing device 102 cannot be a server in its own right. As just a few examples, a client computing device 102 can be and/or include mail servers, the servers, database servers, virtual machine servers, and/or web servers.

Each client computing device 102 may have application(s) 110 executing thereon which generate and manipulate the data that is to be protected from loss and managed in system 100. Applications 110 generally facilitate the operations of an organization, and can include, without limitation, mail server applications (e.g., Microsoft Exchange Server), file system applications, mail client applications (e.g., Microsoft Exchange Client), database applications or database management systems (e.g., SQL, Oracle, SAP, Lotus Notes Database), word processing applications (e.g., Microsoft Word), spreadsheet applications, financial applications, presentation applications, graphics and/or video applications, browser applications, mobile applications, entertainment applications, and so on. Each application 110 may be accompanied by an application-specific data agent 142, though not all data agents 142 are application-specific or associated with only application. A file system, e.g., Microsoft Windows Explorer, may be considered an application 110 and may be accompanied by its own data agent 142. Client computing devices 102 can have at least one operating system (e.g., Microsoft Windows, Mac OS X, iOS, IBM z/OS, Linux, other Unix-based operating systems, etc.) installed thereon, which may support or host one or more file systems and other applications 110. In some embodiments, a virtual machine that executes on a host client computing device 102 may be considered an application 110 and may be accompanied by a specific data agent 142 (e.g., virtual server data agent).

Client computing devices 102 and other components in system 100 can be connected to one another via one or more electronic communication pathways 114. For example, a first communication pathway 114 may communicatively couple client computing device 102 and secondary storage computing device 106; a second communication pathway 114 may communicatively couple storage manager 140 and client computing device 102; and a third communication pathway 114 may communicatively couple storage manager 140 and secondary storage computing device 106, etc. (see, e.g., FIG. 1A and FIG. 1C), A communication pathway 114 can include one or more networks or other connection types including one or more of the following, without limitation: the Internet, a wide area network (WAN), a local area network (LAN), a Storage Area Network (SAN), a Fibre Channel (FC) connection, a Small Computer System Interface (SCSI) connection, a virtual private network (VPN), a token ring or TCP/IP based network, an intranet network, a point-to-point link, a cellular network, a wireless data transmission system, a two-way cable system, an interactive kiosk network, a satellite network, a broadband network, a baseband network, a neural network, a mesh network, an ad hoc network, other appropriate computer or telecommunications networks, combinations of the same or the like. Communication pathways 114 in some cases may also include application programming interfaces (APIs) including, e.g., cloud service provider APIs, virtual machine management APIs, and hosted service provider APIs. The underlying infrastructure of communication pathways 114 may be wired and/or wireless, analog and/or digital, or any combination thereof; and the facilities used may be private, public, third-party provided, or any combination thereof, without limitation.

A "subclient" is a logical grouping of all or part of a client's primary data 112. In general, a subclient may be defined according to how the subclient data is to be protected as a unit in system 100. For example, a subclient may be associated with a certain storage policy. A given client may thus comprise several subclients, each subclient associated with a different storage policy. For example, some files may form a first subclient that requires compression and deduplication and is associated with a first storage policy. Other files of the client may form a second subclient that requires a different retention schedule as well as encryption, and may be associated with a different, second storage policy. As a result, though the primary data may be generated by the same application 110 and may belong to one given client, portions of the data may be assigned to different subclients for distinct treatment by system 100. More detail on subclients is given in regard to storage policies below.

Primary Data an Exemplary Primary Storage Devices

Primary data 112 is generally production data or "live" data generated by the operating system and/or applications 110 executing on client computing device 102. Primary data 112 is generally stored on primary storage device(s) 104 and is organized via a file system operating on the client computing device 102. Thus, client computing device(s) 102 and corresponding applications 110 may create, access, modify, write, delete, and otherwise use primary data 112. Primary data 112 is generally in the native format of the source application 110, Primary data 112 is an initial or first stored body of data generated by the source application 110. Primary data 112 in some cases is created substantially directly from data generated by the corresponding source application 110. It can be useful in performing certain tasks to organize primary data 112 into units of different granularities. In general, primary data 112 can include files, directories, file system volumes, data blocks, extents, or any other hierarchies or organizations of data objects. As used herein, a "data object" can refer to (i) any file that is currently addressable by a file system or that was previously addressable by the file system (e.g., an archive file), and/or to (ii) a subset of such a file (e.g., a data block, an extent, etc.). Primary data 112 may include structured data (e.g., database files), unstructured data (e.g., documents), and/or semi-structured data. See, e.g., FIG. 1B.

It can also be useful in performing certain functions of system 100 to access and modify metadata within primary data 112. Metadata generally includes information about data objects and/or characteristics associated with the data objects. For simplicity herein, it is to be understood that, unless expressly stated otherwise, any reference to primary data 112 generally also includes its associated metadata, but references to metadata generally do not include the primary data. Metadata can include, without limitation, one or more of the following: the data owner (e.g., the client or user that generates the data), the last modified time (e.g., the time of the most recent modification of the data object), a data object name (e.g., a file name), a data object size (e.g., a number of bytes of data), information about the content (e.g., an indication as to the existence of a particular search term), user-supplied tags, to/from information for email (e.g., an email sender, recipient, etc.), creation date, file type (e.g., format or application type), last accessed time, application type (e.g., type of application that generated the data object), location/network (e.g., a current, past or future location of the data object and network pathways to/from the data object), geographic location (e.g., GPS coordinates), frequency of change (e.g., a period in which the data object is modified), business unit (e.g., a group or department that generates, manages or is otherwise associated with the data object), aging information (e.g., a schedule, such as a time period, in which the data object is migrated to secondary or long term storage), boot sectors, partition layouts, file location within a file folder directory structure, user permissions, owners, groups, access control lists (ACLs), system metadata (e.g., registry information), combinations of the same or other similar information related to the data object. In addition to metadata generated by or related to the systems and operating systems, some applications 110 and/or other components of system 100 maintain indices of metadata for data objects, e.g., metadata associated with individual email messages. The use of metadata to perform classification and other functions is described in greater detail below.

Primary storage devices 104 storing primary data 112 may be relatively fast and/or expensive technology (e.g., flash storage, a disk drive, a hard-disk storage array, solid state memory, etc.), typically to support high-performance live production environments, Primary data 112 may be highly changeable and/or may be intended for relatively short term retention (e.g., hours, days, or weeks). According to some embodiments, client computing device 102 can access primary data 112 stored in primary storage device 104 by making conventional file system calls via the operating system. Each client computing device 102 is generally associated with and/or in communication with one or more primary storage devices 104 storing corresponding primary data 112. A client computing device 102 is said to be associated with or in communication with a particular primary storage device 104 if it is capable of one or more of: routing and/or storing data (e.g., primary data 112) to the primary storage device 104, coordinating the routing and/or storing of data to the primary storage device 104, retrieving data from the primary storage device 104, coordinating the retrieval of data from the primary storage device 104, and modifying and/or deleting data in the primary storage device 104. Thus, a client computing device 102 may be said to access data stored in an associated storage device 104.

Primary storage device 104 may be dedicated or shared. In some cases, each primary storage device 104 is dedicated to an associated client computing device 102, e.g., a local disk drive. In other cases, one or more primary storage devices 104 can be shared by multiple client computing devices 102, e.g., via a local network, in a cloud storage implementation, etc. As one example, primary storage device 104 can be a storage array shared by a group of client computing devices 102, such as EMC Clarion, EMC Symmetrix, EMC Celerra, Dell EqualLogic, IBM XIV, NetApp FAS, HP EVA, and HP SPAR.

System 100 may also include hosted services (not shown), which may be hosted in some cases by an entity other than the organization that employs the other components of system 100, For instance, the hosted services may be provided by online service providers. Such service providers can provide social networking services, hosted email services, or hosted productivity applications or other hosted applications such as software-as-a-service (SaaS), platform-as-a-service (PaaS), application service providers (ASPs), cloud services, or other mechanisms for delivering functionality via a network. As it services users, each hosted service may generate additional data and metadata, which may be managed by system 100, e.g., as primary data 112, In some cases, the hosted services may be accessed using one of the applications 110. As an example, a hosted mail service may be accessed via browser running on a client computing device 102.

Secondary Copies and Exemplary Secondary Storage Devices

Primary data 112 stored on primary storage devices 104 may be compromised in some cases, such as when an employee deliberately or accidentally deletes or overwrites primary data 112, or primary storage devices 104 can be damaged, lost, or otherwise corrupted. For recovery and/or regulatory compliance purposes, it is therefore useful to generate and maintain copies of primary data 112. Accordingly, system 100 includes one or more secondary storage computing devices 106 and one or more secondary storage devices 108 configured to create and store one or more secondary copies 116 of primary data 112 including its associated metadata. The secondary storage computing devices 106 and the secondary storage devices 108 may be referred to as secondary storage subsystem 118.

Secondary copies 116 can help in search and analysis efforts and meet other information management goals as well, such as: restoring data and/or metadata if an original version is lost (e.g., by deletion, corruption, or disaster); allowing point-in-time recovery; complying with regulatory data retention and electronic discovery (e-discovery) requirements; reducing utilized storage capacity in the production system and/or in secondary storage; facilitating organization and search of data; improving user access to data files across multiple computing devices and/or hosted services; and implementing data retention and pruning policies.

A secondary copy 116 can comprise a separate stored copy of data that is derived from one or more earlier-created stored copies (e.g., derived from primary data 112 or from another secondary copy 116). Secondary copies 116 can include point-in-time data, and may be intended for relatively long-term retention before some or all of the data is moved to other storage or discarded. In some cases, a secondary copy 116 may be in a different storage device than other previously stored copies; and/or may be remote from other previously stored copies. Secondary copies 116 can be stored in the same storage device as primary data 112. For example, a disk array capable of performing hardware snapshots stores primary data 112 and creates and stores hardware snapshots of the primary data 112 as secondary copies 116. Secondary copies 116 may be stored in relatively slow and/or lower cost storage (e.g., magnetic tape). A secondary copy 116 may be stored in a backup or archive format, or in some other format different from the native source application format or other format of primary data 112.

Secondary storage computing devices 106 may index secondary copies 116 (e.g., using a media agent 144), enabling users to browse and restore at a later time and further enabling the lifecycle management of the indexed data, After creation of a secondary copy 116 that represents certain primary data 112, a pointer or other location indicia (e.g., a stub) may be placed in primary data 112, or be otherwise associated with primary data 112, to indicate the current location of a particular secondary copy 116. Since an instance of a data object or metadata in primary data 112 may change over time as it is modified by application 110 (or hosted service or the operating system), system 100 may create and manage multiple secondary copies 116 of a particular data object or metadata, each copy representing the state of the data object in primary data 112 at a particular point in time. Moreover, since an instance of a data object in primary data 112 may eventually be deleted from primary storage device 104 and the file system, system 100 may continue to manage point-in-time representations of that data object, even though the instance in primary data 112 no longer exists. For virtual machines, the operating system and other applications 110 of client computing device(s) 102 may execute within or under the management of virtualization software (e.g., a VMM), and the primary storage device(s) 104 may comprise a virtual disk created on a physical storage device. System 100 may create secondary copies 116 of the files or other data objects in a virtual disk file and/or secondary copies 116 of the entire virtual disk file itself (e.g., of an entire .vmdk file).

Secondary copies 116 are distinguishable from corresponding primary data 112. First, secondary copies 116 can be stored in a different format from primary data 112 (e.g., backup, archive, or other non-native format). For this or other reasons, secondary copies 116 may not be directly usable by applications 110 or client computing device 102 (e.g., via standard system calls or otherwise) without modification, processing, or other intervention by system 100 which may be referred to as "restore" operations. Secondary copies 116 may have been processed by data agent 142 and/or media agent 144 in the course of being created (e.g., compression, deduplication, encryption, integrity markers, indexing, formatting, application-aware metadata, etc.), and thus secondary copy 116 may represent source primary data 112 without necessarily being exactly identical to the source.

Second, secondary copies 116 may be stored on a secondary storage device 108 that is inaccessible to application 110 running on client computing device 102 and/or hosted service. Some secondary copies 116 may be "offline copies," in that they are not readily available (e.g., not mounted to tape or disk). Offline copies can include copies of data that system 100 can access without human intervention (e.g., tapes within an automated tape library, but not yet mounted in a drive), and copies that the system 100 can access only with some human intervention (e.g., tapes located at an offsite storage site).

Using Intermediate Devices for Creating Secondary Copies
Secondary Storage Computing Devices Creating secondary copies can be challenging when hundreds or thousands of client computing devices 102 continually generate large volumes of primary data 112 to be protected. Also, there can be significant overhead involved in the creation of secondary copies 116. Moreover, specialized programmed intelligence and/or hardware capability is generally needed for accessing and interacting with secondary storage devices 108. Client computing devices 102 may interact directly with a secondary storage device 108 to create secondary copies 116, but in view of the factors described above, this approach can negatively impact the ability of client computing device 102 to serve/service application 110 and produce primary data 112. Further, any given client computing device 102 may not be optimized for interaction with certain secondary storage devices 108.

Thus, system 100 may include one or more software and/or hardware components which generally act as intermediaries between client computing devices 102 (that generate primary data 112) and secondary storage devices 108 (that store secondary copies 116). In addition to off-loading certain responsibilities from client computing devices 102, these intermediate components provide other benefits. For instance, as discussed further below with respect to FIG. 1D, distributing some of the work involved in creating secondary copies 116 can enhance scalability and improve system performance. For instance, using specialized secondary storage computing devices 106 and media agents 144 for interfacing with secondary storage devices 108 and/or for performing certain data processing operations can greatly improve the speed with which system 100 performs information management operations and can also improve the capacity of the system to handle large numbers of such operations, while reducing the computational load on the production environment of client computing devices 102. The intermediate components can include one or more secondary storage computing devices 106 as shown in FIG. 1A and/or one or more media agents 144. Media agents are discussed further below (e.g., with respect to FIGS. 1C-1E), These special-purpose components of system 100 comprise specialized programmed intelligence and/or hardware capability for writing to, reading from, instructing, communicating with, or otherwise interacting with secondary storage devices 108.

Secondary storage computing device(s) 106 can comprise any of the computing devices described above, without limitation. In some cases, secondary storage computing device(s) 106 also include specialized hardware componentry and/or software intelligence (e.g., specialized interfaces) for interacting with certain secondary storage device(s) 108 with which they may be specially associated.

To create a secondary copy 116 involving the copying of data from primary storage subsystem 117 to secondary storage subsystem 118, client computing device 102 may communicate the primary data 112 to be copied (or a processed version thereof generated by a data agent 142) to the designated secondary storage computing device 106, via a communication pathway 114. Secondary storage computing device 106 in turn may further process and convey the data or a processed version thereof to secondary storage device 108. One or more secondary copies 116 may be created from existing secondary copies 116, such as in the case of an auxiliary copy operation, described further below.

Exemplary Primary and an Exemplary Secondary Copy

FIG. 1B is a detailed view of some specific examples of primary data stored on primary storage device(s) 104 and secondary copy data stored on secondary storage device(s) 108, with other components of the system removed for the purposes of illustration. Stored on primary storage device(s) 104 are primary data 112 objects including word processing documents 119A-B, spreadsheets 120, presentation documents 122, video files 124, image files 126, email mailboxes 128 (and corresponding email messages 129A-C), HTML/XML or other types of markup language files 130, databases 132 and corresponding tables or other data structures 133A-133C. Some or all primary data 112 objects are associated with corresponding metadata (e.g., "Meta1-11"), which may include file system metadata and/or application-specific metadata, Stored on the secondary storage device(s) 108 are secondary copy 116 data objects 134A-C which may include copies of or may otherwise represent corresponding primary data 112.

Secondary copy data objects 134A-C can individually represent more than one primary data object. For example, secondary copy data object 134A represents three separate primary data objects 133C, 122, and 129C (represented as 133C', 122', and 129C', respectively, and accompanied by corresponding metadata Meta11, Meta3, and Meta8, respectively). Moreover, as indicated by the prime mark ('), secondary storage computing devices 106 or other components in secondary storage subsystem 118 may process the data received from primary storage subsystem 117 and store a secondary copy including a transformed and/or supplemented representation of a primary data object and/or metadata that is different from the original format, e.g., in a compressed, encrypted, deduplicated, or other modified format. For instance, secondary storage computing devices 106 can generate new metadata or other information based on said processing, and store the newly generated information along with the secondary copies. Secondary copy data object 134B represents primary data objects 120, 133B, and 119A as 120", 133B', and 119A', respectively, accompanied by corresponding metadata Meta1, Meta10, and Meta1, respectively. Also, secondary copy data object 134C represents primary data objects 133A, 119B, and 129A as 133A', 119B', and 129A', respectively, accompanied by corresponding metadata Meta9, Meta5, and Meta6, respectively.

Exemplary Information Management System Architecture

System 100 can incorporate a variety of different hardware and software components, which can in turn be organized with respect to one another in many different configurations, depending on the embodiment. There are critical design choices involved in specifying the functional responsibilities of the components and the role of each component in system 100. Such design choices can impact how system 100 performs and adapts to data growth and other changing circumstances. FIG. 1C shows a system 100 designed according to these considerations and includes: storage manager 140, one or more data agents 142 executing on client computing device(s) 102 and configured to process primary data 112, and one or more media agents 144 executing on one or more secondary storage computing devices 106 for performing tasks involving secondary storage devices 108.

Storage Manager

Storage manager 140 is a centralized storage and/or information manager that is configured to perform certain control functions and also to store certain critical information about system 100 hence storage manager 140 is said to manage system 100. As noted, the number of components in system 100 and the amount of data under management can be large. Managing the components and data is therefore a significant task, which can grow unpredictably as the number of components and data scale to meet the needs of the organization. For these and other reasons, according to certain embodiments, responsibility for controlling system 100, or at least a significant portion of that responsibility, is allocated to storage manager 140. Storage manager 140 can be adapted independently according to changing circumstances, without having to replace or re-design the remainder of the system. Moreover, a computing device for hosting and/or operating as storage manager 140 can be selected to best suit the functions and networking needs of storage manager 140. These and other advantages are described in further detail below and with respect to FIG. 1D.

Storage manager 140 may be a software module or other application hosted by a suitable computing device. In some embodiments, storage manager 140 is itself a computing device that performs the functions described herein. Storage manager 140 comprises or operates in conjunction with one or more associated data structures such as a dedicated database (e.g., management database 146), depending on the configuration. The storage manager 140 generally initiates, performs, coordinates, and/or controls storage and other information management operations performed by system 100, e.g., to protect and control primary data 112 and secondary copies 116. In general, storage manager 140 is said to manage system 100, which includes communicating with, instructing, and controlling in some circumstances components such as data agents 142 and media agents 144, etc.

As shown by the dashed arrowed lines 114 in FIG. 1C, storage manager 140 may communicate with, instruct, and/or control some or all elements of system 100, such as data agents 142 and media agents 144. In this manner, storage manager 140 manages the operation of various hardware and software components in system 100. In certain embodiments, control information originates from storage manager 140 and status as well as index reporting is transmitted to storage manager 140 by the managed components, whereas payload data and metadata are generally communicated between data agents 142 and media agents 144 (or otherwise between client computing device(s) 102 and secondary storage computing device(s) 106), e.g., at the direction of and under the management of storage manager 140. Control information can generally include parameters and instructions for carrying out information management operations, such as, without limitation, instructions to perform a task associated with an operation, timing information specifying when to initiate a task, data path information specifying what components to communicate with or access in carrying out an operation, and the like. In other embodiments, some information management operations are controlled or initiated by other components of system 100 (e.g., by media agents 144 or data agents 142), instead of or in combination with storage manager 140.

According to certain embodiments, storage manager 140 provides one or more of the following functions:

- communicating with data agents 142 and media agents 144, including transmitting instructions, messages, and/or queries, as well as receiving status reports, index information, messages, and/or queries, and responding to same; initiating execution of information management operations;
- initiating restore and recovery operations;
- managing secondary storage devices 108 and inventory/capacity of the same;
- allocating secondary storage devices 108 for secondary copy operations;
- reporting, searching, and/or classification of data in system 100;
- monitoring completion of and status reporting related to information management operations and jobs;
- tracking movement of data within system 100;
- tracking age information relating to secondary copies 116, secondary storage devices 108, comparing the age information against retention guidelines, and initiating data pruning when appropriate;
- tracking logical associations between components in system 100;
- protecting metadata associated with system 100, e.g., in management database 146;
- implementing job management, schedule management, event management, alert management, reporting, job history maintenance, user security management, disaster recovery management, and/or user interfacing for system administrators and/or end users of system 100;
- sending, searching, and/or viewing of log files; and
- implementing operations management functionality.

Storage manager 140 may maintain an associated database 146 (or "storage manager database 146" or "management database 146") of management-related data and information management policies 148. Database 146 is stored in computer memory accessible by storage manager 140. Database 146 may include a management index 150 (or "index 150") or other data structure(s) that may store: logical associations between components of the system; user preferences and/or profiles (e.g., preferences regarding encryption, compression, or deduplication of primary data or secondary copies; preferences regarding the scheduling, type, or other aspects of secondary copy or other operations; mappings of particular information management users or user accounts to certain computing devices or other components, etc.; management tasks; media containerization; other useful data; and/or any combination thereof. For example, storage manager 140 may use index 150 to track logical associations between media agents 144 and secondary storage devices 108 and/or movement of data to/from secondary storage devices 108. For instance, index 150 may store data associating a client computing device 102 with a particular media agent 144 and/or secondary storage device 108, as specified in an information management policy 148.

Administrators and others may configure and initiate certain information management operations on an individual basis. But while this may be acceptable for some recovery operations or other infrequent tasks, it is often not workable for implementing on-going organization-wide data protection and management. Thus, system 100 may utilize information management policies 148 for specifying and executing information management operations on an automated basis. Generally, an information management policy 148 can include a stored data structure or other information source that specifies parameters (e.g., criteria and rules) associated with storage management or other information management operations. Storage manager 140 can process an information management policy 148 and/or index 150 and, based on the results, identify an information management operation to perform, identify the appropriate components in system 100 to be involved in the operation (e.g., client computing devices 102 and corresponding data agents 142, secondary storage computing devices 106 and corresponding media agents 144, etc.), establish connections to those components and/or between those components, and/or instruct and control those components to carry out the operation, in this manner, system 100 can translate stored information into coordinated activity among the various computing devices in system 100.

Management database 146 may maintain information management policies 148 and associated data, although management policies 148 can be stored in computer memory at any appropriate location outside management database 146. For instance, an information management policy 148 such as a storage policy may be stored as metadata in a media agent database 152 or in a secondary storage device 108 (e.g., as an archive copy) for use in restore or other information management operations, depending on the embodiment. Information management policies 148 are described further below. According to certain embodiments, management database 146 comprises a relational database (e.g., an SQL database) for tracking metadata, such as metadata associated with secondary copy operations (e.g., what client computing devices 102 and corresponding subclient data were protected and where the secondary copies are stored and which media agent 144 performed the storage operation(s)). This and other metadata may additionally be stored in other locations, such as at secondary storage computing device 106 or on the secondary storage device 108, allowing data recovery without the use of storage manager 140 in some cases. Thus, management database 146 may comprise data needed to kick off secondary copy operations (e.g., storage policies, schedule policies, etc.), status and reporting information about completed jobs (e.g., status and error reports on yesterday's backup jobs), and additional information sufficient to enable restore and disaster recovery operations (e.g., media agent associations, location indexing, content indexing, etc.).

Storage manager 140 may include a jobs agent 156, a user interface 158, and a management agent 154, all of which may be implemented as interconnected software modules or application programs. These are described further below.

Jobs agent 156 in some embodiments initiates, controls, and/or monitors the status of some or all information management operations previously performed, currently being performed, or scheduled to be performed by system 100. A job is a logical grouping of information management operations such as daily storage operations scheduled for a certain set of subclients (e.g., generating incremental block-level backup copies 116 at a certain time every day for database files in a certain geographical location). Thus, jobs agent 156 may access information management policies 148 (e.g., in management database 146) to determine when, where, and how to initiate/control jobs in system 100.

Storage Manager User Interfaces

User interface 158 may include information processing and display software, such as a graphical user interface (GUI), an application program interface (API), and/or other interactive interface(s) through which users and system processes can retrieve information about the status of information management operations or issue instructions to storage manager 140 and other components. Via user interface 158, users may issue instructions to the components in system 100 regarding performance of secondary copy and recovery operations. For example, a user may modify a schedule concerning the number of pending secondary copy operations. As another example, a user may employ the GUI to view the status of pending secondary copy jobs or to monitor the status of certain components in system 100 (e.g., the amount of capacity left in a storage device). Storage manager 140 may track information that permits it to select, designate, or otherwise identify content indices, deduplication databases, or similar databases or resources or data sets within its information management cell (or another cell) to be searched in response to certain queries. Such queries may be entered by the user by interacting with user interface 158.

Various embodiments of information management system 100 may be configured and/or designed to generate user interface data usable for rendering the various Interactive user interfaces described. The user interface data may be used by system 100 and/or by another system, device, and/or software program (for example, a browser program), to render the interactive user interfaces. The interactive user interfaces may be displayed on, for example, electronic displays (including, for example, touch-enabled displays), consoles, etc., whether direct-connected to storage manager 140 or communicatively coupled remotely, e.g., via an Internet connection. The present disclosure describes various embodiments of interactive and dynamic user interfaces, some of which may be generated by user interface agent 158, and which are the result of significant technological development. The user interfaces described herein may provide improved human-computer interactions, allowing for significant cognitive and ergonomic efficiencies and advantages over previous systems, including reduced mental workloads, improved decision-making, and the like. User interface 158 may operate in a single integrated view or console (not shown). The console may support a reporting capability for generating a variety of reports, which may be tailored to a particular aspect of information management.

User interfaces are not exclusive to storage manager 140 and in some embodiments a user may access information locally from a computing device component of system 100. For example, some information pertaining to installed data agents 142 and associated data streams may be available from client computing device 102. Likewise, some information pertaining to media agents 144 and associated data streams may be available from secondary storage computing device 106.

Storage Manager Management Agent

Management agent 154 can provide storage manager 140 with the ability to communicate with other components within system 100 and/or with other information management cells via network protocols and application programming interfaces (APIs) including, e.g., HTTP, HTTPS, FTP, REST, virtualization software APIs, cloud service provider APIs, and hosted service provider APIs, without limitation. Management agent 154 also allows multiple information management cells to communicate with one another. For example, system 100 in some cases may be one information management cell in a network of multiple cells adjacent to one another or otherwise logically related, e.g., in a WAN or LAN. With this arrangement, the cells may communicate with one another through respective management agents 154. Inter-cell communications and hierarchy is described in greater detail in e.g., U.S. Pat. No. 7,343,453.

Information Management Cell

An "information management cell" (or "storage operation cell" or "cell") may generally include a logical and/or physical grouping of a combination of hardware and software components associated with performing information management operations on electronic data, typically one storage manager 140 and at least one data agent 142 (executing on a client computing device 102) and at least one media agent 144 (executing on a secondary storage computing device 106). For instance, the components shown in FIG. 1C may together form an information management cell. Thus, in some configurations, a system 100 may be referred to as an information management cell or a storage operation cell. A given cell may be identified by the identity of its storage manager 140, which is generally responsible for managing the cell.

Multiple cells may be organized hierarchically, so that cells may inherit properties from hierarchically superior cells or be controlled by other cells in the hierarchy (automatically or otherwise). Alternatively, in some embodiments, cells may inherit or otherwise be associated with information management policies, preferences, information management operational parameters, or other properties or characteristics according to their relative position in a hierarchy of cells. Cells may also be organized hierarchically according to function, geography, architectural considerations, or other factors useful or desirable in performing information management operations. For example, a first cell may represent a geographic segment of an enterprise, such as a Chicago office, and a second cell may represent a different geographic segment, such as a New York City office. Other cells may represent departments within a particular office, e.g., human resources, finance, engineering, etc. Where delineated by function, a first cell may perform one or more first types of information management operations (e.g., one or more first types of secondary copies at a certain frequency), and a second cell may perform one or more second types of information management operations (e.g., one or more second types of secondary copies at a different frequency and under different retention rules). In general, the hierarchical information is maintained by one or more storage managers 140 that manage the respective cells (e.g., in corresponding management database(s) 146).

Data Agents

A variety of different applications 110 can operate on a given client computing device 102, including operating systems, file systems, database applications, e-mail applications, and virtual machines, just to name a few. And, as part of the process of creating and restoring secondary copies 116, the client computing device 102 may be tasked with processing and preparing the primary data 112 generated by these various applications 110, Moreover, the nature of the processing/preparation can differ across application types, e.g., due to inherent structural, state, and formatting differences among applications 110 and/or the operating system of client computing device 102. Each data agent 142 is therefore advantageously configured in some embodiments to assist in the performance of information management operations based on the type of data that is being protected at a client-specific and/or application-specific level.

Data agent 142 is a component of information system 100 and is generally directed by storage manager 140 to participate hi creating or restoring secondary copies 116. Data agent 142 may be a software program (e.g., in the form of a set of executable binary files) that executes on the same client computing device 102 as the associated application 110 that data agent 142 is configured to protect. Data agent 142 is generally responsible for managing, initiating, or otherwise assisting in the performance of information management operations in reference to its associated application(s) 110 and corresponding primary data 112 which is generated/accessed by the particular application(s) 110. For instance, data agent 142 may take part in copying, archiving, migrating, and/or replicating of certain primary data 112 stored in the primary storage device(s) 104. Data agent 142 may receive control information from storage manager 140, such as commands to transfer copies of data objects and/or metadata to one or more media agents 144. Data agent 142 also may compress, deduplicate, and encrypt certain primary data 112, as well as capture application-related metadata before transmitting the processed data to media agent 144. Data agent 142 also may receive instructions from storage manager 140 to restore (or assist in restoring) a secondary copy 116 from secondary storage device 108 to primary storage 104, such that the restored data may be properly accessed by application 110 in a suitable format as though it were primary data 112.

Each data agent 142 may be specialized for a particular application 110. For instance, different individual data agents 142 may be designed to handle Microsoft Exchange data, Lotus Notes data, Microsoft Windows file system data, Microsoft Active Directory Objects data, SQL Server data, SharePoint data, Oracle database data, SAP database data, virtual machines and/or associated data, and other types of data. A file system data agent, for example, may handle data files and/or other file system information. If a client computing device 102 has two or more types of data 112, a specialized data agent 142 may be used for each data type. For example, to backup, migrate, and/or restore all of the data on a Microsoft Exchange server, the client computing device 102 may use: (1) a Microsoft Exchange Mailbox data agent 142 to back up the Exchange mailboxes; (2) a Microsoft Exchange Database data agent 142 to back up the Exchange databases; (3) a Microsoft Exchange Public Folder data agent 142 to back up the Exchange Public Folders; and (4) a Microsoft Windows File System data agent 142 to back up the file system of client computing device 102. In this example, these specialized data agents 142 are treated as four separate data agents 142 even though they operate on the same client computing device 102. Other examples may include archive management data agents such as a migration archiver or a compliance archiver, Quick Recovery® agents, and continuous data replication agents. Application-specific data agents 142 can provide improved performance as compared to generic agents. For instance, because application-specific data agents 142 may only handle data for a single software application, the design, operation, and performance of the data agent 142 can be streamlined. The data agent 142 may therefore execute faster and consume less persistent storage and/or operating memory than data agents designed to generically accommodate multiple different software applications 110.

Each data agent 142 may be configured to access data and/or metadata stored in the primary storage device(s) 104 associated with data agent 142 and its host client computing device 102, and process the data appropriately. For example, during a secondary copy operation, data agent 142 may arrange or assemble the data and metadata into one or more files having a certain format (e.g., a particular backup or archive format) before transferring the file(s) to a media agent 144 or other component. The file(s) may include a list of files or other metadata. In some embodiments, a data agent 142 may be distributed between client computing device 102 and storage manager 140 (and any other intermediate components) or may be deployed from a remote location or its functions approximated by a remote process that performs some or all of the functions of data agent 142. In addition, a data agent 142 may perform some functions provided by media agent 144. Other embodiments may employ one or more generic data agents 142 that can handle and process data from two or more different applications 110, or that can handle and process multiple data types, instead of or in addition to using specialized data agents 142. For example, one generic data agent 142 may be used to back up, migrate and restore Microsoft Exchange Mailbox data and Microsoft Exchange Database data, while another generic data agent may handle Microsoft Exchange Public Folder data and Microsoft Windows File System data.

Media Agents

As noted, off-loading certain responsibilities from client computing devices 102 to intermediate components such as secondary storage computing device(s) 106 and corresponding media agent(s) 144 can provide a number of benefits including improved performance of client computing device 102, faster and more reliable information management operations, and enhanced scalability. In one example, which will be discussed further below, media agent 144 can act as a local cache of recently-copied data and/or metadata stored to secondary storage device(s) 108, thus improving restore capabilities and performance for the cached data.

Media agent 144 is a component of system 100 and is generally directed by storage manager 140 in creating and restoring secondary copies 116. Whereas storage manager 140 generally manages system 100 as a whole, media agent 144 provides a portal to certain secondary storage devices 108, such as by having specialized features for communicating with and accessing certain associated secondary storage device 108. Media agent 144 may be a software program (e.g., in the form of a set of executable binary files) that executes on a secondary storage computing device 106. Media agent 144 generally manages, coordinates, and facilitates the transmission of data between a data agent 142 (executing on client computing device 102) and secondary storage device(s) 108 associated with media agent 144, For instance, other components in the system may interact with media agent 144 to gain access to data stored on associated secondary storage device(s) 108, (e.g., to browse, read, write, modify, delete, or restore data). Moreover, media agents 144 can generate and store information relating to characteristics of the stored data and/or metadata, or can generate and store other types of information that generally provides insight into the contents of the secondary storage devices 108 generally referred to as indexing of the stored secondary copies 116. Each media agent 144 may operate on a dedicated secondary storage computing device 106, while in other embodiments a plurality of media agents 144 may operate on the same secondary storage computing device 106.

A media agent 144 may be associated with a particular secondary storage device 108 if that media agent 144 is capable of one or more of: routing and/or storing data to the particular secondary storage device 108; coordinating the routing and/or storing of data to the particular secondary storage device 108; retrieving data from the particular secondary storage device 108; coordinating the retrieval of data from the particular secondary storage device 108; and modifying and/or deleting data retrieved from the particular secondary storage device 108. Media agent 144 in certain embodiments is physically separate from the associated secondary storage device 108. For instance, a media agent 144 may operate on a secondary storage computing device 106 in a distinct housing, package, and/or location from the associated secondary storage device 108. In one example, a media agent 144 operates on a first server computer and is in communication with a secondary storage device(s) 108 operating in a separate rack-mounted RAID based system.

A media agent 144 associated with a particular secondary storage device 108 may instruct secondary storage device 108 to perform an information management task. For instance, a media agent 144 may instruct a tape library to use a robotic arm or other retrieval means to load or eject a certain storage media, and to subsequently archive, migrate, or retrieve data to or from that media, e.g., for the purpose of restoring data to a client computing device 102. As another example, a secondary storage device 108 may include an array of hard disk drives or solid state drives organized in a RAID configuration, and media agent 144 may forward a logical unit number (LUN) and other appropriate information to the array, which uses the received information to execute the desired secondary copy operation. Media agent 144 may communicate with a secondary storage device 108 via a suitable communications link, such as a SCSI or Fibre Channel link.

Each media agent 144 may maintain an associated media agent database 152. Media agent database 152 may be stored to a disk or other storage device (not shown) that is local to the secondary storage computing device 106 on which media agent 144 executes. In other cases, media agent database 152 is stored separately from the host secondary storage computing device 106. Media agent database 152 can include, among other things, a media agent index 153 (see, e.g., FIG. 1C). In some cases, media agent index 153 does not form a part of and is instead separate from media agent database 152.

Media agent index 153 (or "index 153") may be a data structure associated with the particular media agent 144 that includes information about the stored data associated with the particular media agent and which may be generated in the course of performing a secondary copy operation or a restore. Index 153 provides a fast and efficient mechanism for locating/browsing secondary copies 116 or other data stored in secondary storage devices 108 without having to access secondary storage device 108 to retrieve the information from there. For instance, for each secondary copy 116, index 153 may include metadata such as a list of the data objects (e.g., files/subdirectories, database objects, mailbox objects, etc.), a logical path to the secondary copy 116 on the corresponding secondary storage device 108, location information (e.g., offsets) indicating where the data objects are stored in the secondary storage device 108, when the data objects were created or modified, etc. Thus, index 153 includes metadata associated with the secondary copies 116 that is readily available for use from media agent 144. In some embodiments, some or all of the information in index 153 may instead or additionally be stored along with secondary copies 116 in secondary storage device 108. In some embodiments, a secondary storage device 108 can include sufficient information to enable a "bare metal restore," where the operating system and/or software applications of a failed client computing device 102 or another target may be automatically restored without manually reinstalling individual software packages (including operating systems).

Because index 153 may operate as a cache, it can also be referred to as an "index cache." In such cases, information stored in index cache 153 typically comprises data that reflects certain particulars about relatively recent secondary copy operations. After some triggering event, such as after some time elapses or index cache 153 reaches a particular size, certain portions of index cache 153 may be copied or migrated to secondary storage device 108, e.g., on a least-recently-used basis. This information may be retrieved and uploaded back into index cache 153 or otherwise restored to media agent 144 to facilitate retrieval of data from the secondary storage device(s) 108. In some embodiments, the cached information may include format or containerization information related to archives or other files stored on storage device(s) 108.

In some alternative embodiments media agent 144 generally acts as a coordinator or facilitator of secondary copy operations between client computing devices 102 and secondary storage devices 108, but does not actually write the data to secondary storage device 108. For instance, storage manager 140 (or media agent 144) may instruct a client computing device 102 and secondary storage device 108 to communicate with one another directly. In such a case, client computing device 102 transmits data directly or via one or more intermediary components to secondary storage device 108 according to the received instructions, and vice versa. Media agent 144 may still receive, process, and/or maintain metadata related to the secondary copy operations, i.e., may continue to build and maintain index 153. In these embodiments, payload data can flow through media agent 144 for the purposes of populating index 153, but not for writing to secondary storage device 108. Media agent 144 and/or other components such as storage manager 140 may in some cases incorporate additional functionality, such as data classification, content indexing, deduplication, encryption, compression, and the like. Further details regarding these and other functions are described below.

Distributed, Scalable Architecture

As described, certain functions of system 100 can be distributed amongst various physical and/or logical components. For instance, one or more of storage manager 140, data agents 142, and media agents 144 may operate on computing devices that are physically separate from one another. This architecture can provide a number of benefits. For instance, hardware and software design choices for each distributed component can be targeted to suit its particular function. The secondary computing devices 106 on which media agents 144 operate can be tailored for interaction with associated secondary storage devices 108 and provide fast index cache operation, among other specific tasks. Similarly, client computing device(s) 102 can be selected to effectively service applications 110 in order to efficiently produce and store primary data 112.

Moreover, in some cases, one or more of the individual components of information management system 100 can be distributed to multiple separate computing devices. As one example, for large file systems where the amount of data stored in management database 146 is relatively large, database 146 may be migrated to or may otherwise reside on a specialized database server (e.g., an SQL server) separate from a server that implements the other functions of storage manager 140. This distributed configuration can provide added protection because database 146 can be protected with standard database utilities (e.g., SQL log shipping or database replication) independent from other functions of storage manager 140. Database 146 can be efficiently replicated to a remote site for use in the event of a disaster or other data loss at the primary site. Or database 146 can be replicated to another computing device within the same site, such as to a higher performance machine in the event that a storage manager host computing device can no longer service the needs of a growing system 100.

Figure 1D:
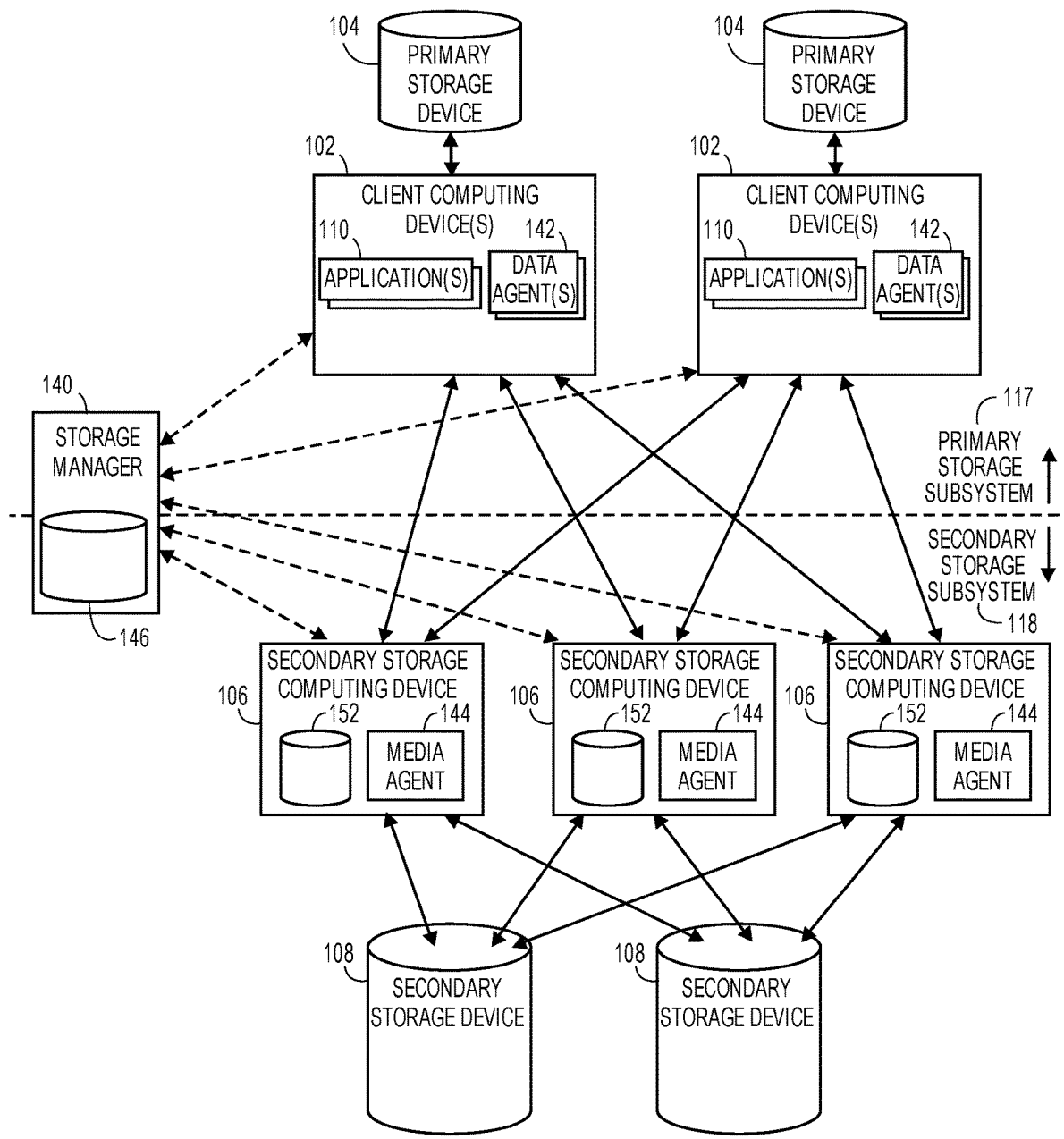
FIG. 1D is a block diagram illustrating a scalable information management system.

The distributed architecture also provides scalability and efficient component utilization. FIG. 1D shows an embodiment of information management system 100 including a plurality of client computing devices 102 and associated data agents 142 as well as a plurality of secondary storage computing devices 106 and associated media agents 144. Additional components can be added or subtracted based on the evolving needs of system 100. For instance, depending on where bottlenecks are identified, administrators can add additional client computing devices 102, secondary storage computing devices 106, and/or secondary storage devices 108. Moreover, where multiple fungible components are available, load balancing can be implemented to dynamically address identified bottlenecks. As an example, storage manager 140 may dynamically select which media agents 144 and/or secondary storage devices 108 to use for storage operations based on a processing load analysis of media agents 144 and/or secondary storage devices 108, respectively.

Where system 100 includes multiple media agents 144 (see, e.g., FIG. 1D), a first media agent 144 may provide failover functionality for a second failed media agent 144, In addition, media agents 144 can be dynamically selected to provide load balancing. Each client computing device 102 can communicate with, among other components, any of the media agents 144, e.g., as directed by storage manager 140, Each media agent 144 may also communicate with, among other components, any of secondary storage devices 108, e.g., as directed by storage manager 140. Thus, operations can be routed to secondary storage devices 108 in a dynamic and highly flexible manner, to provide load balancing, failover, etc. Further examples of scalable systems capable of dynamic storage operations, load balancing, and failover are provided in U.S. Pat. No. 7,246,207.

While distributing functionality amongst multiple computing devices can have certain advantages, in other contexts it can be beneficial to consolidate functionality on the same computing device. In alternative configurations, certain components may reside and execute on the same computing device. As such, in other embodiments, one or more of the components shown in FIG. 1C may be implemented on the same computing device. In one configuration, a storage manager 140, one or more data agents 142, and/or one or more media agents 144 are all implemented on the same computing device. In other embodiments, one or more data agents 142 and one or more media agents 144 are implemented on the same computing device, while storage manager 140 is implemented on a separate computing device, etc. without limitation.

Exemplary Types of Information Management Operations Including Storage Operations In order to protect and leverage stored data, system 100 can be configured to perform a variety of information management operations, which may also be referred to in some cases as storage management operations or storage operations. These operations can generally include (i) data movement operations, (ii) processing and data manipulation operations, and (iii) analysis, reporting, and management operations.

Data Movement Operations, Including Secondary Copy Operations

Data movement operations are generally storage operations that involve the copying or migration of data between different locations in system 100. For example, data movement operations can include operations in which stored data is copied, migrated, or otherwise transferred from one or more first storage devices to one or more second storage devices, such as from primary storage device(s) 104 to secondary storage device(s) 108, from secondary storage device(s) 108 to different secondary storage device(s) 108, from secondary storage devices 108 to primary storage devices 104, or from primary storage device(s) 104 to different primary storage device(s) 104, or in some cases within the same primary storage device 104 such as within a storage array.

Data movement operations can include by way of example, backup operations, archive operations, information lifecycle management operations such as hierarchical storage management operations, replication operations (e.g., continuous data replication), snapshot operations, deduplication or single-instancing operations, auxiliary copy operations, disaster-recovery copy operations, and the like. As will be discussed, some of these operations do not necessarily create distinct copies, Nonetheless, some or all of these operations are generally referred to as "secondary copy operations" for simplicity, because they involve secondary copies. Data movement also comprises restoring secondary copies.

Backup Operations

A backup operation creates a copy of a version of primary data 112 at a particular point in time (e.g., one or more files or other data units). Each subsequent backup copy 116 (which is a form of secondary copy 116) may be maintained independently of the first. A backup generally involves maintaining a version of the copied primary data 112 as well as backup copies 116, Further, a backup copy in some embodiments is generally stored in a form that is different from the native format, e.g., a backup format. This contrasts to the version in primary data 112 which may instead be stored in a format native to the source application(s) 110. In various cases, backup copies can be stored in a format in which the data is compressed, encrypted, deduplicated, and/or otherwise modified from the original native application format. For example, a backup copy may be stored in a compressed backup format that facilitates efficient long-term storage, Backup copies 116 can have relatively long retention periods as compared to primary data 112, which is generally highly changeable. Backup copies 116 may be stored on media with slower retrieval times than primary storage device 104. Some backup copies may have shorter retention periods than some other types of secondary copies 116, such as archive copies (described below). Backups may be stored at an offsite location.

Backup operations can include full backups, differential backups, incremental backups, "synthetic full" backups, and/or creating a "reference copy." A full backup (or "standard full backup") in some embodiments is generally a complete image of the data to be protected. However, because full backup copies can consume a relatively large amount of storage, it can be useful to use a full backup copy as a baseline and only store changes relative to the full backup copy afterwards.

A differential backup operation (or cumulative incremental backup operation) tracks and stores changes that occurred since the last full backup. Differential backups can grow quickly in size, but can restore relatively efficiently because a restore can be completed in some cases using only the full backup copy and the latest differential copy.

An incremental backup operation generally tracks and stores changes since the most recent backup copy of any type, which can greatly reduce storage utilization. In some cases, however, restoring can be lengthy compared to full or differential backups because completing a restore operation may involve accessing a full backup in addition to multiple incremental backups.

Synthetic full backups generally consolidate data without directly backing up data from the client computing device. A synthetic full backup is created from the most recent full backup (i.e., standard or synthetic) and subsequent incremental and/or differential backups. The resulting synthetic full backup is identical to what would have been created had the last backup for the subclient been a standard full backup. Unlike standard full, incremental, and differential backups, however, a synthetic full backup does not actually transfer data from primary storage to the backup media, because it operates as a backup consolidator. A synthetic full backup extracts the index data of each participating subclient. Using this index data and the previously backed up user data images, it builds new full backup images (e.g., bitmaps), one for each subclient. The new backup images consolidate the index and user data stored in the related incremental, differential, and previous full backups into a synthetic backup file that fully represents the subclient (e.g., via pointers) but does not comprise all its constituent data.

Any of the above types of backup operations can be at the volume level, file level, or block level. Volume level backup operations generally involve copying of a data volume (e.g., a logical disk or partition) as a whole. In a file-level backup, information management system 100 generally tracks changes to individual files and includes copies of files in the backup copy. For block-level backups, files are broken into constituent blocks, and changes are tracked at the block level. Upon restore, system 100 reassembles the blocks into files in a transparent fashion. Far less data may actually be transferred and copied to secondary storage devices 108 during a file-level copy than a volume-level copy. Likewise, a block-level copy may transfer less data than a file-level copy, resulting in faster execution. However, restoring a relatively higher-granularity copy can result in longer restore times. For instance, when restoring a block-level copy, the process of locating and retrieving constituent blocks can sometimes take longer than restoring file-level backups.

A reference copy may comprise copy(ies) of selected objects from backed up data, typically to help organize data by keeping contextual information from multiple sources together, and/or help retain specific data for a longer period of time, such as for legal hold needs. A reference copy generally maintains data integrity, and when the data is restored, it may be viewed in the same format as the source data. In some embodiments, a reference copy is based on a specialized client, individual subclient and associated information management policies (e.g., storage policy, retention policy, etc.) that are administered within system 100.

Archive Operations

Because backup operations generally involve maintaining a version of the copied primary data 112 and also maintaining backup copies in secondary storage device(s) 108, they can consume significant storage capacity, To reduce storage consumption, an archive operation according to certain embodiments creates an archive copy 116 by both copying and removing source data. Or, seen another way, archive operations can involve moving some or all of the source data to the archive destination. Thus, data satisfying criteria for removal (e.g., data of a threshold age or size) may be removed from source storage. The source data may be primary data 112 or a secondary copy 116, depending on the situation. As with backup copies, archive copies can be stored in a format in which the data is compressed, encrypted, deduplicated, and/or otherwise modified from the format of the original application or source copy. In addition, archive copies may be retained for relatively long periods of time (e.g., years) and, in some cases are never deleted. In certain embodiments, archive copies may be made and kept for extended periods in order to meet compliance regulations.

Archiving can also serve the purpose of freeing up space in primary storage device(s) 104 and easing the demand on computational resources on client computing device 102, Similarly, when a secondary copy 116 is archived, the archive copy can therefore serve the purpose of freeing up space in the source secondary storage device(s) 108. Examples of data archiving operations are provided in U.S. Pat. No. 7,107,298.

Snapshot of Operations

Snapshot operations can provide a relatively lightweight, efficient mechanism for protecting data, From an end-user viewpoint, a snapshot may be thought of as an "instant" image of primary data 112 at a given point in time, and may include state and/or status information relative to an application 110 that creates/manages primary data 112. In one embodiment, a snapshot may generally capture the directory structure of an object in primary data 112 such as a file or volume or other data set at a particular moment in time and may also preserve file attributes and contents. A snapshot in some cases is created relatively quickly, e.g., substantially instantly, using a minimum amount of file space, but may still function as a conventional file system backup.

A "hardware snapshot" (or "hardware-based snapshot") operation occurs where a target storage device (e.g., a primary storage device 104 or a secondary storage device 108) performs the snapshot operation in a self-contained fashion, substantially independently, using hardware, firmware and/or software operating on the storage device itself. For instance, the storage device may perform snapshot operations generally without intervention or oversight from any of the other components of the system 100, e.g., a storage array may generate an "array-created" hardware snapshot and may also manage its storage, integrity, versioning, etc. In this manner, hardware snapshots can off-load other components of system 100 from snapshot processing. An array may receive a request from another component to take a snapshot and then proceed to execute the "hardware snapshot" operations autonomously, preferably reporting success to the requesting component.

A "software snapshot" (or "software-based snapshot") operation, on the other hand, occurs where a component in system 100 (e.g., client computing device 102, etc.) implements a software layer that manages the snapshot operation via interaction with the target storage device. For instance, the component executing the snapshot management software layer may derive a set of pointers and/or data that represents the snapshot. The snapshot management software layer may then transmit the same to the target storage device, along with appropriate instructions for writing the snapshot. One example of a software snapshot product is Microsoft Volume Snapshot Service (VSS), which is part of the Microsoft Windows operating system.

Some types of snapshots do not actually create another physical copy of all the data as it existed at the particular point in time, but may simply create pointers that map files and directories to specific memory locations (e.g., to specific disk blocks) where the data resides as it existed at the particular point in time. For example, a snapshot copy may include a set of pointers derived from the file system or from an application. In some other cases, the snapshot may be created at the block-level, such that creation of the snapshot occurs without awareness of the file system. Each pointer points to a respective stored data block, so that collectively, the set of pointers reflect the storage location and state of the data object (e.g., file(s) or volume(s) or data set(s)) at the point in time when the snapshot copy was created.

An initial snapshot may use only a small amount of disk space needed to record a mapping or other data structure representing or otherwise tracking the blocks that correspond to the current state of the file system. Additional disk space is usually required only when files and directories change later on. Furthermore, when files change, typically only the pointers which map to blocks are copied, not the blocks themselves. For example, for "copy-on-write" snapshots, when a block changes in primary storage, the block is copied to secondary storage or cached in primary storage before the block is overwritten in primary storage, and the pointer to that block is changed to reflect the new location of that block. The snapshot mapping of file system data may also be updated to reflect the changed block(s) at that particular point in time. In some other cases, a snapshot includes a full physical copy of all or substantially all of the data represented by the snapshot. Further examples of snapshot operations are provided in U.S. Pat. No. 7,529,782. A snapshot copy in many cases can be made quickly and without significantly impacting primary computing resources because large amounts of data need not be copied or moved. In some embodiments, a snapshot may exist as a virtual file system, parallel to the actual file system. Users in some cases gain read-only access to the record of files and directories of the snapshot. By electing to restore primary data 112 from a snapshot taken at a given point in time, users may also return the current file system to the state of the file system that existed when the snapshot was taken.

Replication Operations

Replication is another type of secondary copy operation. Some types of secondary copies 116 periodically capture images of primary data 112 at particular points in time (e.g., backups, archives, and snapshots). However, it can also be useful for recovery purposes to protect primary data 112 in a more continuous fashion, by replicating primary data 112 substantially as changes occur. In some cases a replication copy can be a mirror copy, for instance, where changes made to primary data 112 are mirrored or substantially immediately copied to another location (e.g., to secondary storage device(s) 108). By copying each write operation to the replication copy, two storage systems are kept synchronized or substantially synchronized so that they are virtually identical at approximately the same time. Where entire disk volumes are mirrored, however, mirroring can require significant amount of storage space and utilizes a large amount of processing resources.

According to some embodiments, secondary copy operations are performed on replicated data that represents a recoverable state, or "known good state" of a particular application running on the source system. For instance, in certain embodiments, known good replication copies may be viewed as copies of primary data 112, This feature allows the system to directly access, copy, restore, back up, or otherwise manipulate the replication copies as if they were the "live" primary data 112, This can reduce access time, storage utilization, and impact on source applications 110, among other benefits. Based on known good state information, system 100 can replicate sections of application data that represent a recoverable state rather than rote copying of blocks of data. Examples of replication operations (e.g., continuous data replication) are provided in U.S. Pat. No. 7,617,262.

Deduplication/Single-Instancing Operations

Deduplication or single-instance storage is useful to reduce the amount of non-primary data. For instance, some or all of the above-described secondary copy operations can involve deduplication in some fashion. New data is read, broken down into data portions of a selected granularity (e.g., sub-file level blocks, files, etc.), compared with corresponding portions that are already in secondary storage, and only new/changed portions are stored. Portions that already exist are represented as pointers to the already-stored data. Thus, a deduplicated secondary copy 116 may comprise actual data portions copied from primary data 112 and may further comprise pointers to already-stored data, which is generally more storage-efficient than a full copy.

In order to streamline the comparison process, system 100 may calculate and/or store signatures (e.g., hashes or cryptographically unique IDs) corresponding to the individual source data portions and compare the signatures to already-stored data signatures, instead of comparing entire data portions. In some cases, only a single instance of each data portion is stored, and deduplication operations may therefore be referred to interchangeably as "single-instancing" operations. Depending on the implementation, however, deduplication operations can store more than one instance of certain data portions, yet still significantly reduce stored-data redundancy. Depending on the embodiment, deduplication portions such as data blocks can be of fixed or variable length. Using variable length blocks can enhance deduplication by responding to changes in the data stream, but can involve more complex processing. In some cases, system 100 utilizes a technique for dynamically aligning deduplication blocks based on changing content in the data stream, as described in U.S. Pat. No. 8,364,652.

System 100 can deduplicate in a variety of manners at a variety of locations. For instance, in some embodiments, system 100 implements "target-side" deduplication by deduplicating data at the media agent 144 after being received from data agent 142. In some such cases, media agents 144 are generally configured to manage the deduplication process. For instance, one or more of the media agents 144 maintain a corresponding deduplication database that stores deduplication information (e.g., datablock signatures). Examples of such a configuration are provided in U.S. Pat. No. 9,020,900, Instead of or in combination with "target-side" deduplication, "source-side" (or "client-side") deduplication can also be performed, e.g., to reduce the amount of data to be transmitted by data agent 142 to media agent 144. Storage manager 140 may communicate with other components within system 100 via network protocols and cloud service provider APIs to facilitate cloud-based deduplication/single instancing, as exemplified in U.S. Pat. No. 8,954,446, Some other deduplication/single instancing techniques are described in U.S. Pat. Pub. No. 2006/0224846 and in U.S. Pat. No. 9,098,495.

Information Lifecycle Management and Hierarchical Storage Management

In some embodiments, files and other data over their lifetime move from more expensive quick-access storage to less expensive slower-access storage. Operations associated with moving data through various tiers of storage are sometimes referred to as information lifecycle management (ILM) operations.

One type of IL M operation is a hierarchical storage management (HSM) operation, which generally automatically moves data between classes of storage devices, such as from high-cost to low-cost storage devices. For instance, an HSM operation may involve movement of data from primary storage devices 104 to secondary storage devices 108, or between tiers of secondary storage devices 108. With each tier, the storage devices may be progressively cheaper, have relatively slower access/restore times, etc. For example, movement of data between tiers may occur as data becomes less important over time. In some embodiments, an HSM operation is similar to archiving in that creating an HSM copy may (though not always) involve deleting some of the source data, e.g., according to one or more criteria related to the source data. For example, an HSM copy may include primary data 112 or a secondary copy 116 that exceeds a given size threshold or a given age threshold. Often, and unlike some types of archive copies, HSM data that is removed or aged from the source is replaced by a logical reference pointer or stub. The reference pointer or stub can be stored in the primary storage device 104 or other source storage device, such as a secondary storage device 108 to replace the deleted source data and to point to or otherwise indicate the new location in (another) secondary storage device 108.

For example, files are generally moved between higher and lower cost storage depending on how often the files are accessed. When a user requests access to HSM data that has been removed or migrated, system 100 uses the stub to locate the data and may make recovery of the data appear transparent, even though the HSM data may be stored at a location different from other source data. In this manner, the data appears to the user (e.g., in file system browsing windows and the like) as if it still resides in the source location (e.g., in a primary storage device 104). The stub may include metadata associated with the corresponding data, so that a file system and/or application can provide some information about the data object and/or a limited-functionality version (e.g., a preview) of the data object.

An HSM copy may be stored in a format other than the native application format (e.g., compressed, encrypted, deduplicated, and/or otherwise modified). In some cases, copies which involve the removal of data from source storage and the maintenance of stub or other logical reference information on source storage may be referred to generally as "on-line archive copies." On the other hand, copies which involve the removal of data from source storage without the maintenance of stub or other logical reference information on source storage may be referred to as "off-line archive copies." Examples of HSM and ILM techniques are provided in U.S. Pat. No. 7,343,453, Auxiliary Copy Operations An auxiliary copy is generally a copy of an existing secondary copy 116. For instance, an initial secondary copy 116 may be derived from primary data 112 or from data residing in secondary storage subsystem 118, whereas an auxiliary copy is generated from the initial secondary copy 116. Auxiliary copies provide additional standby copies of data and may reside on different secondary storage devices 108 than the initial secondary copies 116. Thus, auxiliary copies can be used for recovery purposes if initial secondary copies 116 become unavailable. Exemplary auxiliary copy techniques are described in further detail in U.S. Pat. No. 8,230,195.

Disaster-Recovery Copy Operations

System 100 may also make and retain disaster recovery copies, often as secondary, high-availability disk copies. System 100 may create secondary copies and store them at disaster recovery locations using auxiliary copy or replication operations, such as continuous data replication technologies. Depending on the particular data protection goals, disaster recovery locations can be remote from the client computing devices 102 and primary storage devices 104, remote from some or all of the secondary storage devices 108, or both.

Data Manipulation, Including Encryption and Compression

Data manipulation and processing may include encryption and compression as well as integrity marking and checking, formatting for transmission, formatting for storage, etc. Data may be manipulated "client-side" by data agent 142 as well as "target-side" by media agent 144 in the course of creating secondary copy 116, or conversely in the course of restoring data from secondary to primary.

Encryption Operations

System 100 in some cases is configured to process data (e.g., files or other data objects, primary data 112, secondary copies 116, etc.), according to an appropriate encryption algorithm (e.g., Blowfish, Advanced Encryption Standard (AES), Triple Data Encryption Standard (3-DES), etc.) to limit access and provide data security. System 100 in some cases encrypts the data at the client level, such that client computing devices 102 (e.g., data agents 142) encrypt the data prior to transferring it to other components, e.g., before sending the data to media agents 144 during a secondary copy operation. In such cases, client computing device 102 may maintain or have access to an encryption key or passphrase for decrypting the data upon restore, Encryption can also occur when media agent 144 creates auxiliary copies or archive copies. Encryption may be applied in creating a secondary copy 116 of a previously unencrypted secondary copy 116, without limitation. In further embodiments, secondary storage devices 108 can implement built-in, high performance hardware-based encryption.

Compression Operations

Similar to encryption, system 100 may also or alternatively compress data in the course of generating a secondary copy 116. Compression encodes information such that fewer bits are needed to represent the information as compared to the original representation. Compression techniques are well known in the art. Compression operations may apply one or more data compression algorithms. Compression may be applied in creating a secondary copy 116 of a previously uncompressed secondary copy, e.g., when making archive copies or disaster recovery copies. The use of compression may result in metadata that specifies the nature of the compression, so that data may be uncompressed on restore if appropriate.

Data Analysis, Report, and Management Operations

Data analysis, reporting, and management operations can differ from data movement operations in that they do not necessarily involve copying, migration or other transfer of data between different locations in the system. For instance, data analysis operations may involve processing (e.g., offline processing) or modification of already stored primary data 112 and/or secondary copies 116. However, in some embodiments data analysis operations are performed in conjunction with data movement operations. Some data analysis operations include content indexing operations and classification operations which can be useful in leveraging data under management to enhance search and other features.

Classification Operations/Content Indexing

In some embodiments, information management system 100 analyzes and indexes characteristics, content, and metadata associated with primary data 112 ("online content indexing") and/or secondary copies 116 ("off-line content indexing"). Content indexing can identify files or other data objects based on content (e.g., user-defined keywords or phrases, other keywords/phrases that are not defined by a user, etc.), and/or metadata (e.g., email metadata such as "to," "from," "cc," "bcc," attachment name, received time, etc.). Content indexes may be searched and search results may be restored.

System 100 generally organizes and catalogues the results into a content index, which may be stored within media agent database 152, for example. The content index can also include the storage locations of or pointer references to indexed data in primary data 112 and/or secondary copies 116. Results may also be stored elsewhere in system 100 (e.g., in primary storage device 104 or in secondary storage device 108), Such content index data provides storage manager 140 or other components with an efficient mechanism for locating primary data 112 and/or secondary copies 116 of data objects that match particular criteria, thus greatly increasing the search speed capability of system 100. For instance, search criteria can be specified by a user through user interface 158 of storage manager 140. Moreover, when system 100 analyzes data and/or metadata in secondary copies 116 to create an "off-line content index," this operation has no significant impact on the performance of client computing devices 102 and thus does not take a toll on the production environment. Examples of content indexing techniques are provided in U.S. Pat. No. 8,170,995.

One or more components, such as a content index engine, can be configured to scan data and/or associated metadata for classification purposes to populate a database (or other data structure) of information, which can be referred to as a "data classification database" or a "metabase." Depending on the embodiment, the data classification database(s) can be organized in a variety of different ways, including centralization, logical sub-divisions, and/or physical sub-divisions. For instance, one or more data classification databases may be associated with different subsystems or tiers within system 100. As an example, there may be a first metabase associated with primary storage subsystem 117 and a second metabase associated with secondary storage subsystem 118. In other cases, metabase(s) may be associated with individual components, e.g., client computing devices 102 and/or media agents 144, In some embodiments, a data classification database may reside as one or more data structures within management database 146, may be otherwise associated with storage manager 140, and/or may reside as a separate component. In some cases, metabase(s) may be included in separate database(s) and/or on separate storage device(s) from primary data 112 and/or secondary copies 116, such that operations related to the metabase(s) do not significantly impact performance on other components of system 100. In other cases, metabase(s) may be stored along with primary data 112 and/or secondary copies 116. Files or other data objects can be associated with identifiers (e.g., tag entries, etc.) to facilitate searches of stored data objects. Among a number of other benefits, the metabase can also allow efficient, automatic identification of files or other data objects to associate with secondary copy or other information management operations. For instance, a metabase can dramatically improve the speed with which system 100 can search through and identify data as compared to other approaches that involve scanning an entire file system. Examples of metabases and data classification operations are provided in U.S. Pat. Nos. 7,734,669 and 7,747,579.

Management and Reporting Operations

Certain embodiments leverage the integrated ubiquitous nature of system 100 to provide useful system-wide management and reporting. Operations management can generally include monitoring and managing the health and performance of system 100 by, without limitation, performing error tracking, generating granular storage/performance metrics (e.g., job success/failure information, deduplication efficiency, etc.), generating storage modeling and costing information, and the like. As an example, storage manager 140 or another component in system 100 may analyze traffic patterns and suggest and/or automatically route data to minimize congestion. In some embodiments, the system can generate predictions relating to storage operations or storage operation information. Such predictions, which may be based on a trending analysis, may predict various network operations or resource usage, such as network traffic levels, storage media use, use of bandwidth of communication links, use of media agent components, etc. Further examples of traffic analysis, trend analysis, prediction generation, and the like are described in U.S. Pat. No. 7,343,453.

In some configurations having a hierarchy of storage operation cells, a master storage manager 140 may track the status of subordinate cells, such as the status of jobs, system components, system resources, and other items, by communicating with storage managers 140 (or other components) in the respective storage operation cells. Moreover, the master storage manager 140 may also track status by receiving periodic status updates from the storage managers 140 (or other components) in the respective cells regarding jobs, system components, system resources, and other items. In some embodiments, a master storage manager 140 may store status information and other information regarding its associated storage operation cells and other system information in its management database 146 and/or index 150 (or in another location). The master storage manager 140 or other component may also determine whether certain storage-related or other criteria are satisfied, and may perform an action or trigger event (e.g., data migration) in response to the criteria being satisfied, such as where a storage threshold is met for a particular volume, or where inadequate protection exists for certain data. For instance, data from one or more storage operation cells is used to dynamically and automatically mitigate recognized risks, and/or to advise users of risks or suggest actions to mitigate these risks. For example, an information management policy may specify certain requirements (e.g., that a storage device should maintain a certain amount of free space, that secondary copies should occur at a particular interval, that data should be aged and migrated to other storage after a particular period, that data on a secondary volume should always have a certain level of availability and be restorable within a given time period, that data on a secondary volume may be mirrored or otherwise migrated to a specified number of other volumes, etc.). If a risk condition or other criterion is triggered, the system may notify the user of these conditions and may suggest (or automatically implement) a mitigation action to address the risk. For example, the system may indicate that data from a primary copy 112 should be migrated to a secondary storage device 108 to free up space on primary storage device 104. Examples of the use of risk factors and other triggering criteria are described in U.S. Pat. No. 7,343,453.

In some embodiments, system 100 may also determine whether a metric or other indication satisfies particular storage criteria sufficient to perform an action. For example, a storage policy or other definition might indicate that a storage manager 140 should initiate a particular action if a storage metric or other indication drops below or otherwise fails to satisfy specified criteria such as a threshold of data protection. In some embodiments, risk factors may be quantified into certain measurable service or risk levels. For example, certain applications and associated data may be considered to be more important relative to other data and services. Financial compliance data, for example, may be of greater importance than marketing materials, etc. Network administrators may assign priority values or "weights" to certain data and/or applications corresponding to the relative importance. The level of compliance of secondary copy operations specified for these applications may also be assigned a certain value. Thus, the health, impact, and overall importance of a service may be determined, such as by measuring the compliance value and calculating the product of the priority value and the compliance value to determine the "service level" and comparing it to certain operational thresholds to determine whether it is acceptable. Further examples of the service level determination are provided in U.S. Pat. No. 7,343,453.

System 100 may additionally calculate data costing and data availability associated with information management operation cells. For instance, data received from a cell may be used in conjunction with hardware-related information and other information about system elements to determine the cost of storage and/or the availability of particular data. Exemplary information generated could include how fast a particular department is using up available storage space, how long data would take to recover over a particular pathway from a particular secondary storage device, costs over time, etc. Moreover, in some embodiments, such information may be used to determine or predict the overall cost associated with the storage of certain information. The cost associated with hosting a certain application may be based, at least in part, on the type of media on which the data resides, for example. Storage devices may be assigned to a particular cost categories, for example. Further examples of costing techniques are described in U.S. Pat. No. 7,343,453.

Any of the above types of information (e.g., information related to trending, predictions, job, cell or component status, risk, service level, costing, etc.) can generally be provided to users via user interface 158 in a single integrated view or console (not shown). Report types may include: scheduling, event management, media management and data aging. Available reports may also include backup history, data aging history, auxiliary copy history, job history, library and drive, media in library, restore history, and storage policy, etc., without limitation. Such reports may be specified and created at a certain point in time as a system analysis, forecasting, or provisioning tool. Integrated reports may also be generated that illustrate storage and performance metrics, risks and storage costing information. Moreover, users may create their own reports based on specific needs. User interface 158 can include an option to graphically depict the various components in the system using appropriate icons. As one example, user interface 158 may provide a graphical depiction of primary storage devices 104, secondary storage devices 108, data agents 142 and/or media agents 144, and their relationship to one another in system 100.

In general, the operations management functionality of system 100 can facilitate planning and decision-making. For example, in some embodiments, a user may view the status of some or all jobs as well as the status of each component of information management system 100. Users may then plan and make decisions based on this data. For instance, a user may view high-level information regarding secondary copy operations for system 100, such as job status, component status, resource status (e.g., communication pathways, etc.), and other information. The user may also drill down or use other means to obtain more detailed information regarding a particular component, job, or the like. Further examples are provided in U.S. Pat. No. 7,343,453.

System 100 can also be configured to perform system-wide e-discovery operations in some embodiments. In general, e-discovery operations provide a unified collection and search capability for data in the system, such as data stored in secondary storage devices 108 (e.g., backups, archives, or other secondary copies 116). For example, system 100 may construct and maintain a virtual repository for data stored in system 100 that is integrated across source applications 110, different storage device types, etc. According to some embodiments, e-discovery utilizes other techniques described herein, such as data classification and/or content indexing.

Information Management Policies

An information management policy 148 can include a data structure or other information source that specifies a set of parameters (e.g., criteria and rues) associated with secondary copy and/or other information management operations.

One type of information management policy 148 is a "storage policy." According to certain embodiments, a storage policy generally comprises a data structure or other information source that defines (or includes information sufficient to determine) a set of preferences or other criteria for performing information management operations. Storage policies can include one or more of the following: (1) what data will be associated with the storage policy, e.g., subclient; (2) a destination to which the data will be stored; (3) datapath information specifying how the data will be communicated to the destination; (4) the type of secondary copy operation to be performed; and (5) retention information specifying how long the data will be retained at the destination (see, e.g., FIG. 1E). Data associated with a storage policy can be logically organized into subclients, which may represent primary data 112 and/or secondary copies 116. A subclient may represent static or dynamic associations of portions of a data volume. Subclients may represent mutually exclusive portions. Thus, in certain embodiments, a portion of data may be given a label and the association is stored as a static entity in an index, database or other storage location. Subclients may also be used as an effective administrative scheme of organizing data according to data type, department within the enterprise, storage preferences, or the like. Depending on the configuration, subclients can correspond to files, folders, virtual machines, databases, etc. In one exemplary scenario, an administrator may find it preferable to separate e-mail data from financial data using two different subclients.

A storage policy can define where data is stored by specifying a target or destination storage device (or group of storage devices). For instance, where the secondary storage device 108 includes a group of disk libraries, the storage policy may specify a particular disk library for storing the subclients associated with the policy. As another example, where the secondary storage devices 108 include one or more tape libraries, the storage policy may specify a particular tape library for storing the subclients associated with the storage policy, and may also specify a drive pool and a tape pool defining a group of tape drives and a group of tapes, respectively, for use in storing the subclient data. While information in the storage policy can be statically assigned in some cases, some or all of the information in the storage policy can also be dynamically determined based on criteria set forth in the storage policy. For instance, based on such criteria, a particular destination storage device(s) or other parameter of the storage policy may be determined based on characteristics associated with the data involved in a particular secondary copy operation, device availability (e.g., availability of a secondary storage device 108 or a media agent 144), network status and conditions (e.g., identified bottlenecks), user credentials, and the like.

Datapath information can also be included in the storage policy. For instance, the storage policy may specify network pathways and components to utilize when moving the data to the destination storage device(s). In some embodiments, the storage policy specifies one or more media agents 144 for conveying data associated with the storage policy between the source and destination. A storage policy can also specify the type(s) of associated operations, such as backup, archive, snapshot, auxiliary copy, or the like. Furthermore, retention parameters can specify how long the resulting secondary copies 116 will be kept (e.g., a number of days, months, years, etc.), perhaps depending on organizational needs and/or compliance criteria.

When adding a new client computing device 102, administrators can manually configure information management policies 148 and/or other settings, e.g., via user interface 158. However, this can be an involved process resulting in delays, and it may be desirable to begin data protection operations quickly, without awaiting human intervention. Thus, in some embodiments, system 100 automatically applies a default configuration to client computing device 102. As one example, when one or more data agent(s) 142 are installed on a client computing device 102, the installation script may register the client computing device 102 with storage manager 140, which in turn applies the default configuration to the new client computing device 102. In this manner, data protection operations can begin substantially immediately. The default configuration can include a default storage policy, for example, and can specify any appropriate information sufficient to begin data protection operations. This can include a type of data protection operation, scheduling information, a target secondary storage device 108, data path information (e.g., a particular media agent 144), and the like.

Another type of information management policy 148 is a "scheduling policy," which specifies when and how often to perform operations. Scheduling parameters may specify with what frequency (e.g., hourly, weekly, daily, event-based, etc.) or under what triggering conditions secondary copy or other information management operations are to take place. Scheduling policies in some cases are associated with particular components, such as a subclient, client computing device 102, and the like.

Another type of information management policy 148 is an "audit policy" (or "security policy"), which comprises preferences, rules and/or criteria that protect sensitive data in system 100. For example, an audit policy may define "sensitive objects" which are files or data objects that contain particular keywords (e.g., "confidential," or "privileged") and/or are associated with particular keywords (e.g., in metadata) or particular flags (e.g., in metadata identifying a document or email as personal, confidential, etc.). An audit policy may further specify rules for handling sensitive objects. As an example, an audit policy may require that a reviewer approve the transfer of any sensitive objects to a cloud storage site, and that if approval is denied for a particular sensitive object, the sensitive object should be transferred to a local primary storage device 104 instead. To facilitate this approval, the audit policy may further specify how a secondary storage computing device 10$ or other system component should notify a reviewer that a sensitive object is slated for transfer.

Another type of information management policy 148 is a "provisioning policy," which can include preferences, priorities, rules, and/or criteria that specify how client computing devices 102 (or groups thereof) may utilize system resources, such as available storage on cloud storage and/or network bandwidth. A provisioning policy specifies, for example, data quotas for particular client computing devices 102 (e.g., a number of gigabytes that can be stored monthly, quarterly or annually). Storage manager 140 or other components may enforce the provisioning policy. For instance, media agents 144 may enforce the policy when transferring data to secondary storage devices 108. If a client computing device 102 exceeds a quota, a budget for the client computing device 102 (or associated department) may be adjusted accordingly or an alert may trigger.

While the above types of information management policies 148 are described as separate policies, one or more of these can be generally combined into a single information management policy 148. For instance, a storage policy may also include or otherwise be associated with one or more scheduling, audit, or provisioning policies or operational parameters thereof. Moreover, while storage policies are typically associated with moving and storing data, other policies may be associated with other types of information management operations. The following is a non-exhaustive list of items that information management policies 148 may specify:

- schedules or other timing information, e.g., specifying when and/or how often to perform information management operations;
- the type of secondary copy 116 and/or copy format (e.g., snapshot, backup, archive, HSM, etc.);
- a location or a class or quality of storage for storing secondary copies 116 (e.g., one or more particular secondary storage devices 108);
- preferences regarding whether and how to encrypt, compress, deduplicate, or otherwise modify or transform secondary copies 116;
- which system components and/or network pathways (e.g., preferred media agents 144) should be used to perform secondary storage operations;
- resource allocation among different computing devices or other system components used in performing information management operations (e.g., bandwidth allocation, available storage capacity, etc.);
- whether and how to synchronize or otherwise distribute files or other data objects across multiple computing devices or hosted services; and
- retention information specifying the length of time primary data 112 and/or secondary copies 116 should be retained, e.g., in a particular class or tier of storage devices, or within the system 100.

Information management policies 148 can additionally specify or depend on historical or current criteria that may be used to determine which rules to apply to a particular data object, system component, or information management operation, such as:

- frequency with which primary data 112 or a secondary copy 116 of a data object or metadata has been or is predicted to be used, accessed, or modified;
- time-related factors (e.g., aging information such as time since the creation or modification of a data object);
- deduplication information (e.g., hashes, data blocks, deduplication block size, deduplication efficiency or other metrics);
- an estimated or historic usage or cost associated with different components (e.g., with secondary storage devices 108);
- the identity of users, applications 110, client computing devices 102 and/or other computing devices that created, accessed, modified, or otherwise utilized primary data 112 or secondary copies 116;
- a relative sensitivity (e.g., confidentiality, importance) of a data object, e.g., as determined by its content and/or metadata;
- the current or historical storage capacity of various storage devices;
- the current or historical network capacity of network pathways connecting various components within the storage operation cell;
- access control lists or other security information; and
- the content of a particular data object (e.g., its textual content) or of metadata associated with the data object.

Exemplary Storage Policy and Secondary Copy Operations

Figure 1E:
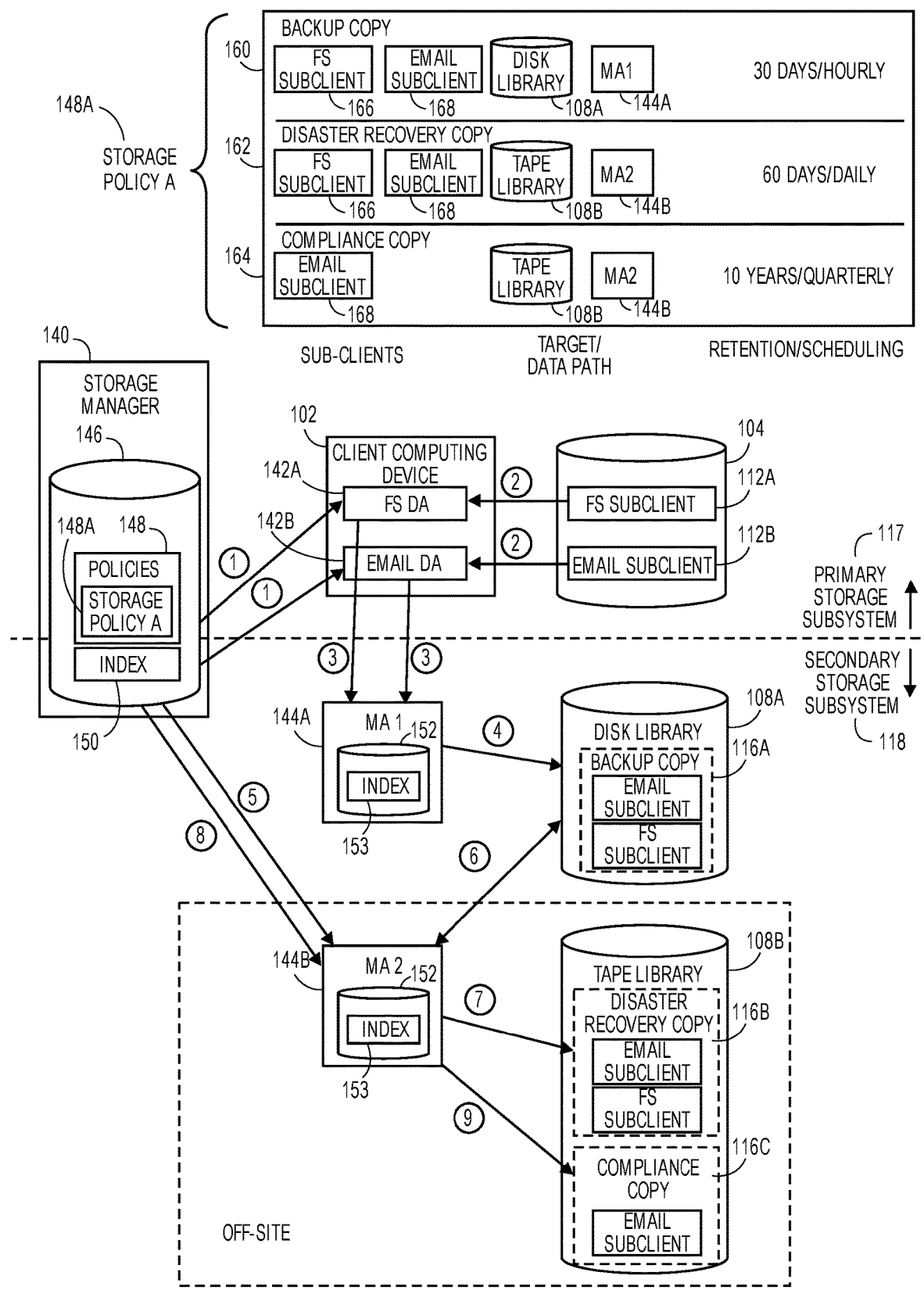
FIG. 1E illustrates certain secondary copy operations according to an exemplary storage policy.

FIG. 1E includes a data flow diagram depicting performance of secondary copy operations by an embodiment of information management system 100, according to an exemplary storage policy 148A. System 100 includes a storage manager 140, a client computing device 102 having a file system data agent 142A and an email data agent 142B operating thereon, a primary storage device 104, two media agents 144A, 144B, and two secondary storage devices 108: a disk library 108A and a tape library 108B. As shown, primary storage device 104 includes primary data 112A, which is associated with a logical grouping of data associated with a file system ("file system subclient"), and primary data 112B, which is a logical grouping of data associated with email ("email subclient"). The techniques described with respect to FIG. 1E, can be utilized in conjunction with data that is otherwise organized as well.

As indicated by the dashed box, the second media agent 144B and tape library 108B are "off-site," and may be remotely located from the other components in system 100 (e.g., in a different city, office building, etc.). Indeed, "off-site" may refer to a magnetic tape located in remote storage, which must be manually retrieved and loaded into a tape drive to be read. In this manner, information stored on the tape library 108B may provide protection in the event of a disaster or other failure at the main site(s) where data is stored.

The file system subclient 112A in certain embodiments generally comprises information generated by the file system and/or operating system of client computing device 102, and can include, for example, file system data (e.g., regular files, file tables, mount points, etc.), operating system data (e.g., registries, event logs, etc.), and the like. The e-mail subclient 112E can include data generated by an e-mail application operating on client computing device 102, e.g., mailbox information, folder information, emails, attachments, associated database information, and the like. As described above, the subclients can be logical containers, and the data included in the corresponding primary data 112A and 112B may or may not be stored contiguously.

The exemplary storage policy 148A includes backup copy preferences or rule set 160, disaster recovery copy preferences or rule set 162, and compliance copy preferences or rule set 164. Backup copy rule set 160 specifies that it is associated with file system subclient 166 and email subclient 168. Each of subclients 166 and 168 are associated with the particular client computing device 102, Backup copy rule set 160 further specifies that the backup operation will be written to disk library 108A and designates a particular media agent 144A to convey the data to disk library 108A. Finally, backup copy rule set 160 specifies that backup copies created according to rule set 160 are scheduled to be generated hourly and are to be retained for 30 days. In some other embodiments, scheduling information is not included in storage policy 148A and is instead specified by a separate scheduling policy.

Disaster recovery copy rule set 162 is associated with the same two subclients 166 and 168. However, disaster recovery copy rule set 162 is associated with tape library 108B, unlike backup copy rule set 160. Moreover, disaster recovery copy rule set 162 specifies that a different media agent, namely 144B, will convey data to tape library 108B. Disaster recovery copies created according to rule set 162 will be retained for 60 days and will be generated daily. Disaster recovery copies generated according to disaster recovery copy rule set 162 can provide protection in the event of a disaster or other catastrophic data loss that would affect the backup copy 116A maintained on disk library 108A.

Compliance copy rule set 164 is only associated with the email subclient 168, and not the file system subclient 166. Compliance copies generated according to compliance copy rule set 164 will therefore not include primary data 112A from the file system subclient 166. For instance, the organization may be under an obligation to store and maintain copies of email data for a particular period of time (e.g., 10 years) to comply with state or federal regulations, while similar regulations do not apply to file system data. Compliance copy rule set 164 is associated with the same tape library 108B and media agent 144B as disaster recovery copy rule set 162, although a different storage device or media agent could be used in other embodiments. Finally, compliance copy rule set 164 specifies that the copies it governs will be generated quarterly and retained for 10 years.

Secondary Copy Jobs

A logical grouping of secondary copy operations governed by a rule set and being initiated at a point in time may be referred to as a "secondary copy job" (and sometimes may be called a "backup job," even though it is not necessarily limited to creating only backup copies). Secondary copy jobs may be initiated on demand as well. Steps 1-9 below illustrate three secondary copy jobs based on storage policy 148A.

Referring to FIG. 1E, at step 1, storage manager 140 initiates a backup job according to the backup copy rule set 160, which logically comprises all the secondary copy operations necessary to effectuate rules 160 in storage policy 148A every hour, including steps 1-4 occurring hourly. For instance, a scheduling service running on storage manager 140 accesses backup copy rule set 160 or a separate scheduling policy associated with client computing device 102 and initiates a backup job on an hourly basis, Thus, at the scheduled time, storage manager 140 sends instructions to client computing device 102 (i.e., to both data agent 142A and data agent 142B) to begin the backup job.

At step 2, file system data agent 142A and email data agent 142B on client computing device 102 respond to instructions from storage manager 140 by accessing and processing the respective subclient primary data 112A and 112B involved in the backup copy operation, which can be found in primary storage device 104. Because the secondary copy operation is a backup copy operation, the data agent(s) 142A, 142B may format the data into a backup format or otherwise process the data suitable for a backup copy.

At step 3, client computing device 102 communicates the processed file system data (e.g., using file system data agent 142A) and the processed email data (e.g., using email data agent 142B) to the first media agent 144A according to backup copy rule set 160, as directed by storage manager 140. Storage manager 140 may further keep a record in management database 146 of the association between media agent 144A and one or more of: client computing device 102, file system subclient 112A, file system data agent 142A, email subclient 112B, email data agent 142B, and/or backup copy 116A.

The target media agent 144A receives the data-agent-processed data from client computing device 102, and at step 4 generates and conveys backup copy 116A to disk library 108A to be stored as backup copy 116A, again at the direction of storage manager 140 and according to backup copy rule set 160. Media agent 144A can also update its index 153 to include data and/or metadata related to backup copy 116A, such as information indicating where the backup copy 116A resides on disk library 108A, where the email copy resides, where the file system copy resides, data and metadata for cache retrieval, etc. Storage manager 140 may similarly update its index 150 to include information relating to the secondary copy operation, such as information relating to the type of operation, a physical location associated with one or more copies created by the operation, the time the operation was performed, status information relating to the operation, the components involved in the operation, and the like. In some cases, storage manager 148 may update its index 150 to include some or all of the information stored in index 153 of media agent 144A. At this point, the backup job may be considered complete. After the 30-day retention period expires, storage manager 140 instructs media agent 144A to delete backup copy 116A from disk library 108A and indexes 150 and/or 153 are updated accordingly.

At step 5, storage manager 140 initiates another backup job for a disaster recovery copy according to the disaster recovery rule set 162. Illustratively, this includes steps 5-7 occurring daily for creating disaster recovery copy 116B. Illustratively, and by way of illustrating the scalable aspects and off-loading principles embedded in system 100, disaster recovery copy 115E is based on backup copy 116A and not on primary data 112A and 112B.

At step 6, illustratively based on instructions received from storage manager 140 at step 5, the specified media agent 144B retrieves the most recent backup copy 116A from disk library 108A.

At step 7, again at the direction of storage manager 140 and as specified in disaster recovery copy rule set 162, media agent 144B uses the retrieved data to create a disaster recovery copy 116B and store it to tape library 108B. In some cases, disaster recovery copy 116B is a direct, mirror copy of backup copy 116A, and remains in the backup format. In other embodiments, disaster recovery copy 116B may be further compressed or encrypted, or may be generated in some other manner, such as by using primary data 112A and 112B from primary storage device 104 as sources. The disaster recovery copy operation is initiated once a day and disaster recovery copies 116B are deleted after 60 days; indexes 153 and/or 150 are updated accordingly when/after each information management operation is executed and/or completed. The present backup job may be considered completed.

At step 8, storage manager 140 initiates another backup job according to compliance rule set 164, which performs steps 8-9 quarterly to create compliance copy 116C. For instance, storage manager 140 instructs media agent 144B to create compliance copy 116C on tape library 108B, as specified in the compliance copy rule set 164.

At step 9 in the example, compliance copy 116C is generated using disaster recovery copy 116B as the source. This is efficient, because disaster recovery copy resides on the same secondary storage device and thus no network resources are required to move the data. In other embodiments, compliance copy 116C is instead generated using primary data 112B corresponding to the email subclient or using backup copy 116A from disk library 108A as source data. As specified in the illustrated example, compliance copies 116C are created quarterly, and are deleted after ten years, and indexes 153 and/or 150 are kept up-to-date accordingly.

Exemplary Applications of Storage Policies—Information Governance Policies and Classification Again referring to FIG. 1E, storage manager 140 may permit a user to specify aspects of storage policy 148A. For example, the storage policy can be modified to include information governance policies to define how data should be managed in order to comply with a certain regulation or business objective. The various policies may be stored, for example, in management database 146. An information governance policy may align with one or more compliance tasks that are imposed by regulations or business requirements. Examples of information governance policies might include a Sarbanes-Oxley policy, a HIPAA policy, an electronic discovery (e-discovery) policy, and so on.

Information governance policies allow administrators to obtain different perspectives on an organization's online and offline data, without the need for a dedicated data silo created solely for each different viewpoint. As described previously, the data storage systems herein build an index that reflects the contents of a distributed data set that spans numerous clients and storage devices, including both primary data and secondary copies, and online and offline copies. An organization may apply multiple information governance policies in a top-down manner over that unified data set and indexing schema in order to view and manipulate the data set through different lenses, each of which is adapted to a particular compliance or business goal. Thus, for example, by applying an e-discovery policy and a Sarbanes-Oxley policy, two different groups of users in an organization can conduct two very different analyses of the same underlying physical set of data/copies, which may be distributed throughout the information management system.

An information governance policy may comprise a classification policy, which defines a taxonomy of classification terms or tags relevant to a compliance task and/or business objective. A classification policy may also associate a defined tag with a classification rule. A classification rule defines a particular combination of criteria, such as users who have created, accessed or modified a document or data object; file or application types; content or metadata keywords; clients or storage locations; dates of data creation and/or access; review status or other status within a workflow (e.g., reviewed or un-reviewed): modification times or types of modifications; and/or any other data attributes in any combination, without limitation. A classification rule may also be defined using other classification tags in the taxonomy. The various criteria used to define a classification rule may be combined in any suitable fashion, for example, via Boolean operators, to define a complex classification rule. As an example, an e-discovery classification policy might define a classification tag "privileged" that is associated with documents or data objects that (1) were created or modified by legal department staff, or (2) were sent to or received from outside counsel via email, or (3) contain one of the following keywords: "privileged" or "attorney" or "counsel," or other like terms. Accordingly, all these documents or data objects will be classified as "privileged."

One specific type of classification tag, which may be added to an index at the time of indexing, is an "entity tag." An entity tag may be, for example, any content that matches a defined data mask format. Examples of entity tags might include, e.g., social security numbers (e.g., any numerical content matching the formatting mask XXX-XX-XXXX), credit card numbers (e.g., content having a 13-16 digit string of numbers), SKU numbers, product numbers, etc. A user may define a classification policy by indicating criteria, parameters or descriptors of the policy via a graphical user interface, such as a form or page with fields to be filled in, pull-down menus or entries allowing one or more of several options to be selected, buttons, sliders, hypertext links or other known user interface tools for receiving user input, etc. For example, a user may define certain entity tags, such as a particular product number or project ID, In some implementations, the classification policy can be implemented using cloud-based techniques. For example, the storage devices may be cloud storage devices, and the storage manager 140 may execute cloud service provider API over a network to classify data stored on cloud storage devices.

Restore Operations from Secondary Copies

While not shown in FIG. 1E, at some later point in time, a restore operation can be initiated involving one or more of secondary copies 116A, 116B, and 116C. A restore operation logically takes a selected secondary copy 116, reverses the effects of the secondary copy operation that created it, and stores the restored data to primary storage where a client computing device 102 may properly access it as primary data. A media agent 144 and an appropriate data agent 142 (e.g., executing on the client computing device 102) perform the tasks needed to complete a restore operation. For example, data that was encrypted, compressed, and/or deduplicated in the creation of secondary copy 116 will be correspondingly rehydrated (reversing deduplication), uncompressed, and unencrypted into a format appropriate to primary data. Metadata stored within or associated with the secondary copy 116 may be used during the restore operation. In general, restored data should be indistinguishable from other primary data 112. Preferably, the restored data has fully regained the native format that may make it immediately usable by application 110.

As one example, a user may manually initiate a restore of backup copy 116A, e.g., by interacting with user interface 158 of storage manager 140 or with a web-based console with access to system 100. Storage manager 140 may accesses data in its index 150 and/or management database 146 (and/or the respective storage policy 148A) associated with the selected backup copy 116A to identify the appropriate media agent 144A and/or secondary storage device 108A where the secondary copy resides. The user may be presented with a representation (e.g., stub, thumbnail, listing, etc.) and metadata about the selected secondary copy, in order to determine whether this is the appropriate copy to be restored, e.g., date that the original primary data was created. Storage manager 140 will then instruct media agent 144A and an appropriate data agent 142 on the target client computing device 102 to restore secondary copy 116A to primary storage device 104. A media agent may be selected for use in the restore operation based on a load balancing algorithm, an availability based algorithm, or other criteria. The selected media agent, e.g., 144A, retrieves secondary copy 116A from disk library 108A. For instance, media agent 144A may access its index 153 to identify a location of backup copy 116A on disk library 108A, or may access location information residing on disk library 108A itself.

In some cases a backup copy 116A that was recently created or accessed, may be cached to speed up the restore operation. In such a case, media agent 144A accesses a cached version of backup copy 116A residing in index 153, without having to access disk library 108A for some or all of the data. Once it has retrieved backup copy 116A, the media agent 144A communicates the data to the requesting client computing device 102, Upon receipt, file system data agent 142A and email data agent 142B may unpack (e.g., restore from a backup format to the native application format) the data in backup copy 116A and restore the unpackaged data to primary storage device 104. In general, secondary copies 116 may be restored to the same volume or folder in primary storage device 104 from which the secondary copy was derived; to another storage location or client computing device 102; to shared storage, etc. In some cases, the data may be restored so that it may be used by an application 110 of a different version/vintage from the application that created the original primary data 112.

Exemplary Second Copy Formatting

The formatting and structure of secondary copies 116 can vary depending on the embodiment. In some cases, secondary copies 116 are formatted as a series of logical data units or "chunks" (e.g., 512 MB, 1 GB, 2 GB, 4 GB, or 8 GB chunks). This can facilitate efficient communication and writing to secondary storage devices 108, e.g., according to resource availability. For example, a single secondary copy 116 may be written on a chunk-by-chunk basis to one or more secondary storage devices 108. In some cases, users can select different chunk sizes, e.g., to improve throughput to tape storage devices. Generally, each chunk can include a header and a payload. The payload can include files (or other data units) or subsets thereof included in the chunk, whereas the chunk header generally includes metadata relating to the chunk, some or all of which may be derived from the payload. For example, during a secondary copy operation, media agent 144, storage manager 140, or other component may divide files into chunks and generate headers for each chunk by processing the files. Headers can include a variety of information such as file and/or volume identifier(s), offset(s), and/or other information associated with the payload data items, a chunk sequence number, etc. Importantly, in addition to being stored with secondary copy 116 on secondary storage device 108, chunk headers can also be stored to index 153 of the associated media agent(s) 144 and/or to index 150 associated with storage manager 140. This can be useful for providing faster processing of secondary copies 116 during browsing, restores, or other operations. In some cases, once a chunk is successfully transferred to a secondary storage device 108, the secondary storage device 108 returns an indication of receipt, e.g., to media agent 144 and/or storage manager 140, which may update their respective indexes 153, 150 accordingly. During restore, chunks may be processed (e.g., by media agent 144) according to the information in the chunk header to reassemble the files.

Data can also be communicated within system 100 in data channels that connect client computing devices 102 to secondary storage devices 108. These data channels can be referred to as "data streams," and multiple data streams can be employed to parallelize an information management operation, improving data transfer rate, among other advantages. Example data formatting techniques including techniques involving data streaming, chunking, and the use of other data structures in creating secondary copies are described in U.S. Pat. Nos. 7,315,923, 8,156,086, and 8,578,120.

Figure 1F:
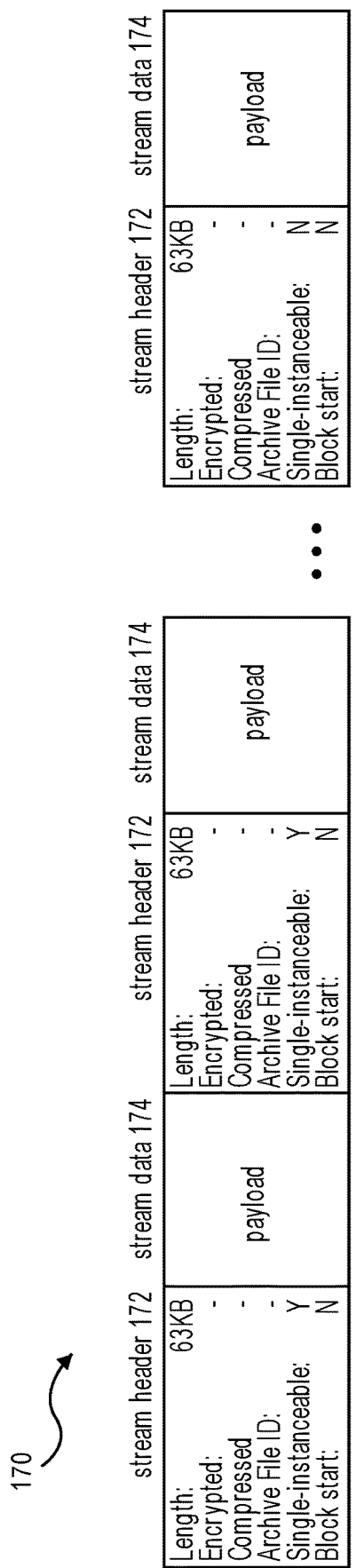
FIGS. 1F-1H are block diagrams illustrating suitable data structures that may be employed by the information management system.
Figure 1G:
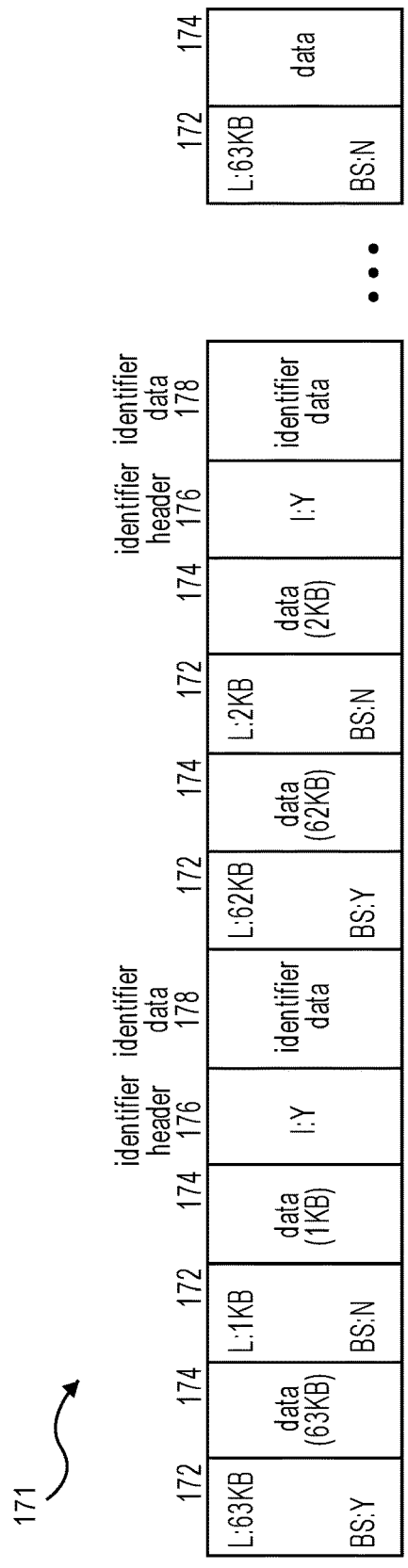

FIGS. 1F and 1G are diagrams of example data streams 170 and 171, respectively, which may be employed for performing information management operations. Referring to FIG. 1F, data agent 142 forms data stream 170 from source data associated with a client computing device 102 (e.g., primary data 112). Data stream 170 is composed of multiple pairs of stream header 172 and stream data (or stream payload) 174. Data streams 170 and 171 shown in the illustrated example are for a single-instanced storage operation, and a stream payload 174 therefore may include both single-instance (SI) data and/or non-SI data. A stream header 172 includes metadata about the stream payload 174. This metadata may include, for example, a length of the stream payload 174, an indication of whether the stream payload 174 is encrypted, an indication of whether the stream payload 174 is compressed, an archive file identifier (ID), an indication of whether the stream payload 174 is single instanceable, and an indication of whether the stream payload 174 is a start of a block of data.

Referring to FIG. 1C, data stream 171 has the stream header 172 and stream payload 174 aligned into multiple data blocks. In this example, the data blocks are of size 64 KB. The first two stream header 172 and stream payload 174 pairs comprise a first data block of size 64 KB. The first stream header 172 indicates that the length of the succeeding stream payload 174 is 63 KB and that it is the start of a data block. The next stream header 172 indicates that the succeeding stream payload 174 has a length of 1 KB and that it is not the start of a new data block. Immediately following stream payload 174 is a pair comprising an identifier header 176 and identifier data 178. The identifier header 176 includes an indication that the succeeding identifier data 178 includes the identifier for the immediately previous data block. The identifier data 178 includes the identifier that the data agent 142 generated for the data block. The data stream 171 also includes other stream header 172 and stream payload 174 pairs, which may be for SI data and/or non-SI data.

Figure 1H:
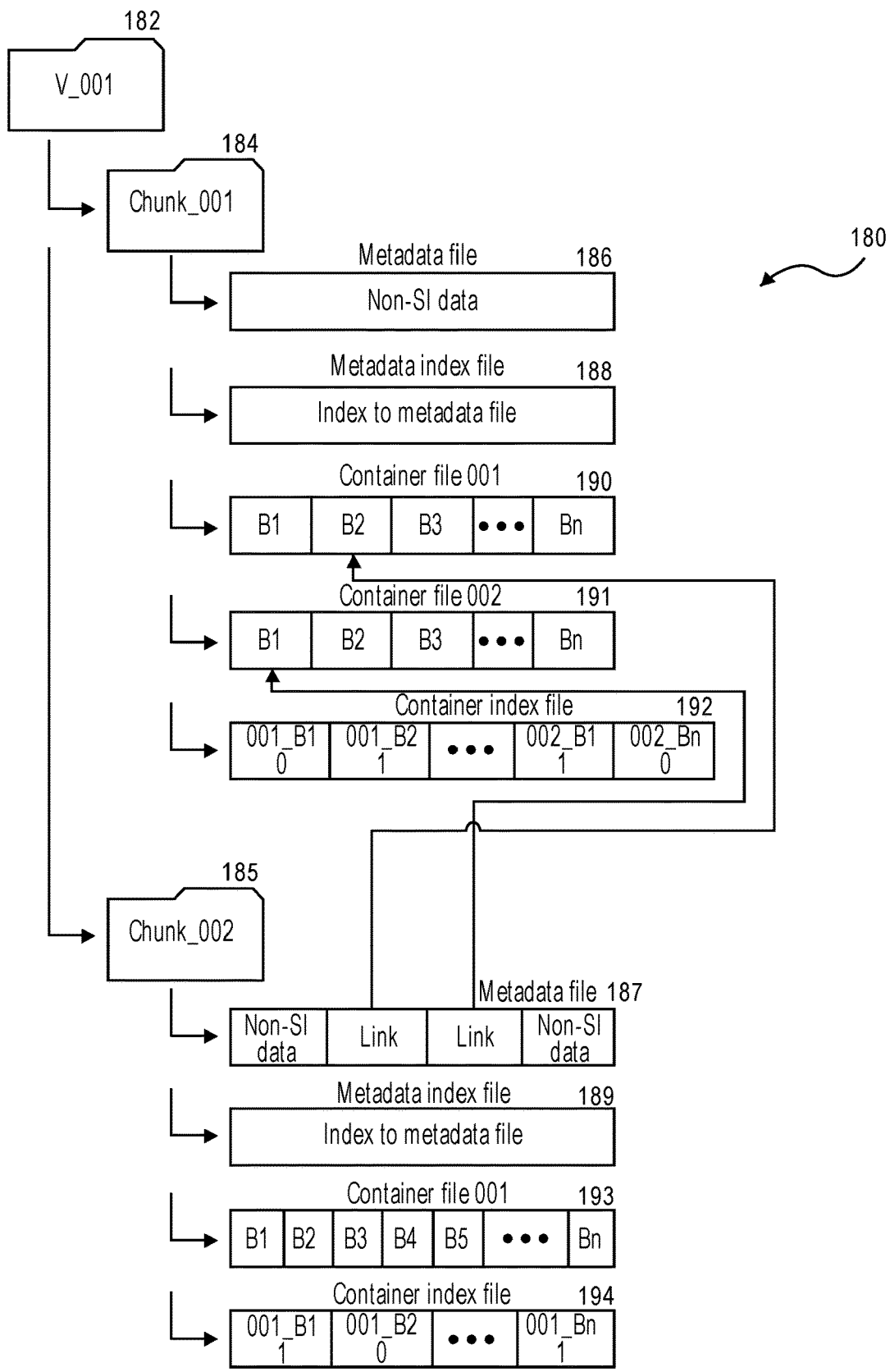

FIG. 1H is a diagram illustrating data structures 180 that may be used to store blocks of SI data and non-SI data on a storage device (e.g., secondary storage device 108), According to certain embodiments, data structures 180 do not form part of a native file system of the storage device. Data structures 180 include one or more volume folders 182, one or more chunk folders 184/185 within the volume folder 182, and multiple files within chunk folder 184. Each chunk folder 184/185 includes a metadata file 186/187, a metadata index file 188/189, one or more container files 190/191/193, and a container index file 192/194. Metadata file 186/187 stores non-SI data blocks as well as links to SI data blocks stored in container files. Metadata index file 188/189 stores an index to the data in the metadata file 186/187. Container files 190/191/193 store SI data blocks. Container index file 192/194 stores an index to container files 190/191/193. Among other things, container index file 192/194 stores an indication of whether a corresponding block in a container file 190/191/193 is referred to by a link in a metadata file 186/187. For example, data block B2 in the container file 190 is referred to by a link in metadata file 187 in chunk folder 185. Accordingly, the corresponding index entry in container index file 192 indicates that data block B2 in container file 190 is referred to. As another example, data block B1 in container file 191 is referred to by a link in metadata file 187, and so the corresponding index entry in container index file 192 indicates that this data block is referred to.

As an example, data structures 180 illustrated in FIG. 1H may have been created as a result of separate secondary copy operations involving two client computing devices 102. For example, a first secondary copy operation on a first client computing device 102 could result in the creation of the first chunk folder 184, and a second secondary copy operation on a second client computing device 102 could result in the creation of the second chunk folder 185. Container files 190/191 in the first chunk folder 184 would contain the blocks of SI data of the first client computing device 102. If the two client computing devices 102 have substantially similar data, the second secondary copy operation on the data of the second client computing device 102 would result in media agent 144 storing primarily links to the data blocks of the first client computing device 102 that are already stored in the container files 190/191. Accordingly, while a first secondary copy operation may result in storing nearly all of the data subject to the operation, subsequent secondary storage operations involving similar data may result in substantial data storage space savings, because links to already stored data blocks can be stored instead of additional instances of data blocks.

If the operating system of the secondary storage computing device 106 on which media agent 144 operates supports sparse files, then when media agent 144 creates container files 190/1911193, it can create them as sparse files. A sparse file is a type of file that may include empty space (e.g., a sparse file may have real data within it, such as at the beginning of the file and/or at the end of the file, but may also have empty space in it that is not storing actual data, such as a contiguous range of bytes all having a value of zero). Having container files 190/191/193 be sparse files allows media agent 144 to free up space in container files 190/191/193 when blocks of data in container files 190/191/193 no longer need to be stored on the storage devices. In some examples, media agent 144 creates a new container file 190/191/193 when a container file 190/191/193 either includes 100 blocks of data or when the size of the container file 190 exceeds 50 MB. In other examples, media agent 144 creates a new container file 190/191/193 when a container file 190/191/193 satisfies other criteria (e.g., it contains from approx. 100 to approx. 1000 blocks or when its size exceeds approximately 50 MB to 1 GB). In some cases, a file on which a secondary copy operation is performed may comprise a large number of data blocks. For example, a 100 MB file may comprise 400 data blocks of size 256 KB. If such a file is to be stored, its data blocks may span more than one container file, or even more than one chunk folder. As another example, a database file of 20 GB may comprise over 40,000 data blocks of size 512 KB. If such a database file is to be stored, its data blocks will likely span multiple container files, multiple chunk folders, and potentially multiple volume folders. Restoring such files may require accessing multiple container files, chunk folders, and/or volume folders to obtain the requisite data blocks.

Using Backup Data for Replication and Disaster Recovery ("Live Synchronization")

There is an increased demand to off-load resource intensive information management tasks (e.g., data replication tasks) away from production devices (e.g., physical or virtual client computing devices) in order to maximize production efficiency. At the same time, enterprises expect access to readily-available up-to-date recovery copies in the event of failure, with little or no production downtime.

Figure 2A:
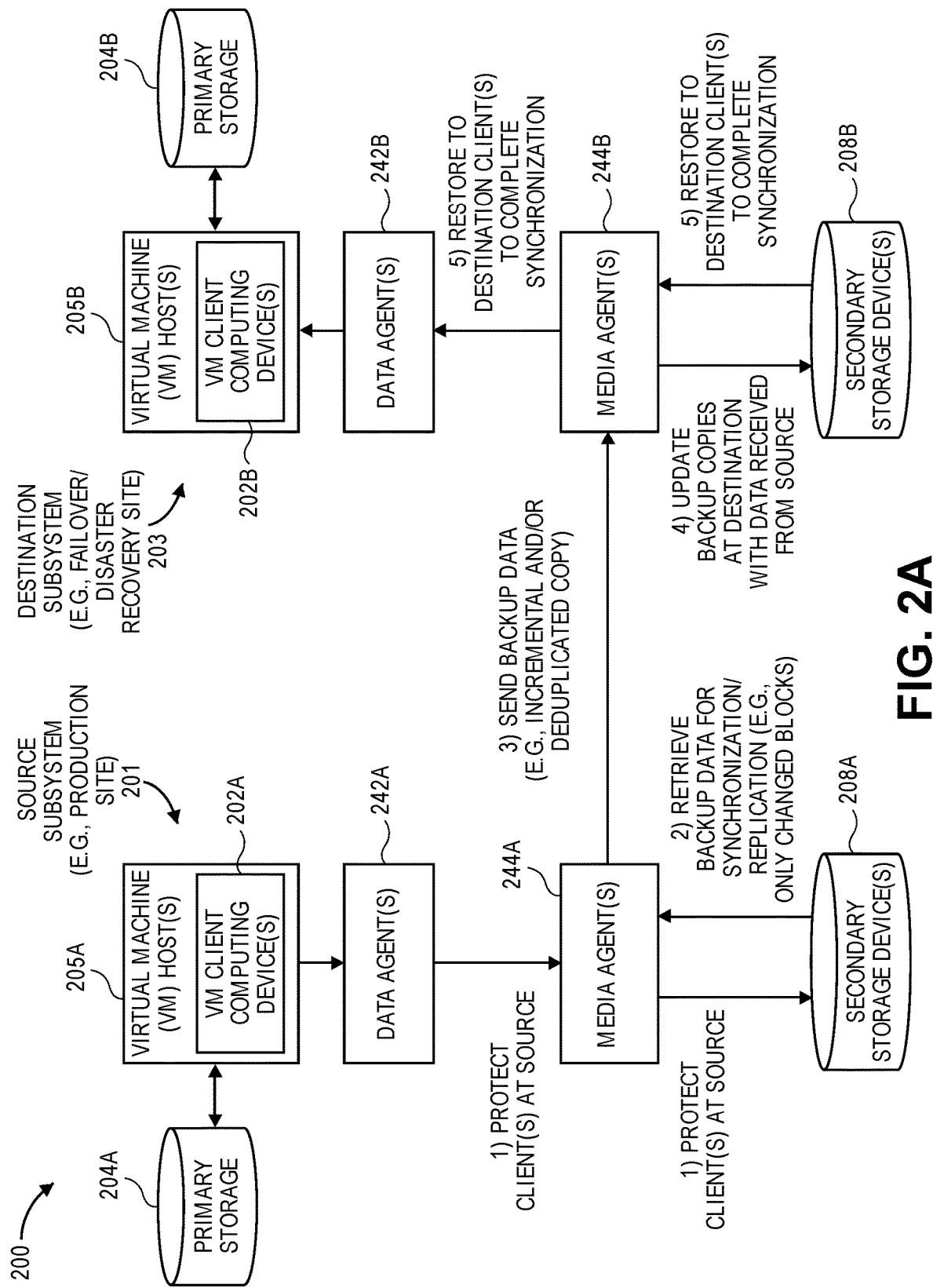
FIG. 2A illustrates a system and technique for synchronizing primary data to a destination such as a failover site using secondary copy data.

FIG. 2A illustrates a system 200 configured to address these and other issues by using backup or other secondary copy data to synchronize a source subsystem 201 (e.g., a production site) with a destination subsystem 203 (e.g., a failover site). Such a technique can be referred to as "live synchronization" and/or "live synchronization replication." In the illustrated embodiment, the source client computing devices 202a include one or more virtual machines (or "VMs") executing on one or more corresponding VM host computers 205a, though the source need not be virtualized. The destination site 203 may be at a location that is remote from the production site 201, or may be located in the same data center, without limitation. One or more of the production site 201 and destination site 203 may reside at data centers at known geographic locations, or alternatively may operate "in the cloud."

The synchronization can be achieved by generally applying an ongoing stream of incremental backups from the source subsystem 201 to the destination subsystem 203, such as according to what can be referred to as an "incremental forever" approach. FIG. 2A illustrates an embodiment of a data flow which may be orchestrated at the direction of one or more storage managers (not shown). At step 1, the source data agent(s) 242a and source media agent(s) 244a work together to write backup or other secondary copies of the primary data generated by the source client computing devices 202a into the source secondary storage device(s) 208a, At step 2, the backup/secondary copies are retrieved by the source media agent(s) 244a from secondary storage. At step 3, source media agent(s) 244a communicate the backup/secondary copies across a network to the destination media agent(s) 244b in destination subsystem 203.

As shown, the data can be copied from source to destination in an incremental fashion, such that only changed blocks are transmitted, and in some cases multiple incremental backups are consolidated at the source so that only the most current changed blocks are transmitted to and applied at the destination. An example of live synchronization of virtual machines using the "incremental forever" approach is found in U.S. Patent Application No. 62/265,339 entitled "Live Synchronization and Management of Virtual Machines across Computing and Virtualization Platforms and Using Live Synchronization to Support Disaster Recovery." Moreover, a deduplicated copy can be employed to further reduce network traffic from source to destination. For instance, the system can utilize the deduplicated copy techniques described in U.S. Pat. No. 9,239,687, entitled "Systems and Methods for Retaining and Using Data Block Signatures in Data Protection Operations."

At step 4, destination media agent(s) 244b write the received backup/secondary copy data to the destination secondary storage device(s) 208b. At step 5, the synchronization is completed when the destination media agent(s) and destination data agent(s) 242b restore the backup/secondary copy data to the destination client computing device(s) 202b. The destination client computing device(s) 202b may be kept "warm" awaiting activation in case failure is detected at the source. This synchronization/replication process can incorporate the techniques described in U.S. patent application Ser. No. 14/721,971, entitled "Replication Using Deduplicated Secondary Copy Data."

Where the incremental backups are applied on a frequent, on-going basis, the synchronized copies can be viewed as mirror or replication copies. Moreover, by applying the incremental backups to the destination site 203 using backup or other secondary copy data, the production site 201 is not burdened with the synchronization operations. Because the destination site 203 can be maintained in a synchronized "warm" state, the downtime for switching over from the production site 201 to the destination site 203 is substantially less than with a typical restore from secondary storage. Thus, the production site 201 may flexibly and efficiently fail over, with minimal downtime and with relatively up-to-date data, to a destination site 203, such as a cloud-based failover site. The destination site 203 can later be reverse synchronized back to the production site 201, such as after repairs have been implemented or after the failure has passed.

Integrating with the Cloud Using File System Protocols

Figure 2B:
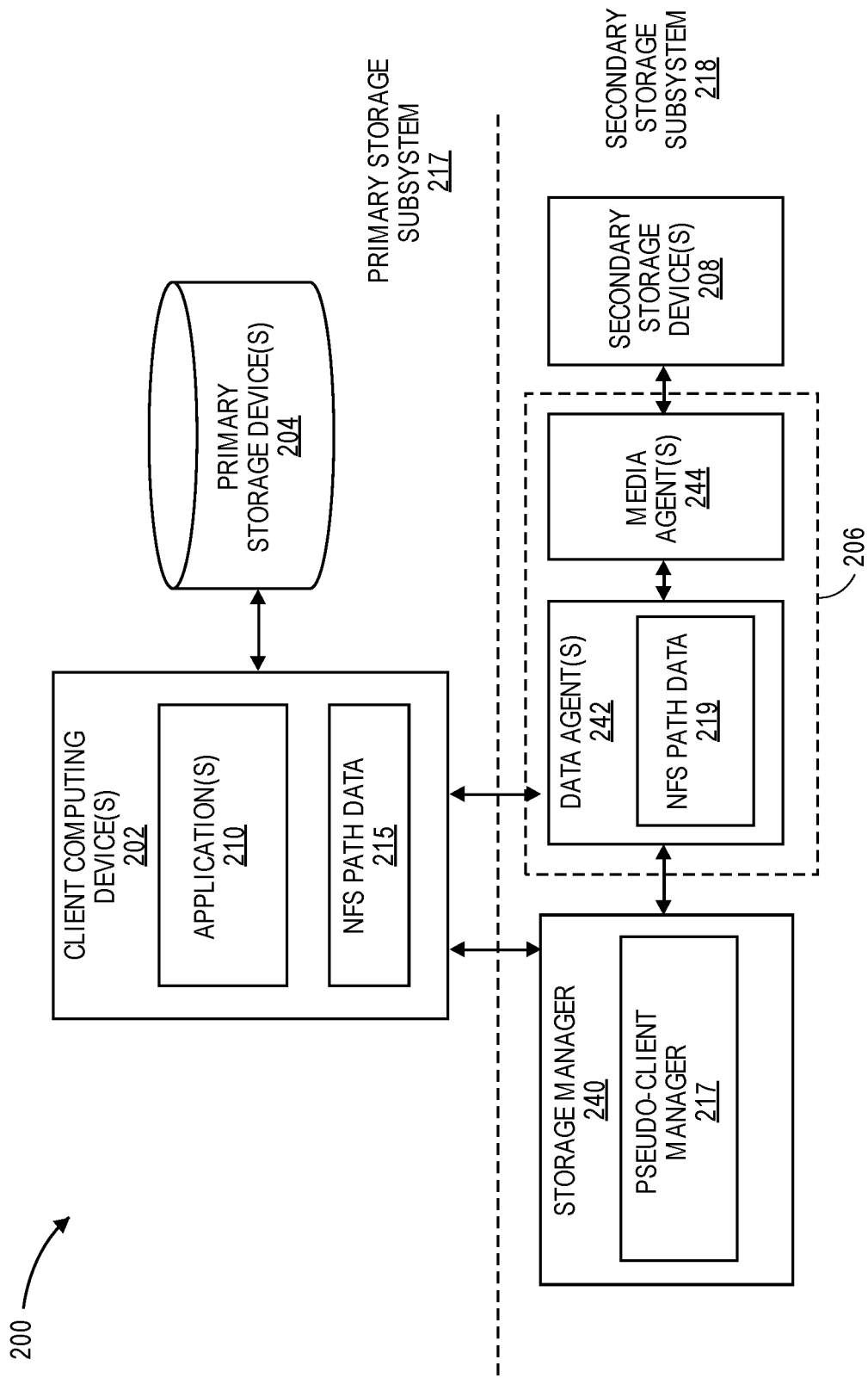
FIG. 2B illustrates an information management system architecture incorporating use of a network the system (NFS) protocol for communicating between the primary and secondary storage subsystems.

Given the ubiquity of cloud computing, it can be increasingly useful to provide data protection and other information management services in a scalable, transparent, and highly plug-able fashion. FIG. 2B illustrates an information management system 200 having an architecture that provides such advantages, and incorporates use of a standard file system protocol between primary and secondary storage subsystems 217, 218. As shown, the use of the network file system (NFS) protocol (or any another appropriate file system protocol such as that of the Common Internet File System (CIFS)) allows data agent 242 to be moved from the primary storage subsystem 217 to the secondary storage subsystem 218. For instance, as indicated by the dashed box 206 around data agent 242 and media agent 244, data agent 242 can co-reside with media agent 244 on the same server (e.g., a secondary storage computing device such as component 106), or in some other location in secondary storage subsystem 218.

Where NFS is used, for example, secondary storage subsystem 218 allocates an NFS network path to the client computing device 202 or to one or more target applications 210 running on client computing device 202. During a backup or other secondary copy operation, the client computing device 202 mounts the designated NFS path and writes data to that NFS path. The NFS path may be obtained from NFS path data 215 stored locally at the client computing device 202, and which may be a copy of or otherwise derived from NFS path data 219 stored in the secondary storage subsystem 218.

Write requests issued by client computing device(s) 202 are received by data agent 242 in secondary storage subsystem 218, which translates the requests and works in conjunction with media agent 244 to process and write data to a secondary storage device(s) 208, thereby creating a backup or other secondary copy. Storage manager 240 can include a pseudo-client manager 217, which coordinates the process by, among other things, communicating information relating to client computing device 202 and application 210 (e.g., application type, client computing device identifier, etc.) to data agent 242, obtaining appropriate NFS path data from the data agent 242 (e.g., NFS path information), and delivering such data to client computing device 202.

Conversely, during a restore or recovery operation client computing device 202 reads from the designated NFS network path, and the read request is translated by data agent 242. The data agent 242 then works with media agent 244 to retrieve, re-process (e.g., re-hydrate, decompress, decrypt), and forward the requested data to client computing device 202 using NFS.

By moving specialized software associated with system 200 such as data agent 242 off the client computing devices 202, the illustrative architecture effectively decouples the client computing devices 202 from the installed components of system 200, improving both scalability and plug-ability of system 200. Indeed, the secondary storage subsystem 218 in such environments can be treated simply as a read/write NFS target for primary storage subsystem 217, without the need for information management software to be installed on client computing devices 202. As one example, an enterprise implementing a cloud production computing environment can add VM client computing devices 202 without installing and configuring specialized information management software on these VMs. Rather, backups and restores are achieved transparently, where the new VMs simply write to and read from the designated NFS path. An example of integrating with the cloud using file system protocols or so-called "infinite backup" using NFS share is found in U.S. Patent Application No. 62/294,920, entitled "Data Protection Operations Based on Network Path Information." Examples of improved data restoration scenarios based on network-path information, including using stored backups effectively as primary data sources, may be found in U.S. Patent Application No. 62/297,057, entitled "Data Restoration Operations Based on Network Path Information."

Highly Scalable Managed Data Pool Architecture

Figure 2C:
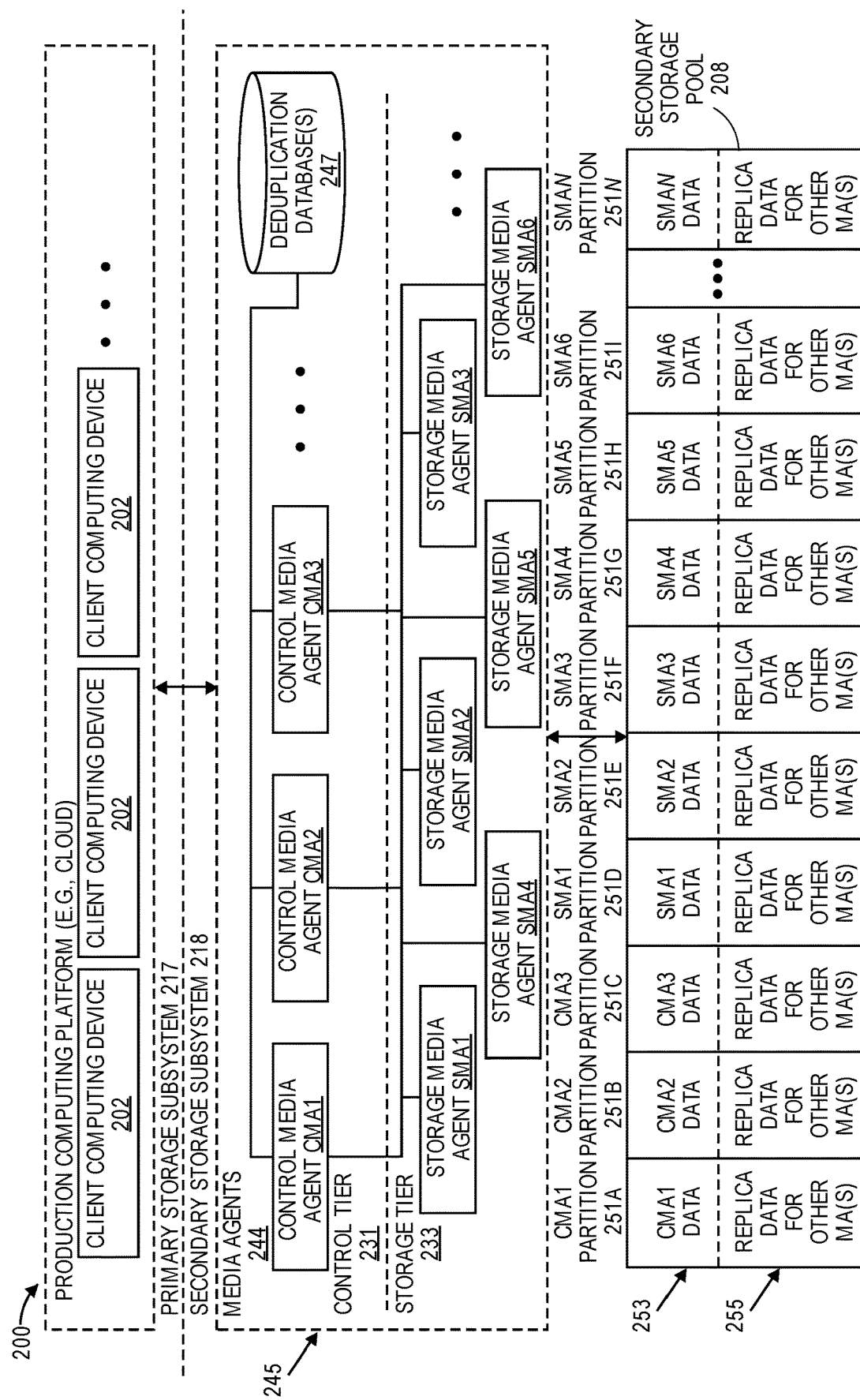
FIG. 2C is a block diagram of an example of a highly scalable managed data pool architecture.

Enterprises are seeing explosive data growth in recent years, often from various applications running in geographically distributed locations. FIG. 2C shows a block diagram of an example of a highly scalable, managed data pool architecture useful in accommodating such data growth. The illustrated system 200, which may be referred to as a "web-scale" architecture according to certain embodiments, can be readily incorporated into both open compute/storage and common-cloud architectures.

The illustrated system 200 includes a grid 245 of media agents 244 logically organized into a control tier 231 and a secondary or storage tier 233. Media agents assigned to the storage tier 233 can be configured to manage a secondary storage pool 208 as a deduplication store, and be configured to receive client write and read requests from the primary storage subsystem 217, and direct those requests to the secondary tier 233 for servicing. For instance, media agents CMA1-CMA3 in the control tier 231 maintain and consult one or more deduplication databases 247, which can include deduplication information (e.g., data block hashes, data block links, file containers for deduplicated files, etc.) sufficient to read deduplicated files from secondary storage pool 208 and write deduplicated files to secondary storage pool 208. For instance, system 200 can incorporate any of the deduplication systems and methods shown and described in U.S. Pat. No. 9,020,900, entitled "Distributed Deduplicated Storage System," and U.S. Pat. Pub. No. 2014/0201170, entitled "High Availability Distributed Reduplicated Storage System."

Media agents SMA1-SMA6 assigned to the secondary tier 233 receive write and read requests from media agents CMA1-CMA3 in control tier 231, and access secondary storage pool 208 to service those requests. Media agents CMA1-CMA3 in control tier 231 can also communicate with secondary storage pool 208, and may execute read and write requests themselves (e.g., in response to requests from other control media agents CMA1-CMA3) in addition to issuing requests to media agents in secondary tier 233. Moreover, while shown as separate from the secondary storage pool 208, deduplication database(s) 247 can in some cases reside in storage devices in secondary storage pool 208.

As shown, each of the media agents 244 (e.g., CMA1-CMA3, SMA1-SMA6, etc.) in grid 245 can be allocated a corresponding dedicated partition 251A-251I, respectively, in secondary storage pool 208. Each partition 251 can include a first portion 253 containing data associated with (e.g., stored by) media agent 244 corresponding to the respective partition 251. System 200 can also implement a desired level of replication, thereby providing redundancy in the event of a failure of a media agent 244 in grid 245. Along these lines, each partition 251 can further include a second portion 255 storing one or more replication copies of the data associated with one or more other media agents 244 in the grid.

System 200 can also be configured to allow for seamless addition of media agents 244 to grid 245 via automatic configuration. As one illustrative example, a storage manager (not shown) or other appropriate component may determine that it is appropriate to add an additional node to control tier 231, and perform some or all of the following: (i) assess the capabilities of a newly added or otherwise available computing device as satisfying a minimum criteria to be configured as or hosting a media agent in control tier 231; (ii) confirm that a sufficient amount of the appropriate type of storage exists to support an additional node in control tier 231 (e.g., enough disk drive capacity exists in storage pool 208 to support an additional deduplication database 247); (iii) install appropriate media agent software on the computing device and configure the computing device according to a pre-determined template; (iv) establish a partition 251 in the storage pool 208 dedicated to the newly established media agent 244; and (v) build any appropriate data structures (e.g., an instance of deduplication database 247). An example of highly scalable managed data pool architecture or so-called web-scale architecture for storage and data management is found in U.S. Patent Application No. 62/273,286 entitled "Redundant and Robust Distributed Deduplication Data Storage System."

The embodiments and components thereof disclosed in FIGS. 2A, 2B, and 20, as well as those in FIGS. 1A-1H, may be implemented in any combination and permutation to satisfy data storage management and information management needs at one or more locations and/or data centers.

On-Demand Metadata Extraction and Re-Indexing of Clinical Image Data System

Typically, a Clinical Image Archiving solution is used to archive, search, and restore medical/clinical imaging data generated using, from example, medical imaging software. All of the archived data is centrally located and accessible from any medical imaging endpoint using the Clinical Image Archiving tools. For example, a Clinical Image Archiving solution provides the following services: archive patient medical records to a central data storage repository from endpoints (e.g., computers where medical imaging software is installed), search patient records in the central data storage repository from endpoints based on information in supported medical data types, restore patient medical records from the central data storage repository to endpoints, and automatically restore relevant patient medical records to a client based on appointments scheduled in a system using various protocols (e.g., the Health Level-7 (HL7) protocol).

Figures 3A, 3B:
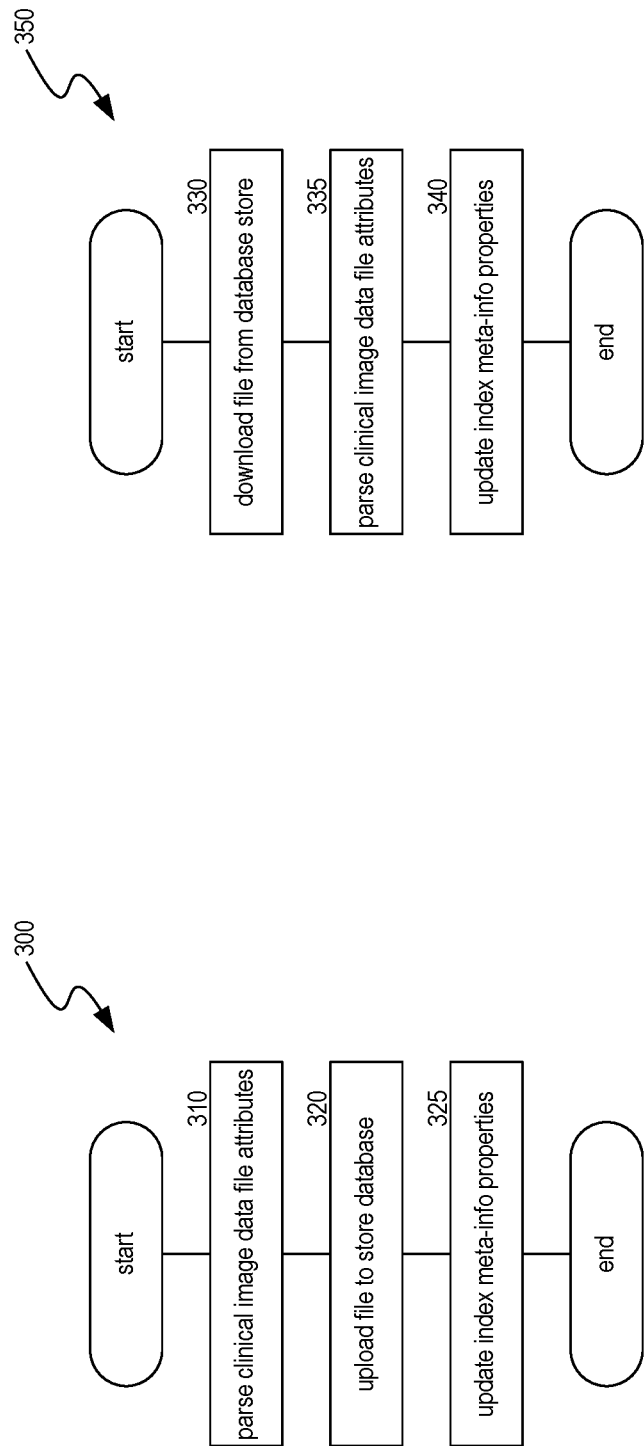
FIG. 3A depicts some salient operations of a method for storing medical/clinical image data in a central data storage repository using a Clinical Image Upload tool.
FIG. 3B depicts some salient operations of a method for reindexing medical/clinical image data stored in a central data storage repository using a Clinical Image Upload tool according to an illustrative embodiment of the present invention.

FIG. 3A depicts some salient operations of a method 300 for storing medical/clinical image data in a central data storage repository using a Clinical Image Upload tool (for example, element 540 in FIG. 540). The Clinical Image Upload tool allows a user to move medical/clinical data in bulk from a local machine to the central data storage repository configured for Clinical Image Archiving. Afterwards, the medical/clinical data can be queried and retrieved from medical imaging endpoints.

Figure 5A:
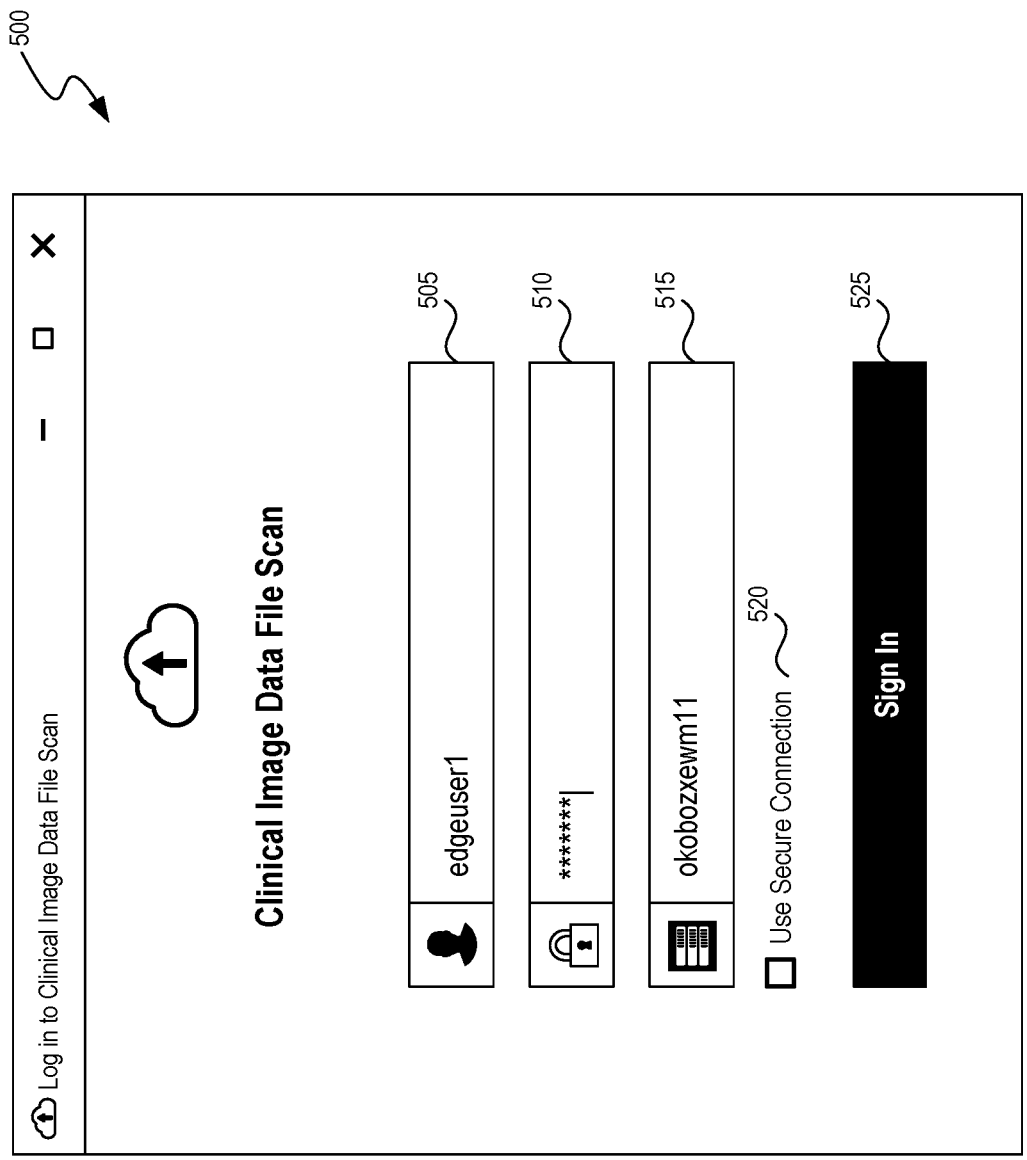
FIG. 5A depicts an illustrative graphical user interface for receiving login information from a user.
Figure 5B:
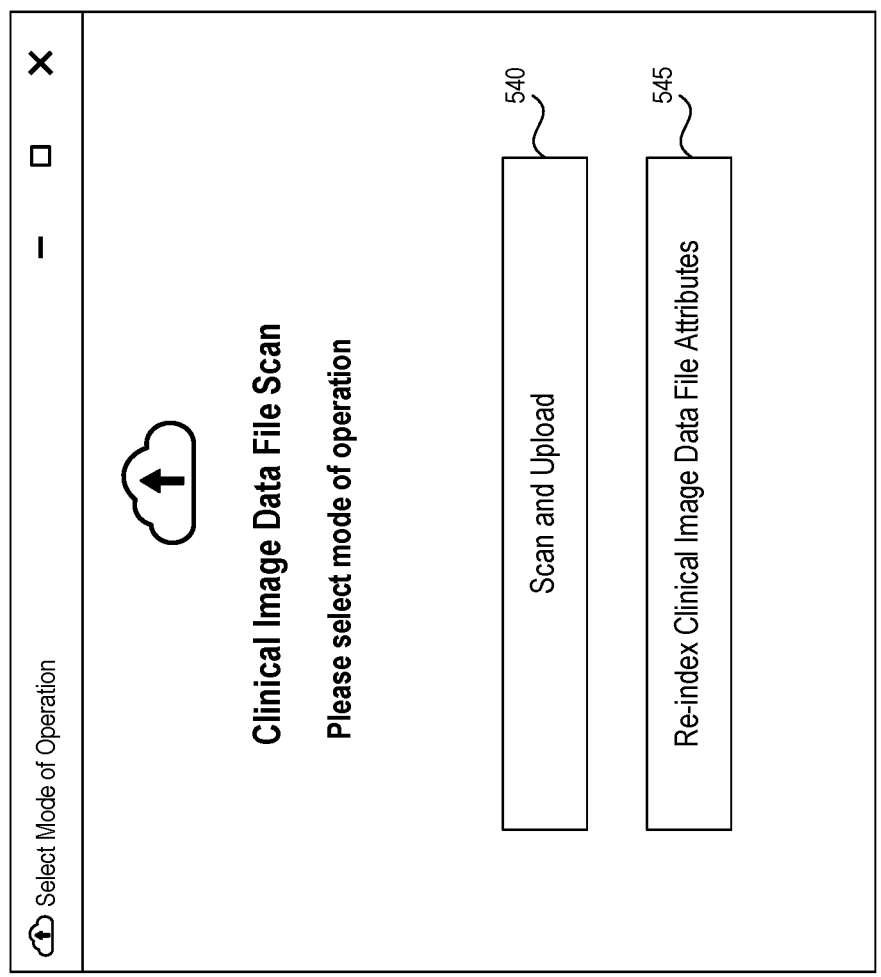
FIG. 5C depicts an illustrative graphical user interface for receiving folder selection(s) from a user for clinical image data upload.
FIG. 5D depicts an illustrative graphical user interface for displaying clinical image data upload progress to a user.

A user can log in to a Clinical Image Archiving solution via a login screen (e.g., as shown in FIG. 5A). FIG. 5A depicts an illustrative graphical user interface 500 for receiving login information from a user. A user can specify log in credentials (e.g., username (field 505) and password (field 510). A user can also specify a location of a domain associated with the user's clinical image data files. (field 515) as well as select the use of a secure connection (field 520). Once a user signs in (using field 525), the user can be presented with an option to select a mode of operation (e.g., upload or reindexing) of the Clinical Image Upload tool. FIG. 5B depicts an illustrative graphical user interface for receiving a mode selection (e.g., upload or reindexing) from a user. A user can select to scan and upload new clinical image data files (field 540) or reindex existing clinical image data files (field 545). When a user selects to scan and upload new clinical image data files, the user can select location(s) of the clinical image data files.

Figure 5C:
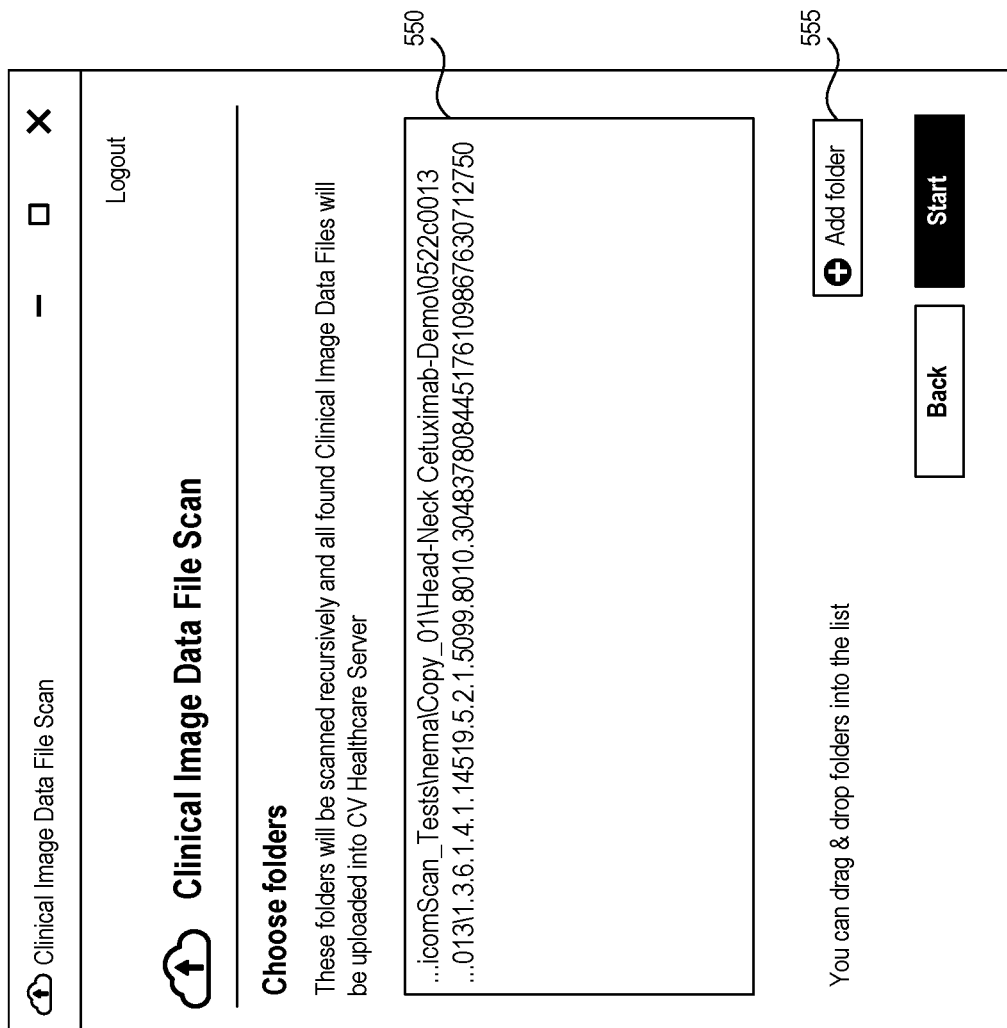

For example, FIG. 5C depicts an illustrative graphical user interface for receiving folder selection(s) from a user for clinical image data upload. A user can specify one or more folder locations (field 550) that include data files to be uploaded to a central data storage repository using a Clinical Image Upload tool. The user can add additional folders by selecting field 555 and/or dragging and dropping folders into the list 550. Once the user has selected the folder locations, the Clinical Image Upload tool can then scan the files in the selected folder(s) (act 310) and upload the relevant files to a central storage repository (act 320). In some embodiments, the Clinical Image Upload tool enables users to upload the relevant files automatically by implementing an API and exposing it to users. The API includes one or more functions that enable a computer system operated by the user to identify and upload relevant files to the Clinical Image Archiving solution. In some embodiments, the user may specify one or more specific locations at which the relevant files are stored. The API may access the specific locations to parse and upload the relevant files. In some embodiments, an API function can be programmed to parse and/or upload files of a particular file types (e.g., clinical image data files) and ignore files of other file types (e.g., text files, thumbnail files, etc.). This API may also be used by users in order to provide a user interface for the manual review and/or examination of relevant clinical image data files.

Figure 4:
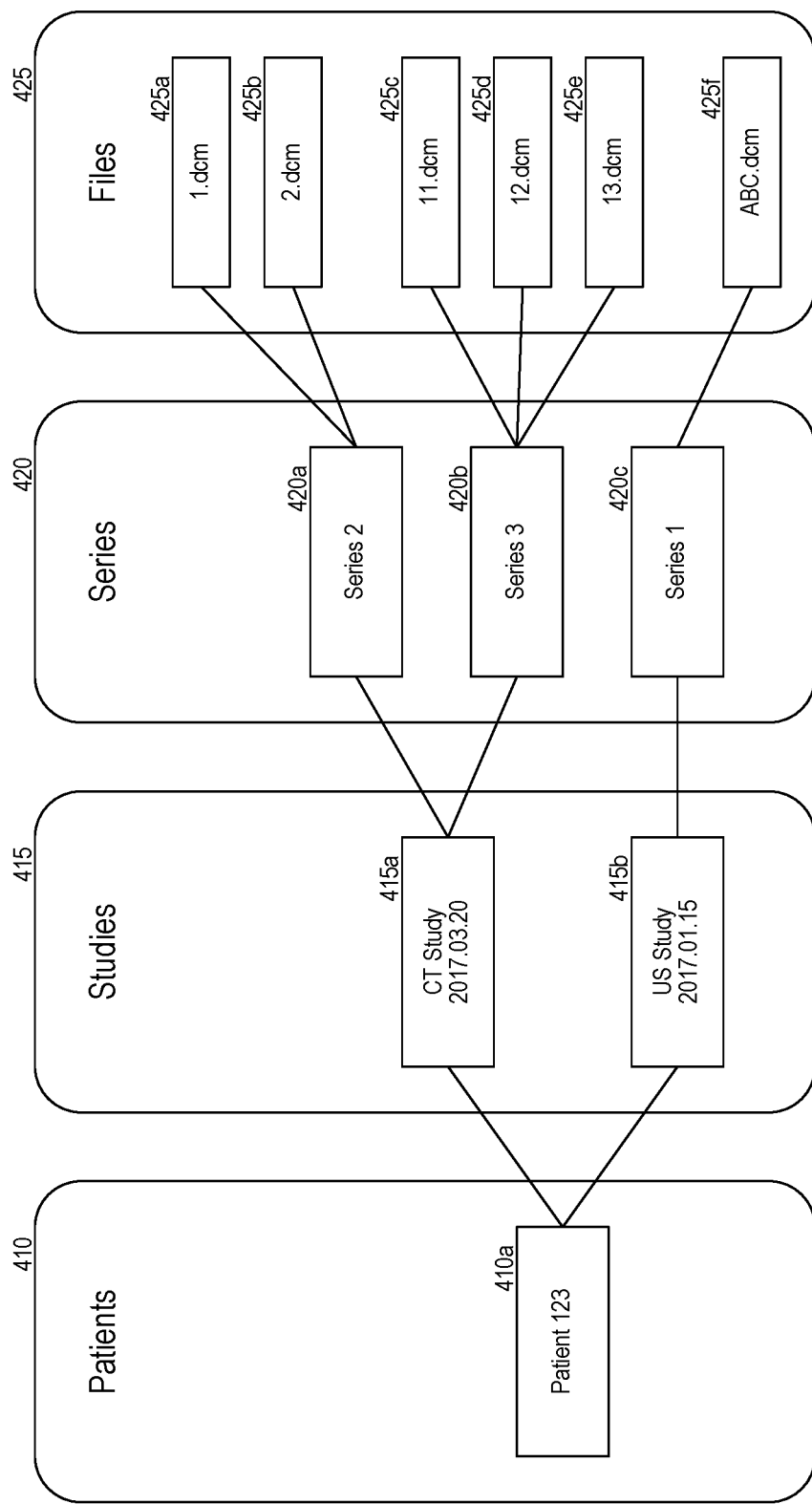
FIG. 4 depicts an exemplary storage structure for storing clinical image data files.

In some embodiments, the Clinical Image Upload tool may expect a specific storage structure for the clinical image data. FIG. 4 depicts an exemplary storage structure for storing DICOM files. For example, the Clinical Image Upload tool may expect the clinical image data to be stored according to the following hierarchical storage structure: Patients 410, Studies 415, Series 420, and Files 425. In the example depicted in FIG. 4, Patient 123 (410a) is associated with two studies CT Study 2017 Mar. 20 (415a) and US Study 2017 Jan. 15 (415b). Each study can be associated with one or more Series. For example, CT Study 2017 Mar. 20 (415a) is associated with Series 2 (420a) and Series 3 (420b) whereas US Study 2017 Jan. 15 (415b) is associated with Series 1 (420c). Each Series may then be associated with one or more files that comprise clinical image data. For example, Series 2 (420a) is associated with two DICOM Files 1.dcm (425a) and 2.dcm (425b), Series 3 (420b) is associated with three DICOM Files 11.dcm (425c), 12.dcm (425d), and 13.dcm (425c), and Series 1 is associated with one DICOM File ABC.dcm (425f). Upon receiving the folder selection from the user, the Clinical Image Upload tool may scan the hierarchy to locate the clinical image data files associated with each patient.

A clinical image data the typically starts with a header that contains meta-information. Each piece of meta-information may be called attribute, addressed by Group/Element. FIG. 7 depicts an example of a DICOM header file. For example, the DICOM header file shown in FIG. 7 comprises several elements (e.g., patient name, patient identifier, etc.), value representation (VR) of each element (e.g., data type and format of that element's value(s)), length of each element, and a format of each element value.

The Clinical Image Upload Tool also has access to one or more configurable schema files that specify the attributes in each clinical image data file that are to be uploaded to the central data storage repository, Since the header files of clinical image data files comprise a large number of attributes, not all of which might be useful for a user, typical clinical image archiving solutions only extract a subset of attributes from each clinical image data file's header, FIG. 8 depicts an example of a configurable schema file that comprises several attributes, including patent identifier, patient name, study date, study time, and referring physician for which information is to be extracted from the clinical image data files. Once a user selects the folders containing the clinical image data files, the Clinical Image Upload Tool scans the clinical image data file(s) and uploads the attributes from the header that are specified in the configurable schema files (act 325). For example, the Clinical Image Upload Tool extracts at least the following attributes from the clinical image data files present in the selected folders based upon the configurable schema file shown in FIG. 8: patent identifier, patient name, study date, study time, and referring physician. In some embodiments, the Clinical Image Upload Tool selects a configurable schema file from a set of configurable schema files based on one or more factors: profile of the user, security permissions associated with the user, location of the selected folders/files, timing information (e.g., time of year (month, quarter, etc.), time of day (morning, afternoon, evening, etc.), current events (e.g., based on news reports, etc.), meta-information in the clinical image data file(s), source of the clinical image file(s), and so forth.

In some embodiments, the Clinical Image Upload tool enables access to configurable schema files automatically by implementing an API. The API includes one or more functions that enable the Clinical Image Upload tool to identify the relevant configurable schema files, access contents of the identified configurable schema files, and extract values for the specified attributes from each clinical image data file that are to be uploaded to the central data storage. This API may also be used by users of the Clinical Image Upload tool in order to provide a user interface for the manual review and/or examination of relevant configurable schema files (e.g., to add attributes, delete attributes, modify attributes, etc.).

Figure 5D:
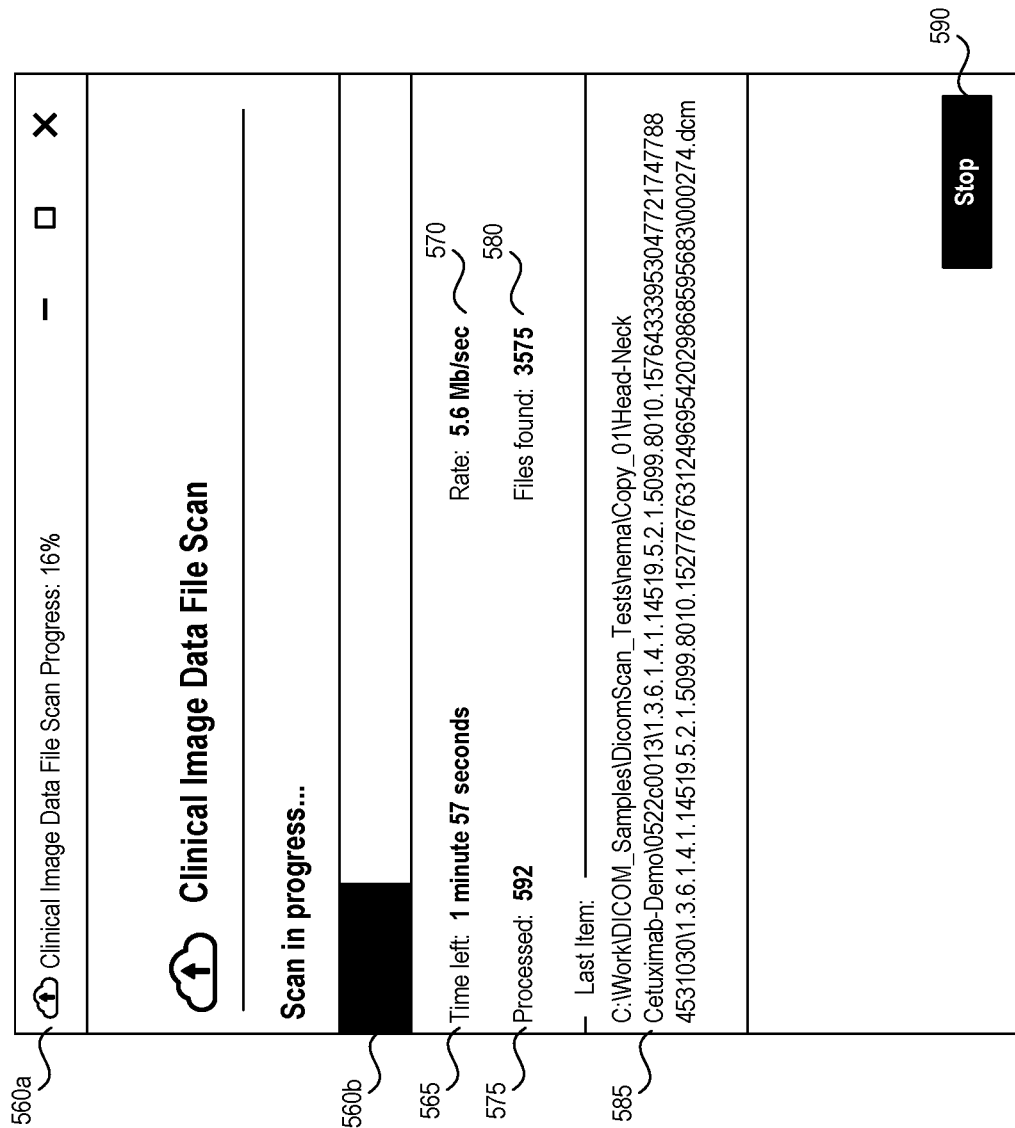

FIG. 5D depicts an illustrative graphical user interface for displaying clinical image data upload progress to a user. Upon receiving folder selection from a user, the Clinical Image Upload tool can present the upload progress of the various files in the selected folder(s) to the user. For example, the user interface can present the following fields: scan progress percentage 560a, scan progress meter 560b, estimated time left to complete the scan and upload 565, rate of scan/upload 570, number of files/folders processed 575, number of files found in the selected folder(s) 580, and the last item scanned/uploaded 585. The user may select to stop the file scan/upload by selection field 590. Foes that were uploaded successfully are counted as Processed. Any files that are not formatted as MOM data are counted as Errors. In some embodiments, when a user selects one or more folders to upload, only clinical image data files (e.g., DICOM data) inside the folder and any sub-folders is uploaded to Clinical Image Archiving solution. Any data that is not recognized as clinical image data (e.g., non-DICOM data) is skipped. The non-DICOM file names may then appear as errors in the upload results and the log file. The data that was successfully processed is copied to the central data storage repository configured for Clinical Image Archiving. Clinical image data is available to restore to configured healthcare endpoints. When the scan is complete, a user can perform one or more of the following actions: view the log file that lists the result of each file included in the scan operation, upload additional clinical image data, or close the Clinical Image Upload tool.

In addition to uploading new clinical image data files, the Clinical Image Archiving solution also enables a user to reindex existing clinical image data files to extract information about additional attributes. As discussed above, since the header files of clinical image data files comprise a large number of attributes, not all of which might be useful for a user, typical clinical image archiving solutions only extract a subset of attributes from each clinical image data file's header. However, this poses a problem if a user wants to view values for attributes that are not currently indexed (e.g., the metadata associated with the clinical data file does not include a value for the attributes and/or the metadata index, which stores an index to the data in the metadata file, does not include the additional attributes). For example, a user may be unable to search or browse a clinical image archive by specific age brackets if the metadata and/or the metadata index does not contain age meta information. The reindexing module of the Clinical Image Archiving solution allows the updating of meta-information on demand so that additional attributes are available for searching and/or browsing. As discussed above, FIG. 5B depicts an illustrative graphical user interface for receiving a mode selection (e.g., upload or reindexing) from a user. A user can select to reindex existing clinical image data files (field 545).

FIG. 6A depicts an illustrative graphical user interface for receiving file/folder selection(s) (for example, patient level, hospital level, trial level, etc.) from a user for clinical image data reindexing. The user can select specific patient folders or select all patient folders (field 605) for reindexing. For example, the user can select one or more patient folders stored at a storage location (e.g., the central storage repository) using control 610. In some embodiments of the invention, the reindexing module can limit the number of folders to scan. This may be done to increase the efficiency of the Clinical Image Archiving solution. Once a user has selected the folder to reindex, the user can select control 615 to start the reindexing process.

The user can also update the configurable schema file(s) associated with the Clinical Image Archiving solution to include the additional attributes for which values are to be extracted. For example, the user can update the configurable schema file depicted in FIG. 8 to include the age attribute, under the "Patient" Level, as follows:

```
<Attribute>
    <Name>PatientAge</Name>
    <Group>0010</Group>
    <Element>1010</Element>
</Attribute>
```

FIG. 3B depicts some salient operations of a method 350 for reindexing clinical data image files according to an illustrative embodiment of the present invention. Once the user has selected the folder locations, the reindexing module of the Clinical Image Archiving solution can download and/or scan the clinical image data files stored at the specified folders (act 330). In some embodiments of the invention, the reindexing module downloads only a specific portion (e.g., the first 4 kilobytes) of each clinical image data file in order to reindex the metadata. The reindexing module can determine the specific portion of each clinical image data file to download based on one or more of the following factors: type of clinical image data file, bandwidth constraints (e.g., maximum and/or minimum bandwidth of data links between endpoints (e.g., computers where medical imaging software is installed, data storage location(s), cloud storage location(s), etc.)), data storage constraints (e.g., capacity of destination data storage location where the extracted data and/or metadata is stored), response time constraints (e.g., Service Level Agreement (SLA) constraints), etc. For example, based upon the file type of each clinical image data file, the reindexing module may determine the portion of the clinical image data file that stores the relevant metadata (meta information). As an example, the header of a DICOM file stores the meta information. By downloading only a portion of the large clinical image data files, the reindexing module can increase the efficiency of the computing system by reducing the amount of transferring, processing, and/or analyzing of large data files. In some embodiments of the invention, the reindexing module can parse one or more of the clinical image files at a webserver associated with the central data storage repository instead of downloading the files at the endpoints (e.g., computers where medical imaging software is installed).

Once the reindexing tool has downloaded and/or scanned the clinical image data files, it can parse the clinical image data file headers for the attributes specified in the updated configurable schema file (act 335), and update the metadata and/or metadata index associated with each clinical image data file (act 340).

Figure 6B:
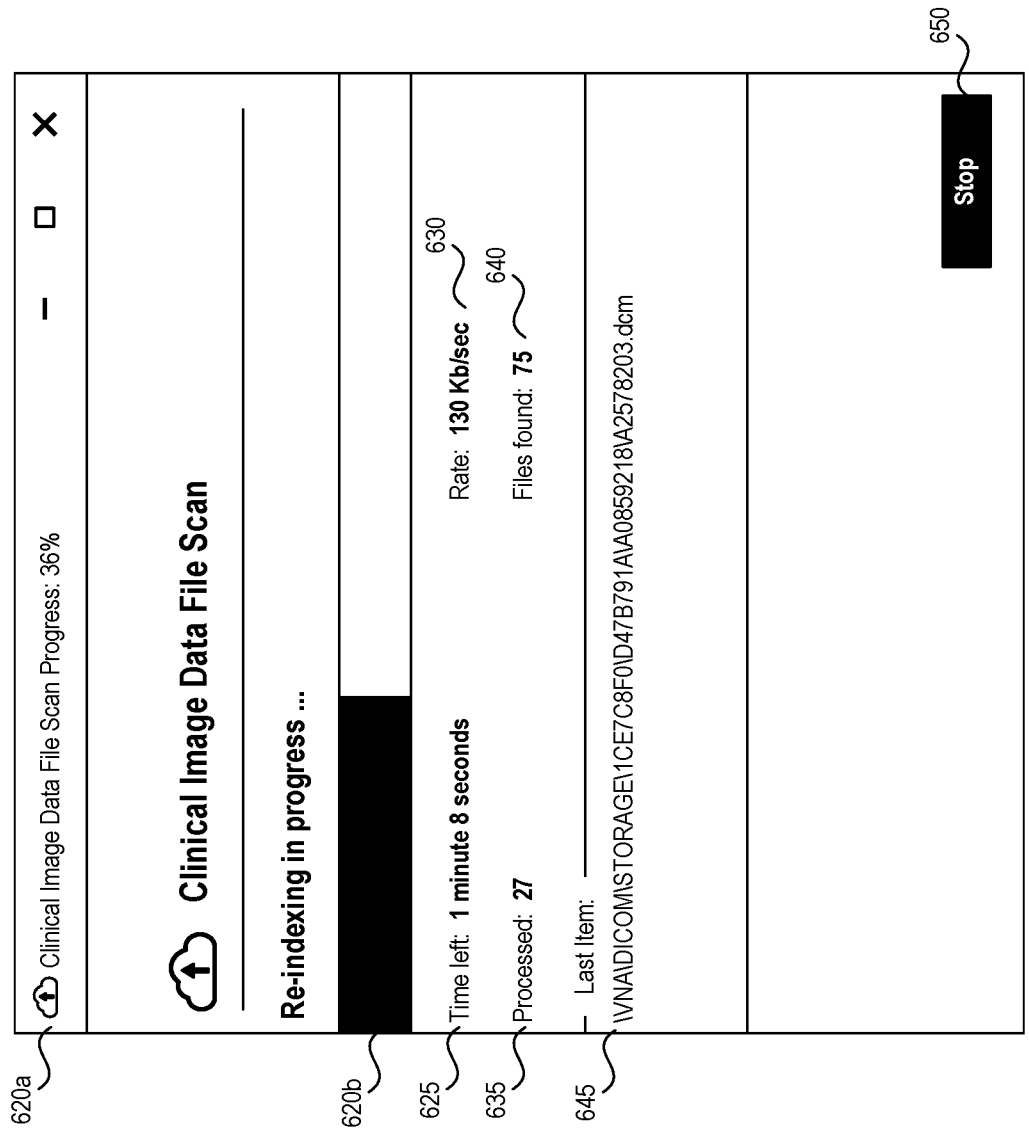
FIG. 6B depicts an illustrative graphical user interface for displaying clinical image data reindexing progress to a user.

FIG. 6B depicts an illustrative graphical user interface for displaying clinical image data reindexing progress to a user. Upon receiving folder selection from a user, the reindexing module can present the reindexing progress of the various files in the selected folder(s) to the user. For example, the user interface can present the following fields: scan progress percentage 610, scan progress meter (620a and/or 620b), estimated time left to complete the reindexing 625, rate of reindexing 630, number of files/folders processed 635, number of files found in the selected folder(s) 640, and the last item reindexed 645. The user may select to stop the file reindexing by selection field 650. Files that were reindexed successfully are counted as Processed. Any files that are not formatted as DICOM data are counted as Errors. In some embodiments, when a user selects one or more folders to reindexed, only clinical image data files (e.g., DICOM data) inside the folder and any sub-folders are reindexed. Any data that is not recognized as clinical image data (e.g., non-MOM data) is skipped. The non-DICOM file names may then appear as errors in the reindexing results and the log file. The data that was successfully processed is reindexed in the central data storage repository configured for Clinical Image Archiving. When the reindexing is complete, a user can perform one or more of the following actions: view the log file that lists the result of each file included in the reindexing operation, reindex additional clinical image data, or close the reindexing module. In some embodiments of the invention, if clinical image data files were uploaded into the central data storage repository and the index does not contain any clinical image data related information, then reindexing module will add the clinical image data related information to the index associated with each clinical image data file.

After the reindexing module updates the metadata index to include the additional attributes specified by the user (e.g., patient age), the user can then search and/or browse the clinical image data files based on the added attribute (e.g., search/browse by age brackets).

In regard to the figures described herein, other embodiments are possible within the scope of the present invention, such that the above-recited components, steps, blocks, operations, and/or messages/requests/queries/instructions are differently arranged, sequenced, sub-divided, organized, and/or combined. In some embodiments, a different component may initiate or execute a given operation.

Example Embodiments

Some example enumerated embodiments of the present invention are recited in this section in the form of methods, systems, and non-transitory computer-readable media, without limitation.

In some embodiments of the invention, a computer-implemented method is disclosed for on-demand metadata extraction and re-indexing of clinical image data. The method comprises receiving a list of files containing clinical image data. For example, the method may receive location (s) of at least one folder containing at least one clinical image data file, Examples of clinical image data files include, but are not limited to Digital Imaging and Communications in Medicine (DICOM), Analyze, Neuroimaging Informatics Technology Initiative (WTI), Mine, etc, Each file in the list of files is associated with a metadata file and/or a metadata index. The method also receives a list of metadata attributes. The list of metadata attributes is associated with clinical image data. The list of metadata attributes may be received as configurable schema file (e.g., XML, YML, etc.) that includes the list of metadata attributes. Some embodiments of the invention, the list of metadata attributes, may be stored in a data structure (e.g., a list, array, database table, csv file, etc.).

For each file in the list of files, the method retrieves at least a portion of the file. For example, the method may retrieve a header portion of the file, the first predetermined number of bits (e.g., x bits) of the file, a predetermined number of bits (e.g., x bits) of the file, or any other portion of the file (including the whole file). For each attribute in the list of metadata attributes, the method parses the retrieved portion of the file to identify a value associated with the attribute. The method then updates the metadata file (and/or metadata index) associated with the file to include the attribute and the identified value associated with the attribute.

In other embodiments, a system or systems may operate according to one or more of the methods and/or computer-readable media recited in the preceding paragraphs. In yet other embodiments, a method or methods may operate according to one or more of the systems and/or computer-readable media recited in the preceding paragraphs. In yet more embodiments, a computer-readable medium or media, excluding transitory propagating signals, may cause one or more computing devices having one or more processors and non-transitory computer-readable memory to operate according to one or more of the systems and/or methods recited in the preceding paragraphs.

Terminology

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Unless the context clearly requires otherwise, throughout the description and the claims, the words "comprise," "comprising," and the like are to be construed in an inclusive sense, as opposed to an exclusive or exhaustive sense, i.e., in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words using the singular or plural number may also include the plural or singular number respectively. The word "or" in reference to a list of two or more items, covers all of the following interpretations of the word: any one of the items in the list, all of the items in the list, and any combination of the items in the list. Likewise the term "and/or" in reference to a list of two or more items, covers all of the following interpretations of the word: any one of the items in the list, all of the items in the list, and any combination of the items in the list.

In some embodiments, certain operations, acts, events, or functions of any of the algorithms described herein can be performed in a different sequence, can be added, merged, or left out altogether (e.g., not all are necessary for the practice of the algorithms). In certain embodiments, operations, acts, functions, or events can be performed concurrently, e.g., through multi-threaded processing, interrupt processing, or multiple processors or processor cores or on other parallel architectures, rather than sequentially.

Systems and modules described herein may comprise software, firmware, hardware, or any combination(s) of software, firmware, or hardware suitable for the purposes described. Software and other modules may reside and execute on servers, workstations, personal computers, computerized tablets, PDAs, and other computing devices suitable for the purposes described herein. Software and other modules may be accessible via local computer memory, via a network, via a browser, or via other means suitable for the purposes described herein. Data structures described herein may comprise computer files, variables, programming arrays, programming structures, or any electronic information storage schemes or methods, or any combinations thereof, suitable for the purposes described herein. User interface elements described herein may comprise elements from graphical user interfaces, interactive voice response, command line interfaces, and other suitable interfaces.

Further, processing of the various components of the illustrated systems can be distributed across multiple machines, networks, and other computing resources. Two or more components of a system can be combined into fewer components. Various components of the illustrated systems can be implemented in one or more virtual machines, rather than in dedicated computer hardware systems and/or computing devices. Likewise, the data repositories shown can represent physical and/or logical data storage, including, e.g., storage area networks or other distributed storage systems. Moreover, in some embodiments the connections between the components shown represent possible paths of data flow, rather than actual connections between hardware. While some examples of possible connections are shown, any of the subset of the components shown can communicate with any other subset of components in various implementations.

Embodiments are also described above with reference to flow chart illustrations and/or block diagrams of methods, apparatus (systems) and computer program products. Each block of the flow chart illustrations and/or block diagrams, and combinations of blocks in the flow chart illustrations and/or block diagrams, may be implemented by computer program instructions. Such instructions may be provided to a processor of a general purpose computer, special purpose computer, specially-equipped computer (e.g., comprising a high-performance database server, a graphics subsystem, etc.) or other programmable data processing apparatus to produce a machine, such that the instructions, which execute via the processor(s) of the computer or other programmable data processing apparatus, create means for implementing the acts specified in the flow chart and/or block diagram block or blocks. These computer program instructions may also be stored in a non-transitory computer-readable memory that can direct a computer or other programmable data processing apparatus to operate in a particular manner, such that the instructions stored in the computer-readable memory produce an article of manufacture including instruction means which implement the acts specified in the flow chart and/or block diagram block or blocks. The computer program instructions may also be loaded to a computing device or other programmable data processing apparatus to cause operations to be performed on the computing device or other programmable apparatus to produce a computer implemented process such that the instructions which execute on the computing device or other programmable apparatus provide steps for implementing the acts specified in the flow chart and/or block diagram block or blocks.

Any patents and applications and other references noted above, including any that may be listed in accompanying filing papers, are incorporated herein by reference. Aspects of the invention can be modified, if necessary, to employ the systems, functions, and concepts of the various references described above to provide yet further implementations of the invention. These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

To reduce the number of claims, certain aspects of the invention are presented below in certain claim forms, but the applicant contemplates other aspects of the invention in any number of claim forms. For example, while only one aspect of the invention is recited as a means-plus-function claim under 35 U.S.C. sec. 112(f) (NA), other aspects may likewise be embodied as a means-plus-function claim, or in other forms, such as being embodied in a computer-readable medium. Any claims intended to be treated under 35 U.S.C. § 112(f) will begin with the words "means for," but use of the term "for" in any other context is not intended to invoke treatment under 35 U.S.C. § 112(f). Accordingly, the applicant reserves the right to pursue additional claims after filing this application, in either this application or in a continuing application.

What is claimed is:

1. A tangible computer-readable storage medium excluding transitory signals, and which contains instructions for performing a method of on-demand metadata extraction, the method comprising:
   receive, via an implementation of a function of an API invoked by at least one user device, a list of clinical image data files containing clinical image data, wherein each file in the list of files is associated with a metadata file,
      wherein the metadata files are stored in a location remote from the user devices, and
      wherein the remote location is a cloud storage device;
   receive a list of metadata attributes, via an implementation of a function of the API invoked by the at least one user device, wherein the list of metadata attributes are associated with clinical image data; and
   for each clinical image data file in the list of clinical image data files:
      retrieve only a header portion of the clinical image data file,
      wherein a size of the retrieved header portion of the clinical image data file is smaller than a size of the clinical image data file to thereby gain efficiencies in data transmission, and
      wherein the retrieved header portion includes only metadata; and,
      for each attribute in the list of metadata attributes:
         parse the retrieved header portion of the clinical image data file to identify a value associated with the attribute; and
         update the metadata file associated with the clinical image data file to include the attribute and the identified value associated with the attribute.

2. The tangible computer-readable storage medium of claim 1, wherein the method further comprises:
   indexing the updated metadata file associated with at least one clinical image data file in the list of clinical image data files using the attribute and the identified value associated with the attribute; and
   based upon the indexing, updating a metadata index associated with the at least one clinical image data file in the list of clinical image data files.

3. The tangible computer-readable storage medium of claim 1, wherein at least one clinical image data file in the list of clinical image data files is of type:
   Digital Imaging and Communications in Medicine (DICOM),
   Analyze,
   Neuroimaging Informatics Technology Initiative (NIFTI), or
   Minc.

4. The tangible computer-readable storage medium of claim 1, wherein receiving the list of metadata attributes comprises receiving a configurable schema file including the list of metadata attributes, and wherein the configurable schema file is selected from a set of configurable schema files based at least in part on three or more of:
   user profile,
   security permissions,
   one or more locations of the clinical image data files in list of clinical image data files,
   timing information, or
   news-based events.

5. The tangible computer-readable storage medium of claim 1, wherein the list of metadata attributes are stored in a data structure.

6. The tangible computer-readable storage medium of claim 1, wherein retrieving only the header portion of the clinical image data file comprises retrieving a predetermined number of bits of the clinical image data file,
   wherein the predetermined number of bits of the clinical image data file is determined based at least in part on two or more of:
   type of the clinical image data file,
   bandwidth constraints,
   data storage constraints, or
   response time constraints.

7. The tangible computer-readable storage medium of claim 1, wherein receiving a list of files containing clinical image data comprises receiving location of at least one folder containing at least one clinical image data file.

8. A computer-implemented method of on-demand metadata extraction, the method comprising:
   receive a list of files containing clinical image data, wherein each file in the list of files is associated with a metadata file;

receive a list of metadata attributes, wherein the list of metadata attributes are associated with clinical image data; and for each file in the list of files:
retrieve only a portion of the file, wherein the retrieved portion of the file is smaller than a size of the file; and
for each attribute in the list of metadata attributes:
parse the retrieved portion of the file to identify a value associated with the attribute; and
update the metadata file associated with the file to include the attribute and the identified value associated with the attribute.

9. The computer-implemented method claim 8, further comprising:
indexing the updated metadata file associated with at least one file in the list of files; and
based upon the indexing, updating a metadata index associated with the at least one file in the list of files.

10. The computer-implemented method claim 8, wherein at least one file in the list of files is of type:
Digital Imaging and Communications in Medicine (DICOM),
Analyze,
Neuroimaging Informatics Technology Initiative (NIFTI), or
Minc.

11. The computer-implemented method claim 8, wherein receiving the list of metadata attributes comprises receiving a configurable schema file including the list of metadata attributes.

12. The computer-implemented method claim 8, wherein the list of metadata attributes are stored in a data structure.

13. The computer-implemented method claim 8, wherein retrieving the at least a portion of the file comprises retrieving a header portion of the file.

14. The computer-implemented method claim 8, wherein retrieving only the portion of the file comprises retrieving a predetermined number of bits of the file.

15. The computer-implemented method claim 8, wherein receiving a list of files containing clinical image data comprises receiving location of at least one folder containing at least one clinical image data file.

16. An apparatus, coupled to a network and configured to perform on-demand metadata extraction, the apparatus comprising:
at least one hardware processor coupled to the network; and,
at least one memory storing instructions, which when executed by the at least one processor, performs a method to:
receive a list of files containing clinical image data, wherein each file in the list of files is associated with a metadata file;
receive a list of metadata attributes, wherein the list of metadata attributes are associated with clinical image data; and
for each file in the list of files:
retrieve only a header portion of the file,
wherein the retrieved header portion of the is smaller than a size of the file such that retrieving only the header portion results in data transmission efficiency gains, and
wherein the retrieved header portion includes only metadata; and
for each attribute in the list of metadata attributes:
parse the retrieved header portion of the file to identify a value associated with the attribute; and
update the metadata file associated with the file to include the attribute and the identified value associated with the attribute.

17. The apparatus claim 16, wherein the method further comprises:
indexing the updated metadata file associated with at least one file in the list of files; and
based upon the indexing, updating a metadata index associated with the at least one file in the list of files.

18. The apparatus claim 16, wherein at least one file in the list of files is of type:
Digital Imaging and Communications in Medicine (DICOM),
Analyze,
Neuroimaging Informatics Technology Initiative (NIFTI), or
Minc.

19. The apparatus claim 16, wherein receiving the list of metadata attributes comprises receiving a configurable schema file including the list of metadata attributes.

* * * * *